United States Patent [19]
Foulkes et al.

[11] Patent Number: 6,136,779
[45] Date of Patent: *Oct. 24, 2000

[54] METHODS OF SPECIFICALLY TRANSCRIPTIONALLY MODULATING THE EXPRESSION OF GENE OF INTEREST

[75] Inventors: J. Gordon Foulkes, Huntington Station; Franz Leichtfried, Bellerose; Christian Pieler, Westbury; John R. Stephenson, Rockville Centre, all of N.Y.

[73] Assignee: OSI Pharmaceuticals, Inc., Uniondale, N.Y.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/778,754

[22] Filed: Jan. 6, 1997

Related U.S. Application Data

[63] Continuation of application No. 08/267,834, Jun. 28, 1994, Pat. No. 5,665,543, which is a continuation of application No. 08/134,215, Oct. 8, 1993, abandoned, which is a continuation of application No. 08/013,343, Feb. 4, 1993, abandoned, which is a continuation of application No. 07/555,196, Jul. 18, 1990, abandoned, which is a continuation of application No. 07/382,712, Jul. 18, 1989, abandoned.

[51] Int. Cl.⁷ ............................. A01K 31/00; C12P 21/00
[52] U.S. Cl. ........................ 514/1; 435/69.1; 435/325; 435/366
[58] Field of Search .................... 435/69.1, 325, 435/366; 514/1

[56] References Cited

U.S. PATENT DOCUMENTS

| | | | |
|---|---|---|---|
| 4,535,058 | 8/1985 | Weinberg et al. | 435/64.1 |
| 4,601,978 | 7/1986 | Karin | 435/64.1 |
| 4,699,877 | 10/1987 | Cline et al. | 435/6 |
| 4,699,874 | 10/1987 | Barton | 536/23.1 |
| 4,721,669 | 1/1988 | Barton | 435/6 |
| 4,736,866 | 4/1988 | Leder et al. | 435/64.1 |
| 4,738,922 | 4/1988 | Haseltine et al. | 435/64.1 |
| 4,740,461 | 4/1988 | Kaufman | 435/64.1 |
| 4,740,463 | 4/1988 | Weinberg et al. | 435/64.1 |
| 4,761,367 | 8/1988 | Edgell et al. | 435/6 |
| 4,761,371 | 8/1988 | Bell et al. | 435/6 |
| 4,806,463 | 2/1989 | Goodchild et al. | 435/64.1 |
| 4,810,643 | 3/1989 | Souza | 435/64.1 |
| 4,827,079 | 5/1989 | Evans et al. | 435/6 |
| 4,861,709 | 8/1989 | Ulitzer et al. | 435/64.1 |
| 4,885,238 | 12/1989 | Reddel et al. | 435/64.1 |
| 4,935,363 | 6/1990 | Brown et al. | 435/6 |
| 4,981,783 | 1/1991 | Augenlicht | 435/6 |
| 4,981,784 | 1/1991 | Evans et al. | 435/6 |
| 4,981,790 | 1/1991 | Haseltine et al. | 435/64.1 |
| 5,070,012 | 12/1991 | Nolan et al. | 435/64.1 |
| 5,071,773 | 12/1991 | Evans et al. | 435/64.1 |
| 5,075,229 | 12/1991 | Hanson et al. | 435/64.1 |
| 5,087,438 | 2/1992 | Gordon | 424/9 |
| 5,262,300 | 11/1993 | Evans et al. | 435/6 |
| 5,540,931 | 7/1996 | Hewitt et al. | 424/434 |
| 5,578,483 | 11/1996 | Evans et al. | 435/6 |
| 5,580,722 | 12/1996 | Foulkes et al. | 435/91.1 |
| 5,602,009 | 2/1997 | Evans et al. | 435/6 |
| 5,776,502 | 7/1998 | Foulkes et al. | 424/617 |

FOREIGN PATENT DOCUMENTS

| | | |
|---|---|---|
| 117058 | 8/1984 | European Pat. Off. |
| 332104 | 9/1989 | European Pat. Off. |
| WO8902472 | 5/1989 | WIPO |

OTHER PUBLICATIONS

Andersen, R. et al. (1990) "Metal–Dependent Binding of A Nuclear Factor to the Rat Metallothionein–I Promoter," Nucleic Acids Research 18(20):6049–6055.

Angel, P. et al., (1987 A) "Phorbol Ester–Inducible Genes Contain A Common Cis Element Recognized by An TPA–Modulated Trans–Acting Factor," Cell 49:729–739.

Angel, P. et al., (1987 B) "12–O–Tetradecanoyl–Phorbol–13–Acetate Induction of the Human Collagenase Gene Is Mediated by an Inducible Enhancer Element Located in the 5'–Flanking Region," Molecular and Cellular Biology, 7:2256–2266.

Bickel, M. et al., (1988) "Granulocyte–Macrophage Colony–Stimulating Factor Regulation in Murine T Cells and Its Relation to Cyclosporin A," Ex. Hematol. 16:691–695.

Blumberg, P., (1988) "Protein Kinase C as the Receptor for the Phorbol Ester Tumor Promoters: Sixth Rhoads Memorial Award Lecture," Cancer Research 48:1–8.

Brasier, A. et al., (1989) "Optimized Use of the Firefly Luciferase Assay as a Reporter Gene in Mammalian Cell Lines," BioTechniques 7(10):1116–1122.

Brenner C. et al., (1989) "Message Amplification Phenotyping (MAPPing): A Technique to Simultaneously Measure Multiple mRNAs from Small Numbers of Cells," BioTechniques 7(10):1096–1103.

Cao, T., (1989) "A Simple and Inexpensive System to Amplify DNA by PCR," BioTechniques 7(6):566–567.

Cohen, P. and Foulkes, J.G. eds., (1991) The Hormonal Control of Gene Transcription, 92–93, 235–236.

(List continued on next page.)

Primary Examiner—Stephanie Zitomer
Attorney, Agent, or Firm—John P. White; Cooper & Dunham LLP

[57] ABSTRACT

The present invention provides a method of transcriptionally modulating the expression of a gene-of-interest. The method comprises contacting a cell which is capable of expressing the gene with an amount of a molecule effective to transcriptionally modulate expression of the gene and thereby affect the level of the protein encoded by the gene which is expressed by the cell. Molecules useful in the practice of the invention are characterized as follows (a) do not naturally occur in the cell, (b) bind to DNA or RNA or bind to a protein through a domain of such protein which is not a ligand binding domain of a receptor which naturally occurs in the cell. Additionally, this invention provides a method for determining whether a molecule known to be a modulator of protein biosynthesis is capable of transcriptionally modulating expression of a gene-of-interest.

40 Claims, 57 Drawing Sheets

OTHER PUBLICATIONS

Comb, M. et al. (1986) "A Cyclic AMP– and Phorbol Ester–Inducible DNA Element," Nature 323:353–356.

Connelly, C. et al., (1989) "The Role of Transgenic Animals in the Analysis of Various Biological Aspects of Normal and Pathologic States," Experimental Cell Research 183:257–276.

Cybulsky, M. et al., (1991) "Gene Structure, Chromosomal Location, and Basis for Alternative mRNA Splicing of the Human VCAM1 Gene," Proc. Natl. Acad. Sci. USA 88:7859–7863.

Das, H. et al., (1988) "Cell Type–Specific Expression of the Human ApoB Gene Is Controlled by Two Cis–Acting Regulatory Regions," Journal of Biological Chemistry 263(23):11452–11458.

de Wet et al., (1987) "Firefly Luciferase Gene: Structure and Expression in Mammalian Cells," Molecular and Cellular Biology 7(2):725–737.

Emmel, E. et al., (1989) "Cyclosporin A Specifically Inhibits Function of Nuclear Proteins Involved in T Cell Activation," Science 246:1617–1620.

Engebrecht, J. et al., (1985) "Measuring Gene Expression with Light," Science 227:1345–1347.

Gunter, K. et al., (1989) "Cyclosporin A–Mediated Inhibition of Mitogen–Induced Gene Transcription Is Specific for the Mitogenic Stimulus and Cell Type," Journal of Immunology 142:3286–3291.

Higuchi, K. et al., (1988) "Tissue–Specific Expression of Apolipoprotein A–I (ApoA–I) Is Regulated by the 5'–Flanking Region of the Human ApoA–I Gene," Journal of Biological Chemistry 263(34):18530–18536.

Holbrook, N. et al., (1984) "T–Cell Growth Factor: Complete Nucleotide Sequence and Organization of the Gene in Normal and Malignant Cells," Proc. Natl. Acad. Sci. USA 81:1634–1638.

Hsu, M. et al., (1991) "Inhibition of HIV Replication in Acute and Chronic Infections in Vitro by a Tat Antagonist," Science, 254:1799–1802.

Ishii, S. et al., (1985) "Characterization and Sequence of the Promoter Region of the Human Epidermal Growth Factor Receptor Gene," Proc. Natl. Acad. Sci. USA 82:4920–4924.

Kaushansky, K. et al., (1985) "Genomic Cloning, Characterization, Multilineage Growth–Promoting Activity of Human Granulocyte–Macrophage Colony–Stimulating Factor," Proc. Natl. Acad. Sci. USA 83:3101–3105.

Kawasaki, E. et al., (1985) "Molecular Cloning of a Complementary DNA Encoding Human Macrophage–Specific Colony–Stimulating Factor (CSF–1)," Science 230:291–296.

Knott, T. et al., (1986) "Complete Protein Sequence and Identification of Structural Domains of Human Apolipoprotein B," Nature 323:734–738.

Kronke, M. et al., (1984) "Cyclosporin A Inhibits T–Cell Growth Factor Gene Expression at the Level of mRNA Transcription," Proc. Natl. Acad. Sci. USA 81:5214–5218.

Ladner, M. et al., (1987) "Human CSF–1: Gene Structure and Alternative splicing of mRNA Precursors," The EMBO Journal 6(9):2693–2698.

Lamb, P. et al., (1986) "Characterization of the Human p53 Gene," Molecular and Cellular Biology 6(5):1379–1385.

Lefevre, C. et al., (1987) "Tissue–Specific Expression of the Human Growth Hormone Gene Is Conferred in Part by the Binding of a Specific Trans–Acting Factor," The EMBO Journal 6(4):971–981.

Lim, K. et al., (1989) "A Simple Assay for DNA Transfection by Incubation of the Cells in Culture Dishes with Substrates for Beta–Galactosidase," BioTechniques 7(6):576–579.

Lin, F. et al., (1985) "Cloning and Expression of the Human Erythropoietin Gene," Proc. Natl. Acad. Sci. USA 82:7580–7584.

Majesky, M. et al., (1990) "PDGF Ligand and Receptor Gene Expression during Repair of Arterial Injury," Journal of Cell Biology 111:2149–2158.

Maniatis, T. et al., (1987) "Regulation of Inducible and Tissue–Specific Gene Expression," Science 236:1237–1245.

Mayo, K. et al., (1982) "Altered Regulation of the Mouse Metallothionein–I Gene Following Gene Amplification or Transfection," (in *Gene Amplification*) Schimke, R.T. ed., 67–73.

McCall, C. et al., (1989) "Biotherapy: A New Dimension in Cancer Treatment," Bio/Technology 7:231–240.

Metzler, D., (1977) *Biochemistry: The Chemical Reactions of Living Cells,* 116–117.

Munjaal, R. et al., (1989) "In Situ Detection of Progesterone Receptor mRNA in the Chicken Oviduct Using Probe–on Slides," BioTechniques 7(10):1104–1108.

Myoken, Y. et al., (1991) "Vascular Endothelial Growth Factor (VEGF) Produced by A–431 Human Epidermoid Carcinoma Cells and Identification of VEGF Membrane Binding Sites," Cell Biology 88:5819–5823.

Nagata, S. et al., (1986) "The Chromosomal Gene Structure and Two mRNAs for Human Granulocyte Colony–Stimulating Factor," The EMBO Journal 5(3):575–581.

Nimer, S. et al., (1988) "Serum Cholesterol–Lowering Activity of Granulocyte–Macrophage Colony–Stimulating Factor," JAMA 260(22):3297–3300.

Nishizuka, Y., (1986) "Studies and Perspectives of Protein Kinase C," Science 233:305–312.

Paul, W. (1984) *Fundamental Immunology,* 275–276.

Pons, M. et al., (1990) "A New Cellular Model of Response to Estrogens: A Bioluminescent Test to Characterize (Anti) Estrogen Molecules," BioTechniques 9(4):450–459.

Rao, A. et al., (1990) "A Quantitative Assay for β–D–Glucuronidase (GUS) Using Microtiter Plates," BioTechniques 8(1):38–40.

Ratner, M., (1989) "Can the Antisense Message Be Delivered?," Bio/Technology 7:207.

Reisman, D. et al., (1989) "Two Promoters that Map to 5'–Sequences of the Human p53 Gene Are Differentially Regulated during Terminal Differentiation of Human Myeloid Leukemic Cells," Biol. Abstr. 88(9):AB–673.

Rinkus, S. et al., (1980) "The Need for Both in Vitro and in Vivo Systems in Mutagenicity Screening," in *Chemical Mutagens,* de Serres et al., ed., 6:365–473.

Roesler, W. et al., (1988) "Cyclic AMP and the Induction of Eukaryotic Gene Transcription," Journal of Biological Chemistry 263(19):9063–9066.

Sambrook, J. et al., (1989) "Strategies for Studying Gene Regulation," *Molecular Cloning: A Laboratory Manual,* 2nd Ed., 16.56–16.58.

Seguin, C. et al., (1987) "Regulation in Vitro of Metallothionein Gene Binding Factors," Science 235:1383–1387.

Singleton, P. et al., (1987) Dictionary of Microbiology and Molecular Biology, p. 314 and p. 382.

Slack, J. et al., (1989) "Application of the Multiscreen System to Cytokine Radioreceptor Assays," BioTechniques 7(10):1132–1138.

Standaert, R. et al., (1990) "Molecular Cloning and Overexpression of the Human FK506–Binding Protein FKBP," Nature 346:671–674.

Stanley, E. et al., (1985) "The Structure and Expression of the Murine Gene Encoding Granulocyte–Macrophage Colony Stimulating Factor: Evidence for Utilisation of Alternative Promoters," The EMBO Journal 4(10):2569–2573.

Stinski, M. et al., "Activation of the Major Immediate Early Gene of Human Cytomegalovirus by Cis–Acting Elements in the Promoter–Regulatory Sequence and by Virus–Specific Trans–Acting Components," Journal of Virology 55(2):431–441.

Tal, M. et al., (1987) "Human HER2 (neu) Promoter: Evidence of Multiple Mechanisms for Transcriptional Initiation," Molecular and Cellular Biology 7(7):2597–2601.

Tischer, E. et al., (1991) "The Human Gene for Vascular Endothelial Growth Factor," Journal of Biological Chemistry 266(18):11947–11954.

Tocci, M. et al., "The Immunosuppressant FK506 Selectively Inhibits Expression of Early T Cell Activation Genes," Journal of Immunology 143(2):718–726.

Ulitzer, S. et al., "Detection and/or Identification of Microorganisms in a Test Sample Using Bioluminescence or Other Exogenous Genetically–Introduced Marker," U.S. Patent No. 4,861,709 issued Aug. 29, 1989 from U.S. Serial No. 739,957, filed May 31, 1985.

Willingham, M. et al., (1990) "A Reversible Multi–Well Chamber for Incubation of Cultured Cells with Small Volumes: Application to Screening of Hybridoma Fusions Using Immunofluorescence Microscopy," BioTechniques 8(3):320–324.

Wu, K. et al. "Aspirin Inhibits Interleukin 1–Induced Prostaglandin H Synthase Expression in Cultured Endothelial Cells," Proc. Natl. Acad. Sci. USA 88:2384–2397.

Yang, Y. et al., (1986) "Human IL–3 (Multi–CSF): Identification by Expression Cloning of a Novel Hematopoietic Growth Factor Related to Murine IL–3," Cell 47:3–10.

Vellenga, E. et al., (1988) "Independent Regulation of M–CSF and G–CSF Gene Expression in Human Monocytes," Blood 71 (6): 1529–1532.

Lee, M–T. et al., (1990) "Differential Expression of M–CSF, G–CSF, and GM–CSF by Human Monocytes" Biol. Abstr. 89 (10): AB–100645.

Tamura, R. and Cox, G. S., (1988) "Effect of Pyrimidine Deoxynucleosides and Sodium Butyrate on Expression of the Glycoprotein Hormone α–Subunit and Placental Alkaline Phosphatase in HeLa Cells," Chemical Abstracts 108 (15) :AB–124167.

Alberts, A.W. (1988) in Atherosclerosis Reviews, vol. 18, eds. J. Stokes III and M. Mancini, Raven Press, pp. 123–131.

Henwood, J.M. and Heel, R.C., in Drugs (1988) 36:429–454.

Teutsch, G. et. al. (1993) in Chronicles of Drug Discovery, vol. 3, ed. D. Lednicer, American Chemical Society, pp. 1–43 eutsch, G. et. al. (1993) in Chronicles of Drug.

Philibert, D. et al. (1985) in The Antiprogestin Steroid RU 486 and Human Fertility Control, pp. 49–68.

Henderson, D. (1987) in Pharmacology and Clinical Uses of Inhibitors of Hormone Secretion and Action. Eds. Furr B.J.A. and Wakeling, A.E., Bailliere Tindal, pp. 184–211, on p. 185, 1st paragraph.

Jordan,l V.C. (1988) Endocrinology 122(4):1449–1454, the use of an in vitor assay is chosed due to its ability to predict activity, pp. 1449, col. 2.

Murphy, C.S. and Jordan, V.C. (May, 1989) J. Steroid Biochemistry, 34(1–6):407–411):p. 410, column 2, last para. To p. 411, col. 1.

Verheyden, J.P.H. (1993) in The Search for Antiviral Drugs: Case Histories form Concept to Clinic. Eds. J. Adams and V.J. Merluzzi, Birkhauser, p. 299–325.

Pattishall, K.H. (1993) in The Search for Antiviral Drugs: Case Histories from Concept to Clinic, Eds. J. Adams and V.J. Merluzzi, Birkhauser, p. 23–43.

Furman, P.A. et. al. (1986) Proc. Natl. Acad. Sci. USA 83:8333–8337.

Wakeling, A.E. and Bowler, J. (1987) J. Steroid Biochem. 30(1–6):141–147.

Allison, A.C. (1993) in Annal. N.Y. Acad. Sci. 696:xi–xx).

Kronke, M. et al. (1984) Proc. Natl. Acad. Sci. 81:5214–5218.

Pont, A. et al. (1982) Arch. Intern. Med. 97:370.

Feldman, D. (1986) Endocrine Reviews 7(4):409–420).

Glass, C.K. et. al. (1991) in The Hormonal Control of Gene Transcription, Eds. Cohen, P. and Foulkes, J G., Elsevier, pp. 129–157.

Neuhold, L.A. et. al., (1986) DNA 5(5):403–411.

Israel, D.I. et.al. (1984) J. Biol. Chem. 259:5400–5402.

Gonzalez, F.J. et. al. (1984) Mol. Pharmacol. 26:117–121.

Patchett, A.A. (1993) in Chronicles of Drug Discovery, vol. 3, ed. D. Lednicer, American Chemical Society, p. 125–162.

Wall, M.E. et. Al. (1993) in Chronicles of Drug Discovery, vol. 3, ed. D. Lednicer, American Chemical Society, pp. 327–348.

Kopan, R. et. al. (1987) J. Cell. Biol. 105:427–440.

Evans, R.M. (1988) Science 240:889–895.

Kaplan, R.P. et. al. (1983) J. Amer. Acad. Dermatol. 8:95–102.

Gordee, R.S. et. al. (1992) in New Approaches for Antifungal Drugs, Ed. Fernandes, Prabhavathi B., Birkhauser, pp. 46–63.

Gordee, R.S. et. al. (1984) J. Antibiot. 37:1054–1065.

Gordee, R.S. et. al. (1988) Ann. N.Y. Acad. Sci. 544:294–309.

Debono, M. et. al. (1988) Ann. N.Y. Acad. Sci. 544:152–167.

Fromtling, R.A. and Abruszzo, G.K. (Feb. 1989) J. Antibiot. 42(2);174–178.

Tocci, M.J. et. al. (Jul. 15, 1989) J. Immunol. 143(2):718–726.

Kino, T. et. al. (1987) J. Antibiot. 40:1249–1255.

Bell, R.L. et. al. (1992) Int. J. Immunopharmac. 14(3):505–510.

Carter, G.W. et. al. (1989) in Leukotrienes and Prostanoids in Health and Disease, Eds. Zor. U. et. al. Karger, pp. 50–55.

Sweeney, F.J. et. al. (1987) Prostaglandins, Leukotrienes and Medicine 28:73–93.

Furr, B.J.A. et. al. (1987) J. Endocrinol. 113:R7–R9.

Godley, J.M. & Brand S.J. (1989) Proc. Natl. Acad. Sci USA, 86,3036–3040 (Exhibit 2).

Doppler, W., Groner B. & Ball R.K., (1989) Proc. Natl. Acad. Sci USA, 86, 104–108 (Exhibit 3).

Druege P.M. et al., (1986) Nuc. Acids Res. 14(23):9329–9334 (Exhibit 4).

Features of the Mammalian Expression Shuttle Vector pUV102 with inserted TK-NEO Cassette

Figure 11a
Sequence of the pUV Oligonucleotides pUV1:
5'TCGACCCGGCGGCCCGCTGATCAGAGCGTCGGGCCGGTACCGTGCACTACGTAAGATCTAAGCTT3' pUV2:
5'ACTAGTCTGCAGGCTAGCACTCTTCTGGTCCCCACAGACTCAGAGAACCACCACATGGA3' pUV3:
5'AGACGCCAAAAACATCAAGAAAAGGCCCGGCCATTCTATCCCTCTAGAGGGGATCCAGCTG3' pUV4:
5'TAGATCTTACGTAGTGCACGGTACCGGCCCGACGTCTGATCAGCGGGCCGCCGGG3' pUV5:
5'GGTGGGTTCTCTCTGAGTCTGTGGGGACCAGAAGAGTGCTAGCCTGCAGCTAGTAAGCT3' pUV6:
5'AATTCAGCTGGATCCCCTCTAGAGGGATAGAATGGCCGGGCCCTTTCTTGATGTTTTTGGCGTCTTCCAT3'

Construction of pUV001

Construction of pUV100

Construction of pUV102 and pUV103

Synthetic HSV-TK Promoter

Figure 15

Oligo #1:  5'- AGCTTGGCCCCTAGGGCCACTAGTCTGCAGCTATGATGACACAA
ACCCCGCCCAGCGTCTGTCATTGGCGA-3'

Oligo #2:  3'- ACCGGGGATCCCGGTGATCAGACTCGATACTACTGTGTTGGGG
CGGGTCGCAGAACAGTAACCGCTTAAGCT-5'

Oligo #3:  5'- ATTCGAACACGCAGATGCAGTCGGGGGGGCGCGGTCCGAGGTC
CACTTCGCATATTAAGGTGACGCGTGTGGG-3'

Oligo #4:  3'- TGTGCGTCTACGTCAGCCCCCGCGCCAGGCTCCAGGTGAAG
CGTATAATTCCACTGCGCACACCCGATC-5'

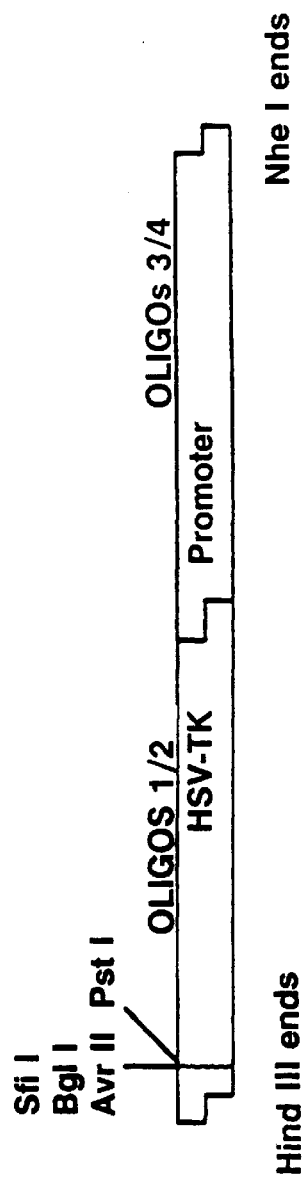

Construction of pTKL100

Construction of pTKNEO3

Structure of GM-CSF Clone

Key

S = Sal I
H = Hind III
E = Eco RI
B = Bst EII
R = Rsa I
↱ = start of transaction Synthetic Oligo for GM-CSF/Luciferase ATG Fusion

Figure 21

Eco RI ends    Bst E II

OLIGO 1: 5'- AATTCGGTCACCATTAATCATTTCCTCTGTGTATTTAAGAGCTCTTTTGCCAGTGAGCCCAGTACACAG -3'

OLIGO 2: 3'- GCCAGTGGTAATTAGTAAAGGAGACACATAAATTCTCGAGAAAACGGTCACTCGGGTCATGTGTCT CTCTTTCCG -5'

ATG    Xba I ends

OLIGO 3: 5'- AGAGAAAGGCTAAAGTTCTCTGGAGGATGGAAGACGCCAAAAACATCAAGAAAGGCCCGGCGCCATTCTATCCT-3'

OLIGO 4: 3'- ATTTCAAGAGACCTCCTACCTTCTGCGGTTTTTGTAGTTCTTTCCGGGCCGCGGTAAGATAGGAGATC -5'

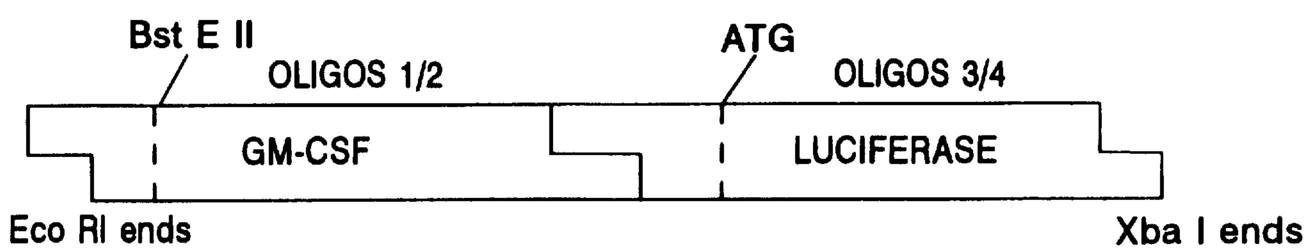

Construction of pGMLS102 and pGMLS103
Figure 22
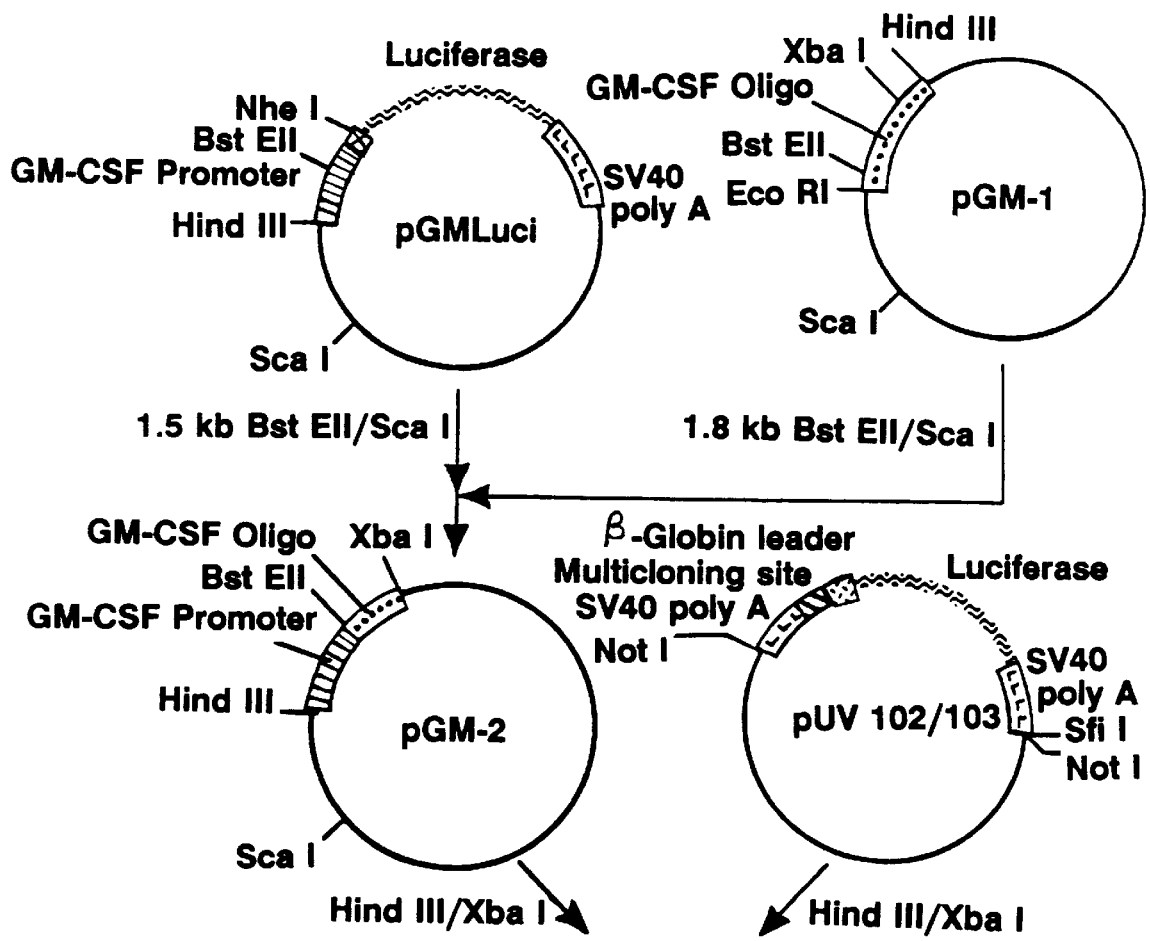
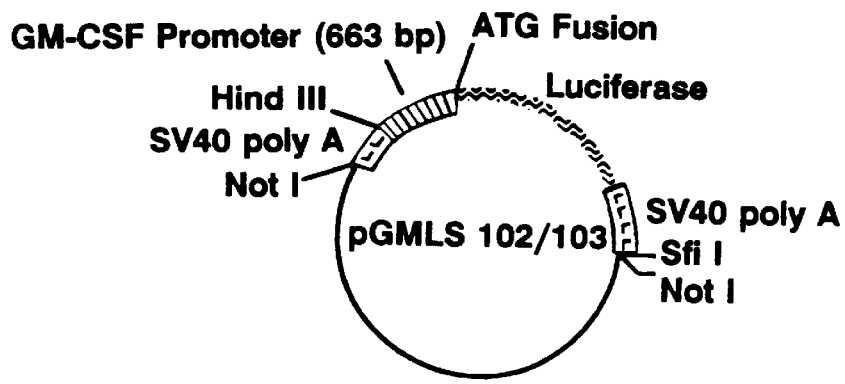

Construction of pGMLL102 and pGMLL103

Construction of CSF1-pTZ18

Construction of p100-RH

Construction of p100-2

Construction of p100-RHC

Construction of pCSF1-102

Construction of pGUC84

Construction of pGUV100

Construction of pGUV2

Construction of pGUV140

Construction of pGUV150

Construction of pEP-7.5B

Construction of pRE

Construction of IL-3-pTZ18R

Response of GEMs Cell Clones to Known Inducers

Effects of Steroids on Clone M10

Examples of Primary Screen Lead Chemicals - Specific Transcriptional Inducers

Examples of Primary Screen Lead Chemicals Specific Transcriptional Inhibitors

FIGURE 47
Dose Response Analysis
Figure 47a
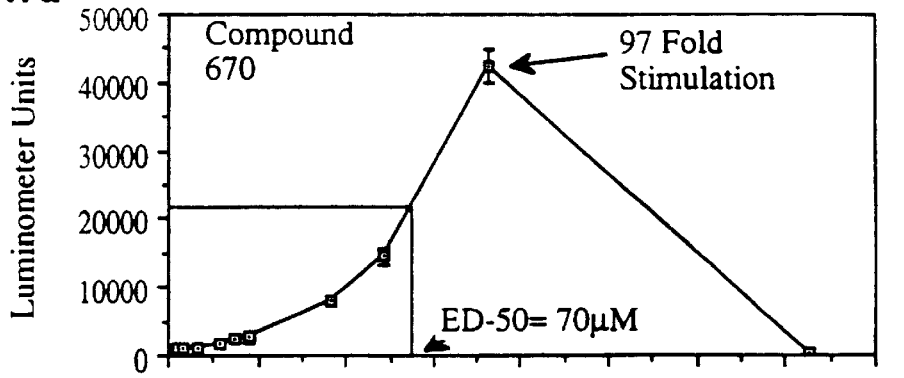
Figure 47b
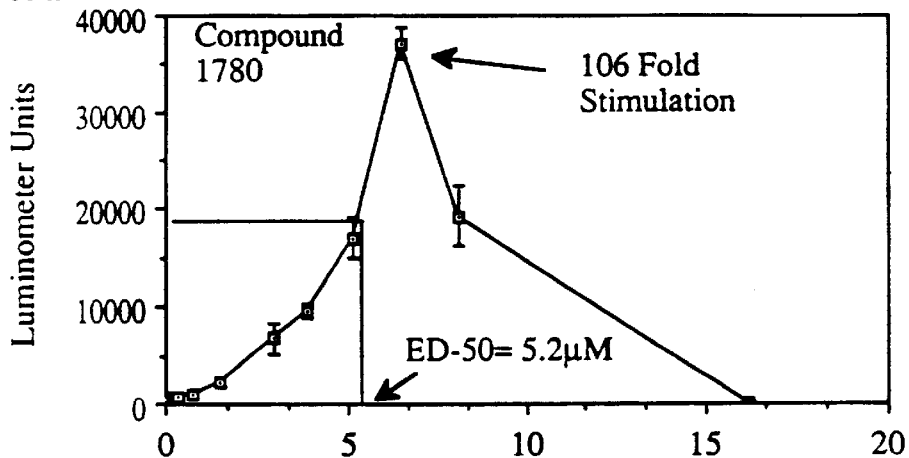
Figure 47c
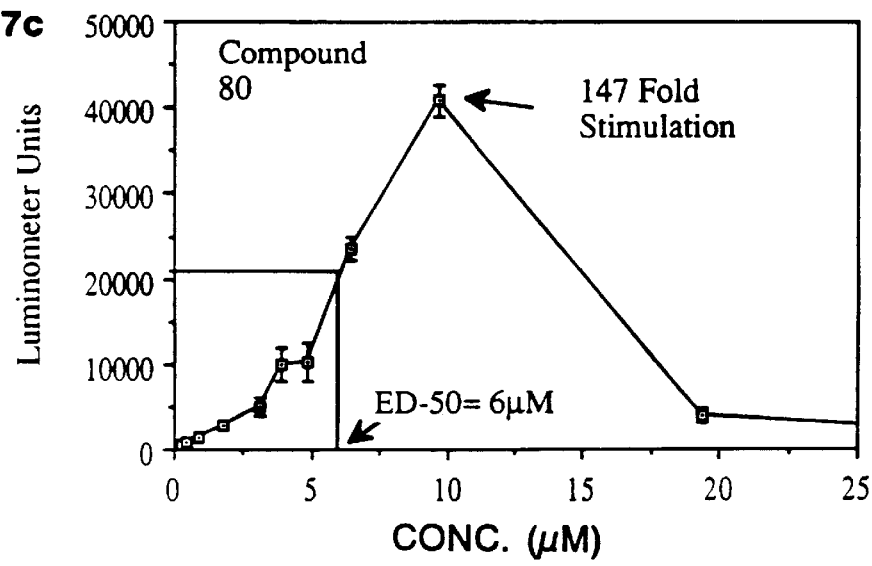

FIGURE 51
Figure 51a
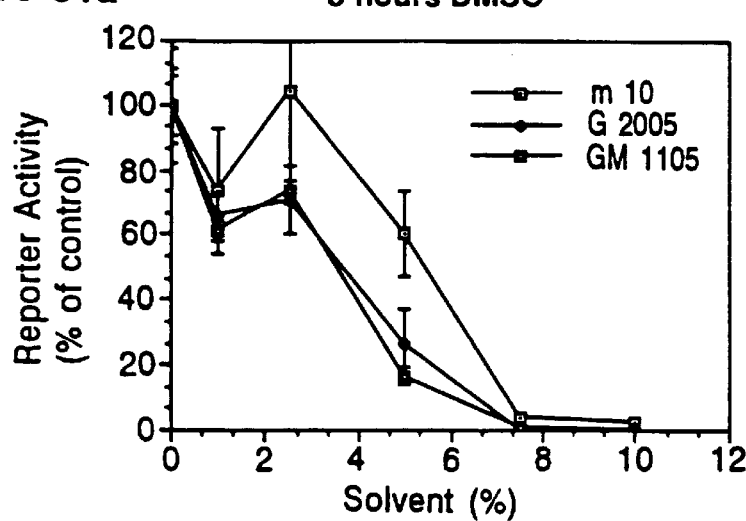
Figure 51b
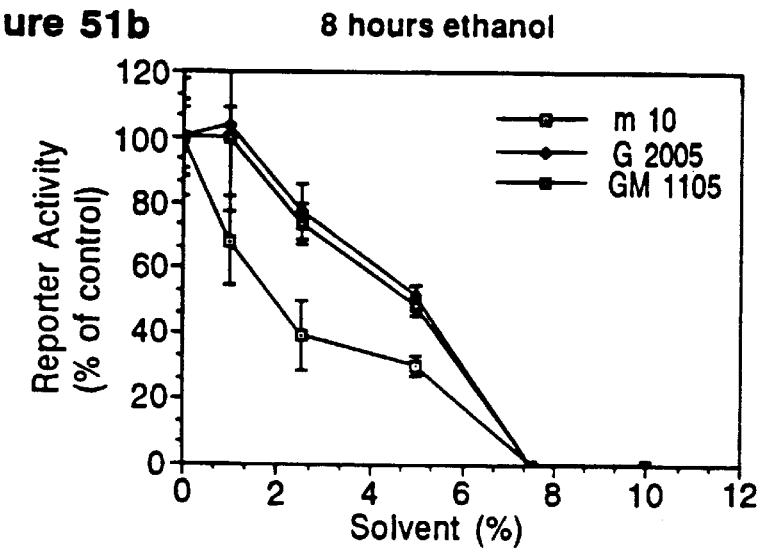
Figure 51c
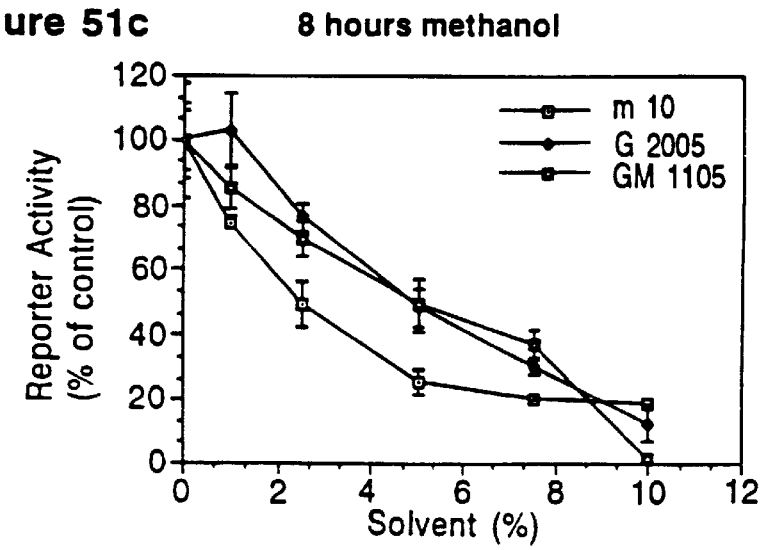

Promoter/Luciferase Pilot Screen
of Fermentation Broth Samples
Lead Samples

Figure 52

| Fermentation Broths | Promoter / TIR | | | Number of Hits | |
|---|---|---|---|---|---|
| | G | GM | MTV | Inducers | Inhibitors |
| methanol extracts: 176 total | > 2.0 < 0.6 | > 0.8 | > 0.8 | 0 | 0 |
| | > 0.8 | > 2.0 < 0.6 | > 0.8 | 1 | 0 |
| | > 0.8 | > 0.8 | > 2.5 < 0.6 | 7 | 0 |
| aqueous fractions: 180 total | > 2.0 < 0.6 | > 0.8 | > 0.8 | 7 | 0 |
| | > 0.8 | > 1.8 < 0.6 | > 0.8 | 1 | 1 |
| | > 0.8 | > 0.8 | > 2.4 < 0.6 | 8 | 0 |

Promoter/Luciferase Pilot
Screen of Fermentation
Broth Samples

Promoter-Specific Leads

Figure 53

| Fermentation Broths | Promoter / TIR | | | Number of Specific Leads | |
|---|---|---|---|---|---|
| | G | GM | MTV | Inducers | Inhibitors |
| methanol extracts: 176 total | > 2.0 | < 1.8 | < 1.8 | 0 | |
| | < 0.6 | > 0.8 | > 0.8 | | 0 |
| | < 1.8 | > 2.0 | < 1.8 | 0 | |
| | > 0.8 | < 0.6 | > 0.8 | | 0 |
| | < 1.8 | < 1.8 | > 2.5 | 4 | |
| | > 0.8 | > 0.8 | < 0.6 | | 0 |
| aqueous fractions: 180 total | > 2.0 | < 1.8 | < 1.8 | 0 | |
| | < 0.6 | > 0.8 | > 0.8 | | 0 |
| | < 1.8 | > 1.8 | < 1.8 | 0 | |
| | > 0.8 | < 0.6 | > 0.8 | | 1 |
| | < 1.8 | < 1.8 | > 2.4 | 2 | |
| | > 0.8 | > 0.8 | < 0.6 | | 0 |

G-CSF Concentration in Cell Supernatant
After 48 Hours Incubation

542-Promoter Stimulation Versus Respiratory Inhibition

----- % Inhibition

——— Fold Induction

METHODS OF SPECIFICALLY
TRANSCRIPTIONALLY MODULATING THE
EXPRESSION OF GENE OF INTEREST

This application is a continuation of U.S. Ser. No. 08/267,834, filed Jun. 28, 1994, now U.S. Pat. No. 5,665, 543; which is a continuation of U.S. Ser. No. 08/134,215, filed Oct. 8, 1993, now abandoned; which was a continuation of U.S. Ser. No. 08/013,343, filed Feb. 4, 1993, now abandoned; which was a continuation of the U.S. Ser. No. 07/555,196, filed Jul. 18, 1990, now abandoned; which was a continuation of U.S. Ser. No. 07/382,712, filed Jul. 18, 1989, now abandoned, the contents of which are hereby incorporated by reference into the present disclosure.

BACKGROUND OF THE INVENTION

Throughout this application, various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

The expression of a specific gene can be regulated at any step in the process of producing an active protein. Modulation of total protein activity may occur via transcriptional, transcript-processing, translational or post-translational mechanisms. Transcription may be modulated by altering the rate of transcriptional initiation or the progression of RNA polymerase (28). Transcript-processing may be influenced by circumstances such as the pattern of RNA splicing, the rate of mRNA transport to the cytoplasm or mRNA stability. This invention concerns the use of molecules which act by modulating the in vivo concentration of their target proteins via regulating gene transcription. The functional properties of these chemicals are distinct from previously described molecules which also affect gene transcription.

Researchers have documented the regulation of transcription in bacteria by low molecular weight chemicals (42, 36). Extracellular xenobiotics, amino acids and sugars have been reported to interact directly with an intracellular proteinaceous transcriptional activator or repressor to affect the transcription of specific genes.

Transcriptional regulation is sufficiently different between procaryotic and eucaryotic organisms so that a direct comparison cannot readily be made. Procaryotic cells lack a distinct membrane bound nuclear compartment. The structure and organization of procaryotic DNA elements responsible for initiation of transcription differ markedly from those of eucaryotic cells.

The eucaryotic transcriptional unit is much more complex than its procaryotic counterpart and consists of additional elements which are not found in bacteria. Eucaryotic transcriptional units include enhancers and other cis-acting DNA sequences (30, 19). Procaryotic transcription factors most commonly exhibit a "helix-turn-helix" motif in the DNA binding domain of the protein (29, 37). Eucaryotic transcriptional factors frequently contain a "zinc finger" (37, 12) or a "leucine zipper" (24) in addition to sometimes possessing the "helix-turn-helix" motif (26). Furthermore, several critical mechanisms at the post-transcriptional level such as RNA splicing and polyadenylation are not found in procaryotic systems (21, 35).

In higher eucaryotes, modulation of gene transcription in response to extracellular factors can be regulated in both a temporal and tissue specific manner (22). For example, extracellular factors can exert their effects by directly or indirectly activating or inhibiting transcription factors (22, 28).

Modulators of transcription factors involved in direct regulation of gene expression have been described, and include those extracellular chemicals entering the cell passively and binding with high affinity to their receptor-transcription factors. This class of direct transcriptional modulators include steroid hormones and their analogs, thyroid hormones, retinoic acid, vitamin $D_3$ and its derivatives, and dioxins, a chemical family of polycyclic aromatic hydrocarbons (12, 38, 9).

Dioxins are molecules generally known to modulate transcription, however, dioxins bind to naturally-occurring receptors which respond normally to xenobiotic agents via transcriptionally activating the expression of cytochrome P450part of an enzyme involved in detoxification. Similarly, plants also have naturally occurring receptors to xenobiotics to induce defense pathways. For example, the fungal pathogen *Phytophthora megasperma* induces an anti-fungal compound in soybeans. Such molecules which bind to the ligand binding domains of such naturally occurring receptors are not included on the scope of this invention.

The clinical use of steroid hormones, thyroid hormones, vitamin $D_3$ and their analogs demonstrates that agents which modulate gene transcription can be used for beneficial effects, although these agents can exhibit significant adverse side effects. Obviously, analogs of these agents could have similar clinical utility as their naturally occurring counterparts by binding to the same ligand binding domain of such receptors.

Indirect transcriptional regulation involves one or more signal transduction mechanisms. The regulation typically involves interaction with a receptor, the receptor being part of a multistep intracellular signaling pathway, the pathway ultimately modulating the activity of nuclear transcription factors. This class of indirect transcriptional modulators include polypeptide growth factors such as platelet-derived growth factor, epidermal growth factor, cyclic nucleotide analogs, and mitogenic tumor promoters (18, 1, 2).

It is well documented that a large number of chemicals, both organic and inorganic, e.g. metal ions, can non-specifically modulate transcription.

Researchers have used nucleotide analogs in methods to modulate transcription. The mechanism involves incorporating nucleotide analogs into nascent mRNA or non-specifically blocking mRNA synthesis. Similarly, researchers have used alkylating agents, e.g. cyclophosphamide, or intercalating agents, e.g. doxorubicin, to non-specifically inhibit transcription.

Moreover, chemical inhibitors of hydroxymethyl-glutaryl CoA reductase, e.g. lovastatin, are known to modulate transcription by indirectly increasing expression of hepatic low density lipoprotein receptors as a consequence of lowered cholesterol levels.

Signal effector type molecules such as cyclic AMP, diacylglycerol, and their analogs are known to non-specifically regulate transcription by acting as part of a multistep protein kinase cascade reaction. These signal effector type molecules bind to domains on proteins which are thus subject to normal physiological regulation by low molecular weight ligands (10, 39).

The specific use of sterol regulatory elements from the LDL receptor gene to control expression of a reporter gene has recently been documented in PCT/US88/10095. One aspect of PCT/US88/10095 deals with the use of specific sterol regulatory elements coupled to a reporter as a means to screen for drugs capable of stimulating cells to synthesize the LDL receptor. PCT/US88/10095 describes neither the concept of simultaneously screening large numbers of chemicals against multiple target genes nor the existence of transcriptional modulators which (a) do not naturally occur in the cell, (b) specifically transcriptionally modulate expression of the gene-of-interest, and (c) bind to DNA or RNA or bind to a protein through a domain of such protein which is not a ligand binding domain of a receptor which naturally occurs in the cell, the binding of a ligand to which ligand binding domain is normally associated with the defined physiological effect. The main focus of PCT/US88/10095 is the use of the sterol regulatory elements from the LDL receptor as a means to inhibit expression of toxic recombinant biologicals.

The use of molecules to specifically modulate transcription of a gene-of-interest as described herein has not previously been reported and its use will bring surprise since available literature does not propose the use of a molecule, as described, in a method to specifically modulate transcription. Instead, the available literature has reported methods which define domains of transcriptional regulating elements of a gene-of-interest.

Further, the practice of using a reporter gene to analyze nucleotide sequences which regulate transcription of a gene-of-interest is well documented. The demonstrated utility of a reporter gene is in its ability to define domains of transcriptional regulatory elements of a gene-of-interest. Reporter genes which express proteins, e.g. luciferase, are widely utilized in such studies. Luciferases expressed by the North American firefly, *Photinus pyralis* and the bacterium, *Vibrio fischeri* were first described as transcriptional reporters in 1985 (8, 11)

A method to define domains of transcriptional regulating elements of a gene-of-interest typically has also involved use of phorbol esters, cyclic nucleotide analogs, concanavalin A, or steroids, molecules which are commonly known as transcriptional modulators. However, available literature shows that researchers have not considered using a transcription screen to identify specific transcriptional modulators. Apparently, success would be unlikely in doing so, however, we have demonstrated herein that this is not the case.

There is utility in developing the method of transcriptional modulation of a gene-of-interest by using such molecule as described herein. This method will allow the development of novel pharmaceuticals and circumvent many of the problems associated with the therapeutic use of recombinant biological factors.

Problems associated with the therapeutic use of recombinant biological factors include the technical difficulties of large scale protein purification, the high costs of protein production, the limited shelf-life of most proteins and in some cases a short biological half-life of the administered protein in the organism. Additionally, therapeutic delivery of proteins normally requires injection and frequently induces an immune reaction in situations where chronic administration is required. The method described herein provides a means of up-regulating the expression of proteins, e.g. membrane receptors, which are not readily amenable to administration as injectable biologicals.

Furthermore, chemical molecules specifically regulating the activity of one member of a group of closely related proteins are difficult to produce. Molecules, structurally related at the protein level, may possess distinct regulatory elements at the DNA level which control their expression. Thus, molecules such as the chemical transcriptional modulators defined herein can provide a greater opportunity for specifically modulating the activity of structurally related proteins. One example is the ras oncogene family, where the H-, N- and K-ras proteins are highly related but wherein the three genes have distinct structures.

Finally, the molecules described herein may also serve to mimic normal physiological response mechanisms, typically involving the coordinated expression of one or more groups of functionally related genes. Therefore, determining whether a molecule can specifically transcriptionally modulate the expression of a gene-of-interest and the ultimate clinical use of the molecule provides a therapeutic advantage over the use of single recombinant biologicals, or drugs which bind directly to the final target protein encoded by the gene-of-interest.

SUMMARY OF THE INVENTION

The present invention provides a method of transcriptionally modulating the expression of a gene-of-interest, the expression of which is associated with a defined physiological or pathological effect within a multicellular organism. The method comprises contacting a cell which is capable of expressing the gene with an amount of a molecule effective to transcriptionally modulate expression of the gene and thereby affect the level of the protein encoded by the gene which is expressed by the cell.

Molecules useful in the practice of the invention are characterized as follows (a) do not naturally occur in the cell, (b) specifically transcriptionally modulate expression of the gene-of-interest, and (c) bind to DNA or RNA or bind to a protein through a domain of such protein which is not a ligand binding domain of a receptor which naturally occurs in the cells, the binding of a ligand to which ligand binding domain is normally associated with the defined physiological or pathological effect.

Additionally, this invention provides a method of determining whether a molecule, not previously known to be a modulator of protein biosynthesis, is capable of transcriptionally modulating the expression of a gene-of-interest. The method comprises contacting a sample which contains a predefined number of cells with a predetermined amount of a molecule to be tested. Each such cell comprises DNA consisting essentially of (i) a modulatable transcriptional regulatory sequence of the gene-of-interest, (ii) a promoter of the gene-of-interest, and (iii) a reporter gene which expresses a polypeptide capable of producing a detactable signal, coupled to, and under the control of, the promoter, and the contacting is carried out under conditions such that the molecule, if capable of acting as a transcriptional modulator of the gene-of-interest, causes a measurable detectable signal to be produced by the polypeptide expressed by the reporter gene and the amount of the signal produced may be quantitatively determined. The amount of produced signal so determined is compared with the amount of produced signal detected in the absence of any molecule being tested or upon contacting the sample with any other molecule so as to thereby identify the molecule as one which causes a change in the detectable signal produced by the polypeptide expressed by the reporter gene and thus identify the molecule as a molecule capable of transcriptionally modulating the expression of the gene-of-interest.

The present invention still further provides a method for transcriptionally modulating in a multicellular organism the expression of a gene-of-interest, the expression of which is associated with a defined physiological or pathological effect in the organism. The method comprises administering to the organism an amount of a molecule effective to transcriptionally modulate expression of the gene and thus affect the defined physiological or pathological effect. A molecule useful in the method: (a) does not naturally occur in the organism, (b) specifically transcriptionally modulates expression of the gene-of-interest, and (c) binds to DNA or RNA or binds to a protein through a domain of such protein which is not a ligand binding domain of a receptor which naturally occurs in the organism, the binding of a ligand to which ligand binding domain is normally associated with the defined physiological or pathological effect.

This invention provides a method for enhancing the expression of human growth hormone by a cell which (i) comprises DNA encoding, and (ii) is capable of expressing, human growth hormone. The method comprises contacting the cell with an amount of a molecule having the structure:

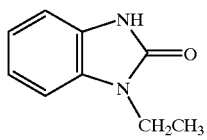

effective to enhance the expression of human growth hormone by the cell.

Additionally, this invention provides a method of increasing the growth of a human being who (i) comprises DNA encoding, and (ii) is capable of expressing, human growth hormone, comprising administering to the human being an amount of a molecule having the structure:

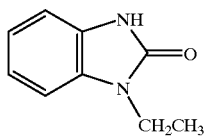

effective to enhance expression of human growth hormone by, and thus growth of, the human being.

The invention also provides a method for enhancing the expression of human growth hormone by a cell which (i) comprises DNA encoding, and (ii) is capable of expressing, human growth hormone, comprising contacting the cell with an amount of a molecule having the structure:

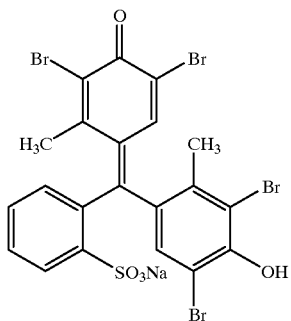

effective to enhance the expression of human growth hormone by the cell.

Another provision of the present invention concerns a method of increasing the growth of a human being who (i) comprises DNA encoding, and (ii) is capable of expressing, human growth hormone. The method comprises administering to the human being an amount of a molecule having the structure:

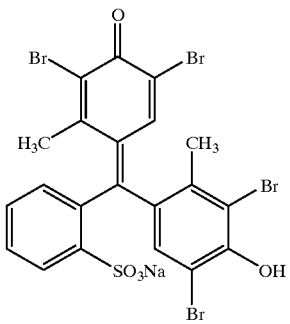

effective to enhance expression of human growth hormone by, and thus growth of, the human being.

This invention also concerns a method for enhancing the expression of human growth hormone by a cell which (i) comprises DNA encoding, and (ii) is capable of expressing, human growth hormone, comprising contacting the cell with an amount of a molecule having the structure:

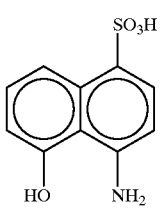

effective to enhance the expression of human growth hormone by the cell.

Further, this invention provides a method of increasing the growth of a human being who (i) comprises DNA encoding, and (ii) is capable of expressing, human growth hormone, comprising administering to the human being an amount of a molecule having the structure:

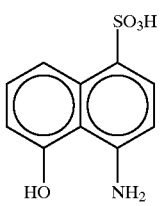

effective to enhance expression of human growth hormone by, and thus growth of, the human being.

Additionally, this invention concerns a method for enhancing the expression of human growth hormone by a cell which (i) comprises DNA encoding, and (ii) is capable of expressing, human growth hormone, comprising contacting the cell with an amount of a molecule having the structure:

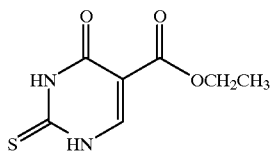

effective to enhance the expression of human growth hormone by the cell.

Additionally, the invention provides a method of increasing the growth of a human being who (i) comprises DNA encoding, and (ii) is capable of expressing, human growth hormone. The method comprises administering to the human being an amount of a molecule having the structure:

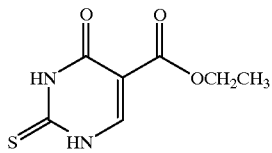

effective to enhance expression of human growth hormone by, and thus growth of, the human being.

Further, the invention provides another method for enhancing the expression of human growth hormone by a cell which (i) comprises DNA encoding, and (ii) is capable of expressing, human growth hormone. The method comprises contacting the cell with an amount of a molecule having the structure:

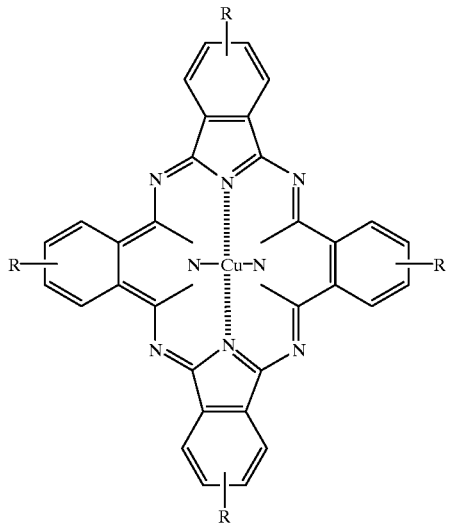

effective to enhance the expression of human growth hormone by the cell.

Additionally, the invention provides a method of increasing the growth of a human being who (i) comprises DNA encoding, and (ii) is capable of expressing, human growth hormone, comprising administering to the human being an amount of a molecule having the structure:

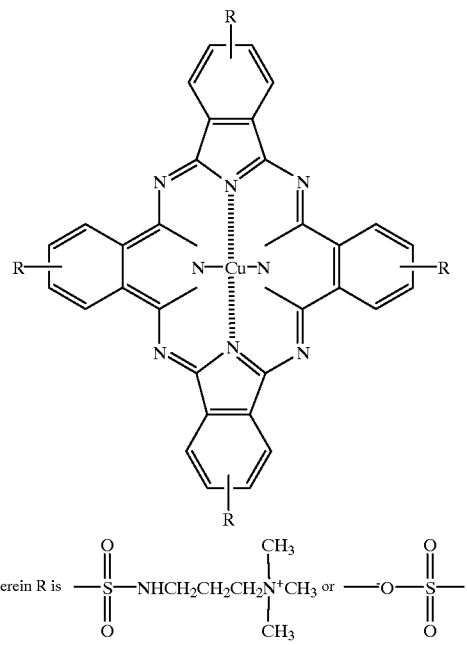

effective to enhance expression of human growth hormone by, and thus growth of, the human being.

Further, this invention provides a method for enhancing the expression of human growth hormone by a cell which (i) comprises DNA encoding, and (ii) is capable of expressing, human growth hormone. The method comprises contacting the cell with an amount of a molecule having the structure:

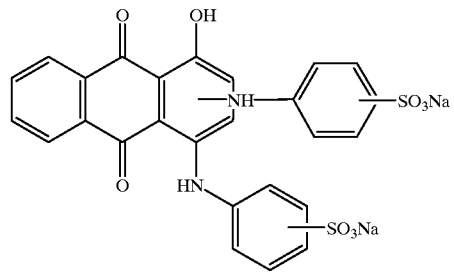

effective to enhance the expression of human growth hormone by the cell.

Further more, this invention provides a method of increasing the growth of a human being who (i) comprises DNA encoding, and (ii) is capable of expressing, human growth hormone. The method comprises administering to the human being an amount of a molecule having the structure:

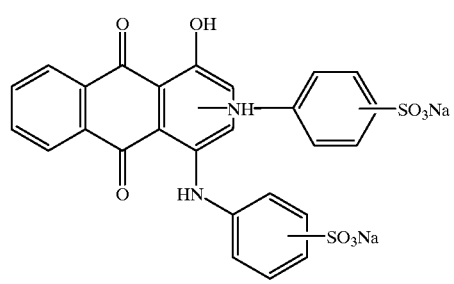

effective to enhance expression of human growth hormone by, and thus growth of, the human being.

The present invention provides a method for enhancing the expression of G-CSF by a cell which (i) comprises DNA encoding, and (ii) is capable of expressing, G-CSF. The method comprises contacting the cell with an amount of a molecule having the structure:

effective to enhance the expression of G-CSF by the cell.

The present invention also provides a method for increasing the formation of neutrophils in a human being who (i) comprises DNA encoding, and (ii) is capable of expressing, G-CSF. The method comprises administering to the human being an amount of a molecule having the structure:

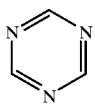

effective to enhance the expression of GCSF by, and thus increase the formation of neutrophils in, the human being.

The present invention also provides a method for enhancing the expression of G-CSF by a cell which (i) comprises DNA encoding, and (ii) is capable of expressing, G-CSF. The method comprises contacting the cell with an amount of a molecule having the structure:

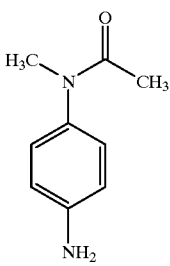

effective to enhance the expression of G-CSF by the cell.

Additionally, the invention provides a method of increasing the formation of neutrophils in a human being who (i) comprises DNA encoding, and (ii) is capable of expressing, G-CSF. The method comprises administering to the human being an amount of a molecule having the structure:

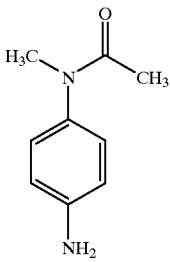

effective to enhance expression of G-CSF by, and thus increase the formation of neutrophils in, the human being.

Further, the invention provides another method for enhancing the expression of G-CSF by a cell which (i) comprises DNA encoding, and (ii) is capable of expressing, G-CSF. The method comprises contacting the cell with an amount of a molecule having the structure:

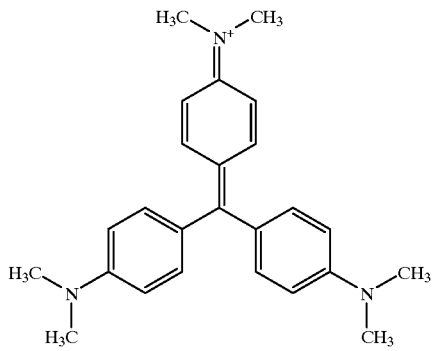

effective to enhance the expression of G-CSF by the cell.

The present invention provides another method of increasing the formation of neutrophils in a human being who (i) comprises DNA encoding, and (ii) is capable of expressing, G-CSF. The method comprises administering to the human being an amount of a molecule having the structure:

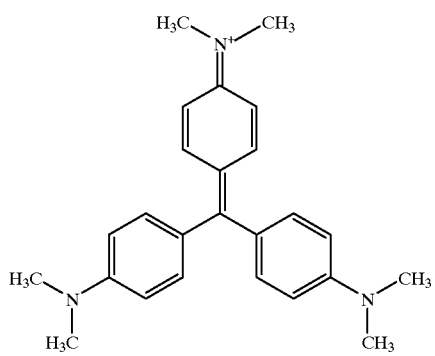

effective to enhance expression of G-CSF by, and thus increase the formation of neutrophils in, the human being.

The invention also concerns a method for enhancing the expression of G-CSF by a cell which (i) comprises DNA encoding, and (ii) is capable of expressing, G-CSF comprising contacting the cell with an amount of a molecule having the structure:

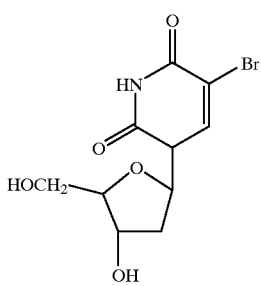

effective to enhance the expression of G-CSF by the cell.

Additionally, the invention concerns a method of increasing the formation of neutrophils in a human being who (i) comprises DNA encoding, and (ii) is capable of expressing, G-CSF, comprising administering to the human being an amount of a molecule having the structure:

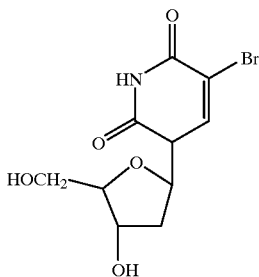

effective to enhance expression of G-CSF by, and thus increases the formation of neutrophils in, the human being.

This invention further concerns a method for enhancing the expression of G-CSF by a cell which (i) comprises DNA encoding, and (ii) is capable of expressing G-CSF. The method comprises contacting the cell with an amount of a molecule having the structure:

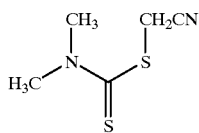

effective to enhance the expression of G-CSF by the cell.

Further the invention provides a method of increasing the formation of neutrophils in a human being who (i) comprises DNA encoding, and (ii) is capable of expressing, G-CSF, comprising administering to the human being an amount of a molecule having the structure:

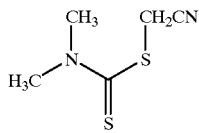

effective to enhance expression of G-CSF by, and thus increase the formation of neutrophils in, the human being.

Additionally, the present invention concerns a method for enhancing the expression of G-CSF by a cell which (i) comprises DNA encoding, and (ii) is capable of expressing, G-CSF, comprising contacting the cell with an amount of a molecule having the structure:

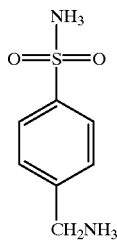

effective to enhance the expression of G-CSF by the cell.

The invention further concerns a method of increasing the formation of neutrophils in a human being who (i) comprises DNA encoding, and (ii) is capable of expressing G-CSF wherein the method comprises administering to the human being an amount of a molecule having the structure:

effective to enhance expression of G-CSF by, and thus increase the formation of neutrophils in, the human being.

Also, the invention provides a method for enhancing the expression of G-CSF by a cell which (i) comprises DNA encoding, and (ii) is capable of expressing G-CSF. The method comprises contacting the cell with an amount of a molecule having the structure:

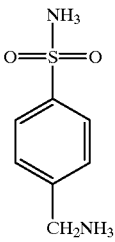

effective to enhance the expression of G-CSF by the cell.

The invention additionally concerns a method of increasing the formation of neutrophils in a human being who (i) comprises DNA encoding, and (ii) is capable of expressing, G-CSF, wherein the method comprises administering to the human being an amount of a molecule having the structure:

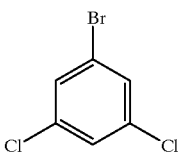

effective to enhance expression of G-CSF by, and thus increase the formation of neutrophils in, the human being.

Another provision of the present invention is a method for enhancing the expression of G-CSF by a cell which (i) comprises DNA encoding, and (ii) is capable of expressing G-CSF. The method comprises contacting the cell with an amount of a molecule having the structure:

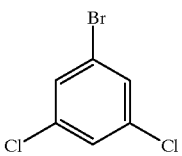

effective to enhance the expression of G-CSF by the cell.

Additionally, the invention provides a method of increasing the formation of neutrophils in a human being who (i) comprises DNA encoding, and (ii) is capable of expressing G-CSF. The method comprises administering to the human being an amount of a molecule having the structure:

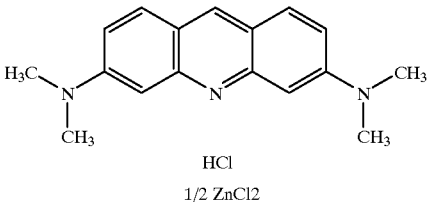

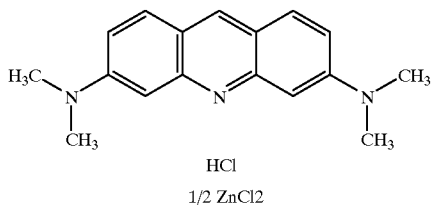

effective to enhance expression of G-CSF by, and thus increase the formation of neutrophils in the human being.

The present invention provides another method for enhancing the expression of G-CSF by a cell which (i) comprises DNA encoding, and (ii) is capable of expressing, G-CSF. The method comprises contacting the cell with an amount of a molecule having the structure:

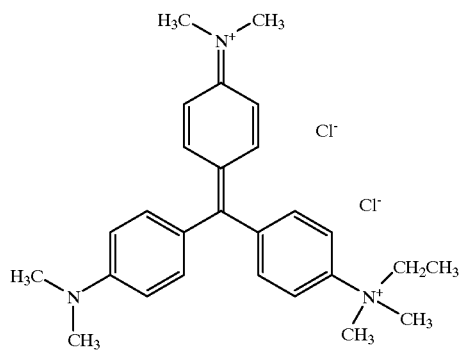

effective to enhance the expression of G-CSF by the cell.

Further, the present invention concerns a method of increasing the formation of neutrophils in a human being who (i) comprises DNA encoding, and (ii) is capable of expressing G-CSF. The method comprises administering to the human being an amount of a molecule having the structure:

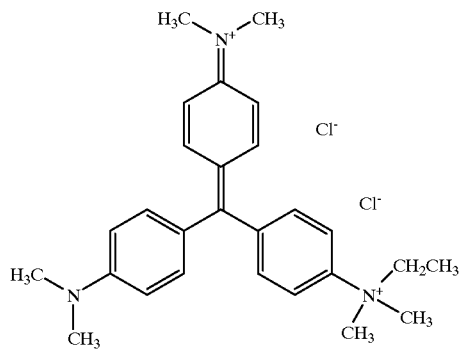

effective to enhance expression of G-CSF by, and thus increase the formation of neutrophils in, the human being.

This invention also concerns a method of decreasing the expression of G-CSF by a cell which (i) comprises DNA encoding, and (ii) is capable of expressing, G-CSF. The method comprises contacting the cell with an amount of a molecule having the structure:

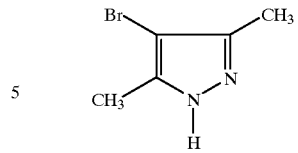

effective to decrease the expression of G-CSF by the cell.

Additionally, this invention provides a method of decreasing the formation of neutrophils and affecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

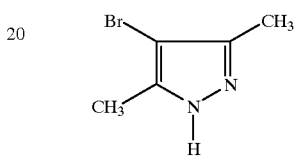

effective to decrease expression of G-CSF by, and thus decrease the formation and affect the metabolic functions of neutrophils in, the human being.

Further, the invention also concerns a method of decreasing the expression of G-CSF by a cell which (i) comprises DNA encoding, and (ii) is capable of expressing, G-CSF. The method comprises contacting the cell with an amount of a molecule having the structure:

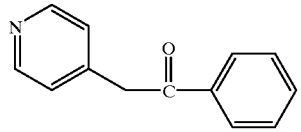

effective to decrease the expression of G-CSF by the cell.

Additionally, this invention provides a method of decreasing the formation of neutrophils and affecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

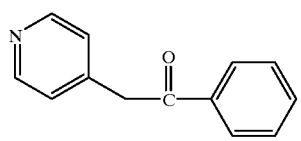

effective to decrease expression of G-CSF by, and thus decrease the formation and affect the metabolic functions of neutrophils in, the human being.

The invention further provides a method of decreasing the expression of G-CSF by a cell which (i) comprises DNA encoding, and (ii) is capable of expressing, G-CSF. The method comprises contacting the cell with an amount of a molecule having the structure:

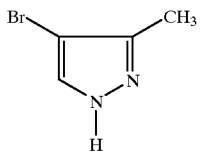

effective to decrease the expression of G-CSF by the cell.

Additionally, this invention provides a method of decreasing the formation of neutrophils and effecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

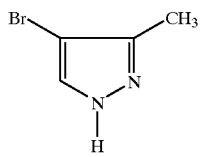

effective to decrease expression of G-CSF by, and thus decrease the formation and affect the metabolic functions of neutrophils in, the human being.

Further, the present invention a method of decreasing the expression of G-CSF by a cell which (i) comprises DNA encoding, and (ii) is capable of expressing, G-CSF. The method comprises contacting the cell with an amount of a molecule having the structure:

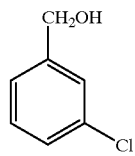

effective to decrease the expression of G-CSF by the cell.

Additionally, this invention provides a method of decreasing the formation of neutrophils and affecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

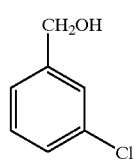

effective to decrease expression of G-CSF by, and thus decrease the formation and affect the metabolic functions of neutrophils in, the human being.

The present invention further provides a method of decreasing the expression of G-CSF by a cell which (i) comprises DNA encoding, and (ii) is capable of expressing, G-CSF. The method comprises contacting the cell with an amount of a molecule having the structure:

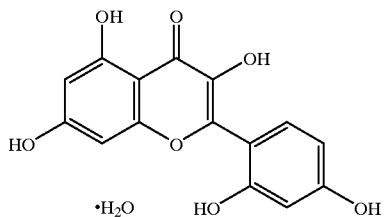

effective to decrease the expression of G-CSF by the cell.

Further still the invention provides a method of decreasing the formation of neutrophils and affecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

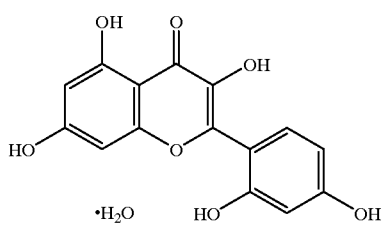

effective to decrease expression of G-CSF by, and thus decrease the formation and affect the metabolic functions of neutrophils in, the human being.

The present invention also concerns a method of decreasing the expression of G-CSF by a cell which (i) comprises DNA encoding, and (ii) is capable of expressing, G-CSF. The method comprises contacting the cell with an amount of a molecule having the structure:

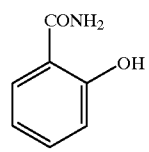

effective to decrease the expression of G-CSF by the cell.

Additionally, the present invention concerns a method of decreasing the formation of neutrophils and affecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

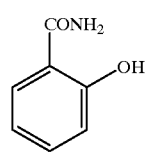

effective to decrease expression of G-CSF by, and thus decrease the formation and affect the metabolic functions of neutrophils in, the human being.

The present invention also concerns a method of decreasing the expression of G-CSF by a cell which (i) comprises DNA encoding, and (ii) is capable of expressing, G-CSF. The method comprises contacting the cell with an amount of a molecule having the structure:

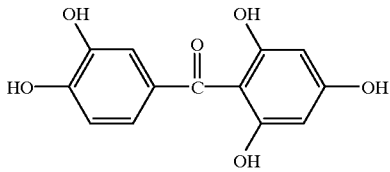

effective to decrease the expression of G-CSF by the cell.

Further, the invention concerns a method of decreasing the formation of neutrophils and affecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

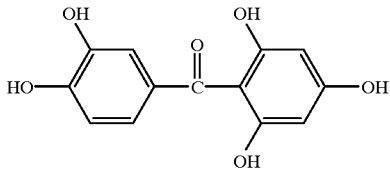

effective to decrease expression of G-CSF by, and thus decrease the formation and affect the metabolic functions of neutrophils in, the human being.

Moreover, the invention provides a method of decreasing the expression of a mammary tumor virus by a cell which (i) comprises DNA encoding, and (ii) is capable of expressing, a mammary tumor virus. The method comprises contacting the cell with an amount of a molecule having the structure:

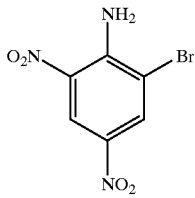

effective to decrease the expression of a mammary tumor virus by the cell.

Finally, the invention also provides a method of suppressing the proliferation of a mammary tumor virus in a subject who (i) comprises DNA encoding, and (ii) is capable of expressing, a mammary tumor virus, comprising administering to the subject an amount of a molecule having the structure:

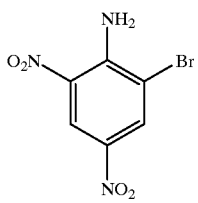

effective to suppress the proliferation of a mammary tumor virus in the subject.

BRIEF DESCRIPTION OF THE FIGURES

FIG. 11a provides the nucleotide sequences of six oligonucletides, pUV-1 through pUV-6, which were annealed, ligated, and inserted into the SalI/EcoR1 sites of the plasmid pTZ18R.

FIG. 15 provides the nucleotide sequences of oligos 1–4 used for the construction of a synthetic HSV-Thymidine Kinase promoter and provides a diagrammatic representation of the HSV-TK promoter.

FIG. 21 provides the nucleotide sequence of oligonucleotides 1 through 4 and provides a diagrammatic representation of GM-CSF upstream sequences fused with the ATG of the coding region of the luciferase gene from the firefly, *Photinus pyralis*.

FIG. 22 is a diagrammatic representation of the construction of the plasmids pGMLS102 and pGMLS103 from plasmid pUV 102 and 0.7 kb fragment from pGM-2 and from pUV 103 and a 0.7 kb fragment from pGM-2, respectively.

Reprobing with beta-actin was used to normalize for the amount of mRNA that had been loaded onto the gel.

FIG. 47 illustrates a dose response analysis of chemicals #80, #670, and #1780 using the G-CSF reporter cell line G21. The amount of luciferase expression is indicated in arbitrary units.

Figure 48:
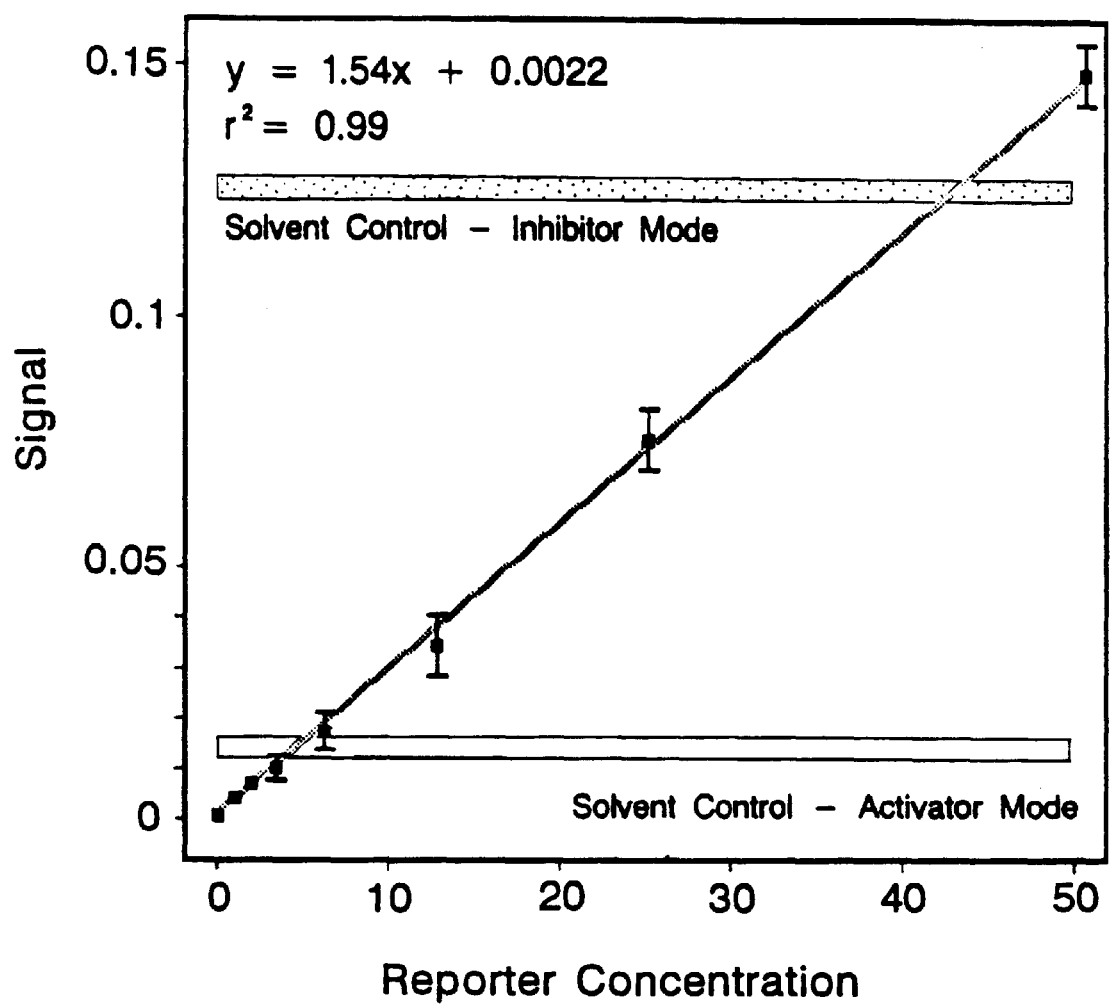

FIG. 48 illustrates the linear dependance of the bioluminescent signal (in arbitrary luminometer units) from the luciferase reporter concentration (1,280 fg luciferase correspond to 50 relative reporter concentration units).

Figure 49:
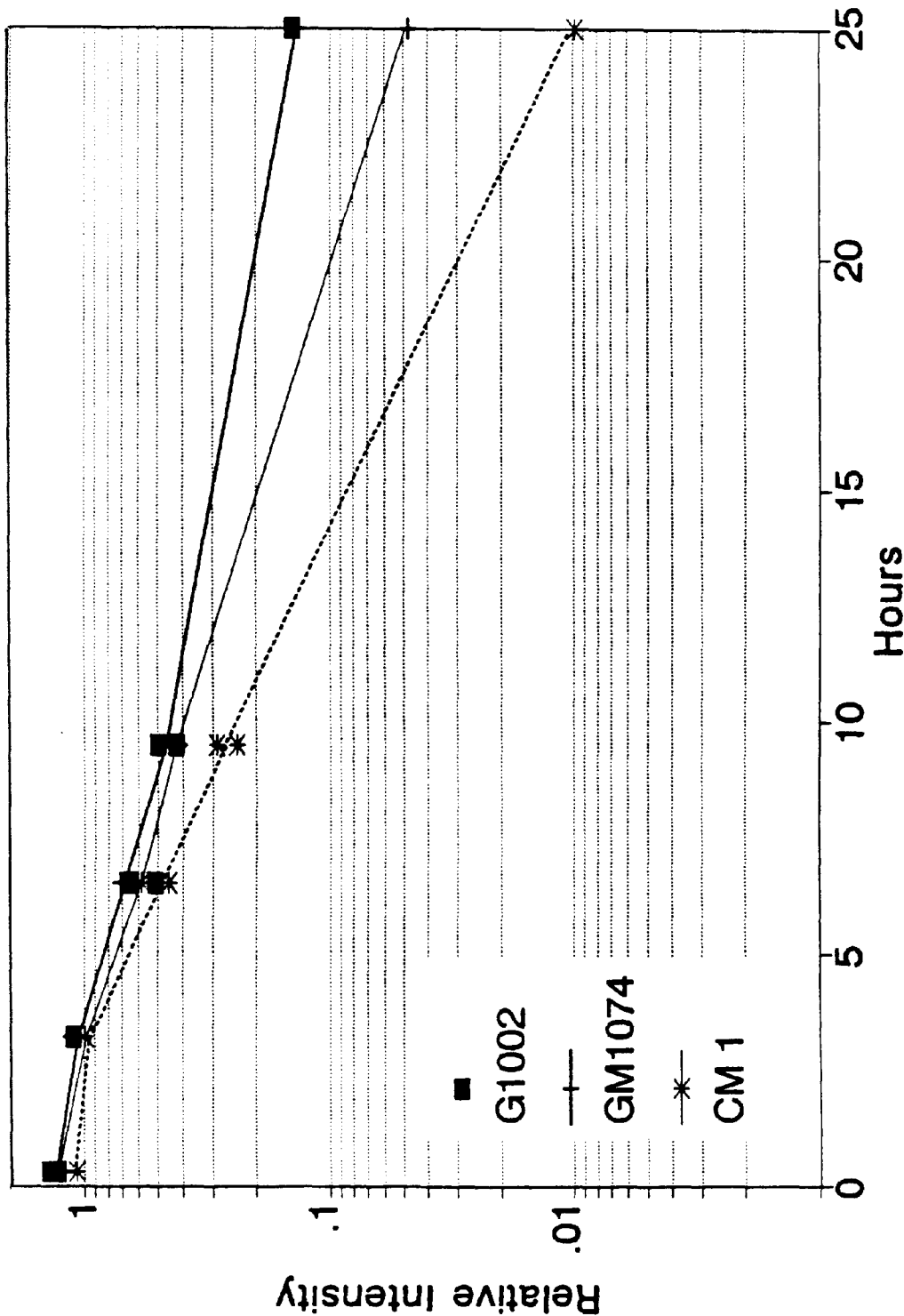

FIG. 49 illustrates the time course of bioluminescent signal decay after addition of Actinomycin D to the cell clones G 1002, GM 1074 and CM 1. Time in hours is plotted against the logarithm of the ratio of the bioluminescent signal generated by Actinomycin D—treated cells over the signal of untreated control cells.

Figure 50:
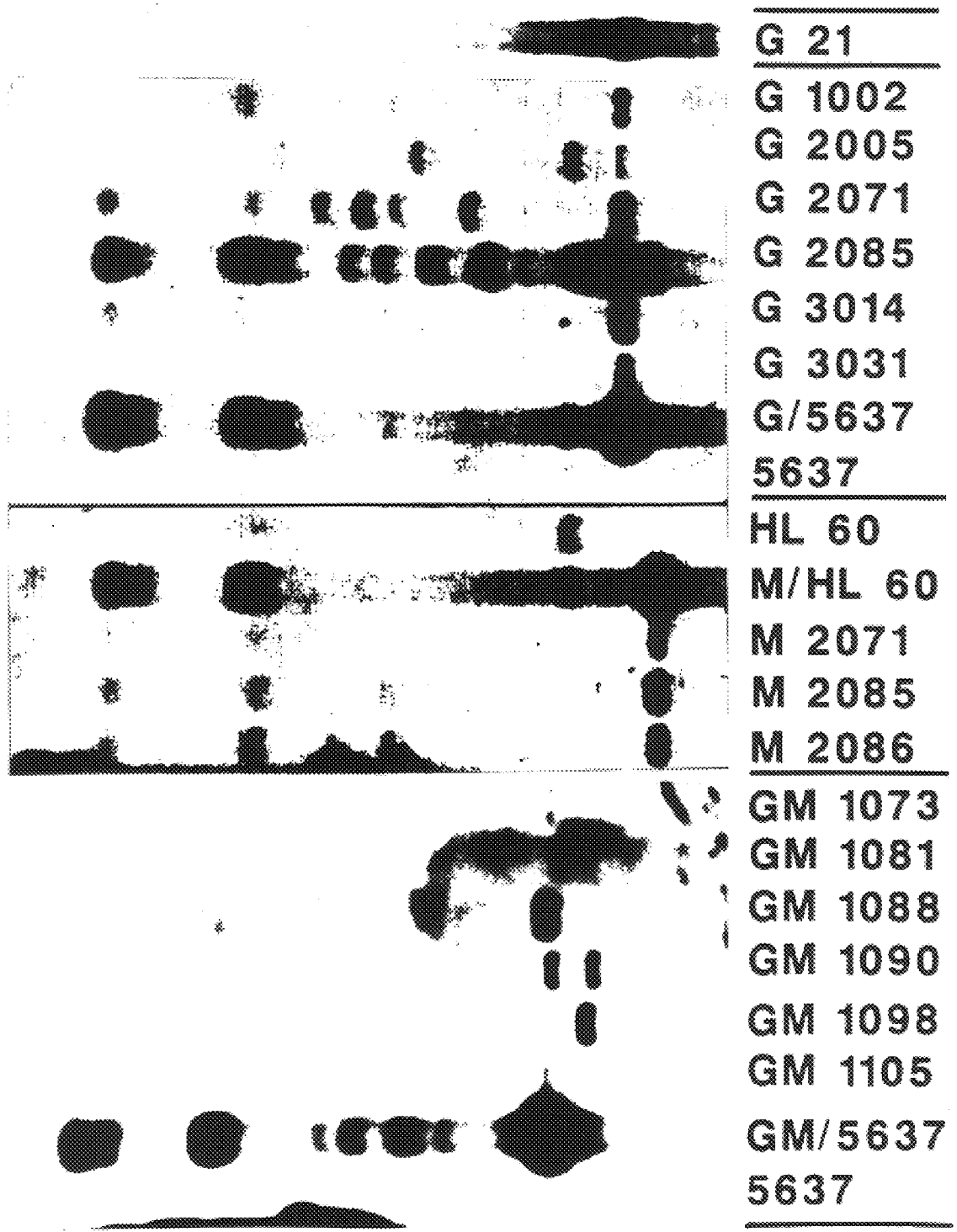

FIG. 50 is an autoradiograph of a Southern blot illustrating the correct integration of luciferase fusion constructs containing the G-CSF, M-CSF and GM-CSF promoters, respectively, into the genomes of 5637 cells (G- and GM-CSF) and HL 60 cells (M-CSF). Lanes designated 5637 and HL 60 had been loaded with DNA preparations from the parental cell lines not containing the luciferase constructs (negative controls). Lanes labeled G/5637, GM/5637 and M/HL 60 had been loaded with the same DNA preparations with the addition of the purified plasmid preparations, which had been used for the original transfections (positive controls). The two low-molecular-weight bands appearing in almost all lanes except for the negative control lanes are derived from non-specific cross-hybridizing sequences contained in the probe.

FIG. 51 illustrates a dose response analysis of DMSO, methanol and ethanol using the reporter cell lines M 10, G 2005 and GM 1105. The level of luciferase expression of solvent-treated cells expressed in percent of that of untreated control cells is plotted against solvent concentration.

FIG. 52 is a summary of the number of lead samples obtained in a luciferase expression screen of Actinomyces fermentation broth samples for modulation of the G-CSF, GM-CSF and MMTV promoters. "TIR" stands for "Transcriptional Induction/Inhibition Ratio" and represents the ratio of luciferase expression generated by a test sample treated cells over that of control cells treated by solvent alone.

FIG. 53 is a summary of those lead samples listed in FIG. 52, which specifically modulate one promoter only according to the TIR criteria indicated.

Figure 54:
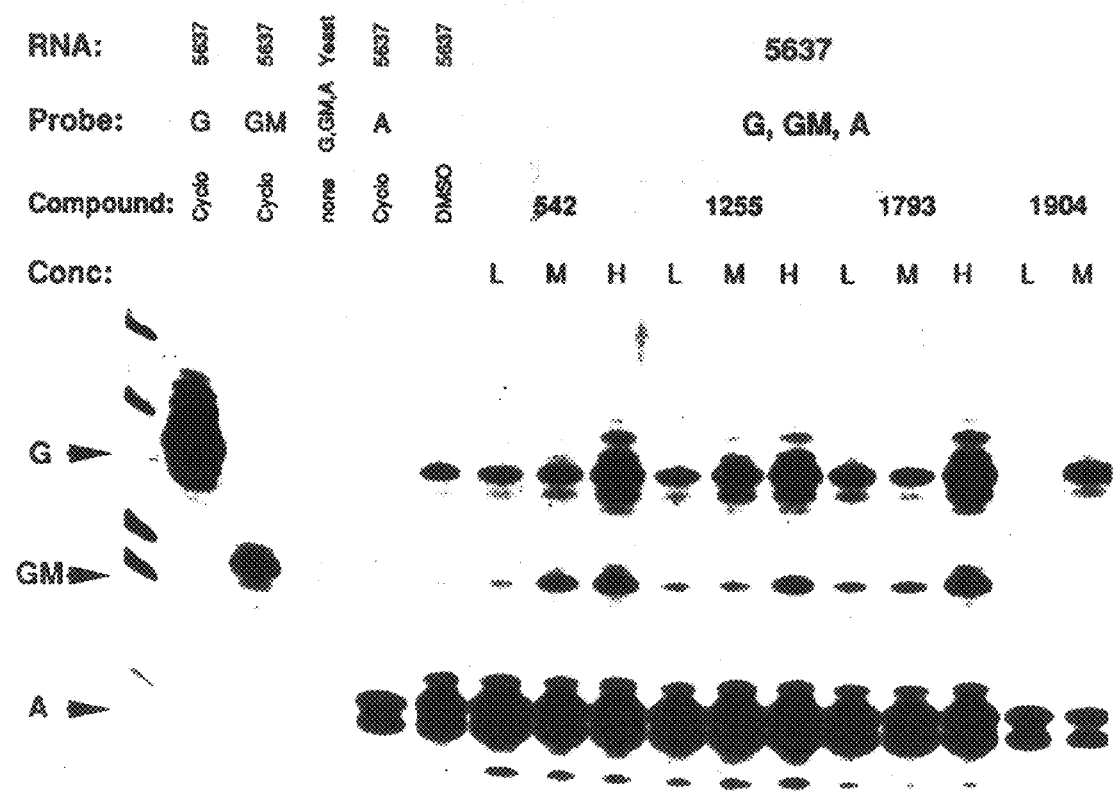

FIG. 54 is an autoradiograph of a polyacrylamide gel illustrating an S1 nuclease protection analysis of increased mRNA production by the human bladder carcinoma cell line 5637 in response to lead chemicals #542, #1255, #1793 and #1904. "RNA" indicates the sources of the RNA preparations used in individual lanes. "Probe" indicates the mRNA-specificities of probes used in individual lanes. "Compound" lists the compounds with which the 5637 cells were treated prior to RNA extraction and loading on individual gel lanes ("Cyclo" means cycloheximide). "Conc" indicates three different compound concentrations used in the experiment (L=low, M=medium, H=high). G, GM and A indicate the correct sizes of G-CSF-, GM-CSF- and Actin-specific nuclease-protected mRNA/Probe hybrids.

Figure 55:
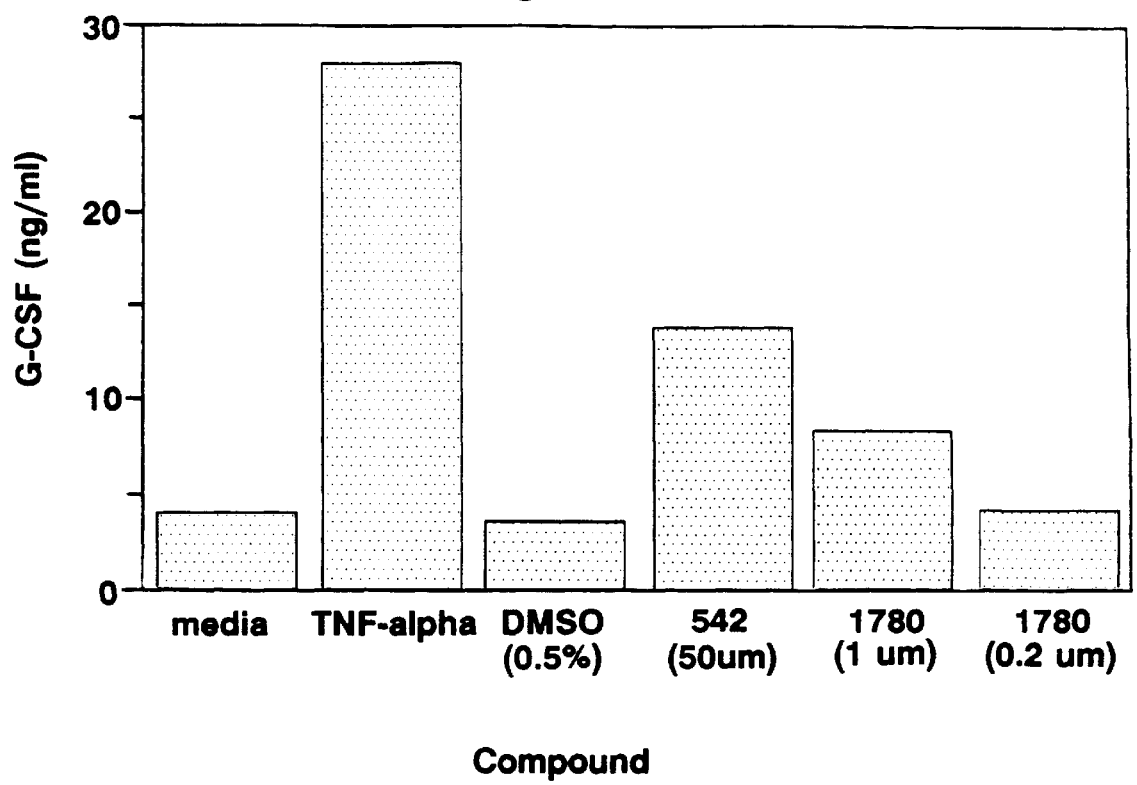

FIG. 55 is a bar graph illustrating increased G-CSF secretion by 5637 cells treated for 48 hours in serum-containing media with the samples indicated on the abscissa. TNF-alpha was used at 5 ng/ml. Chemicals #542 and #1780 were used at 50 uM or 1 uM and 0.2 uM final concentration, respectively. Both chemicals were used in DMSO at a final concentration of 0.5%. The ordinate indicates the concentration of G-CSF secreted into 5 ml of serum-containing media by 25 square cm of confluent 5637 cells.

Figure 56:
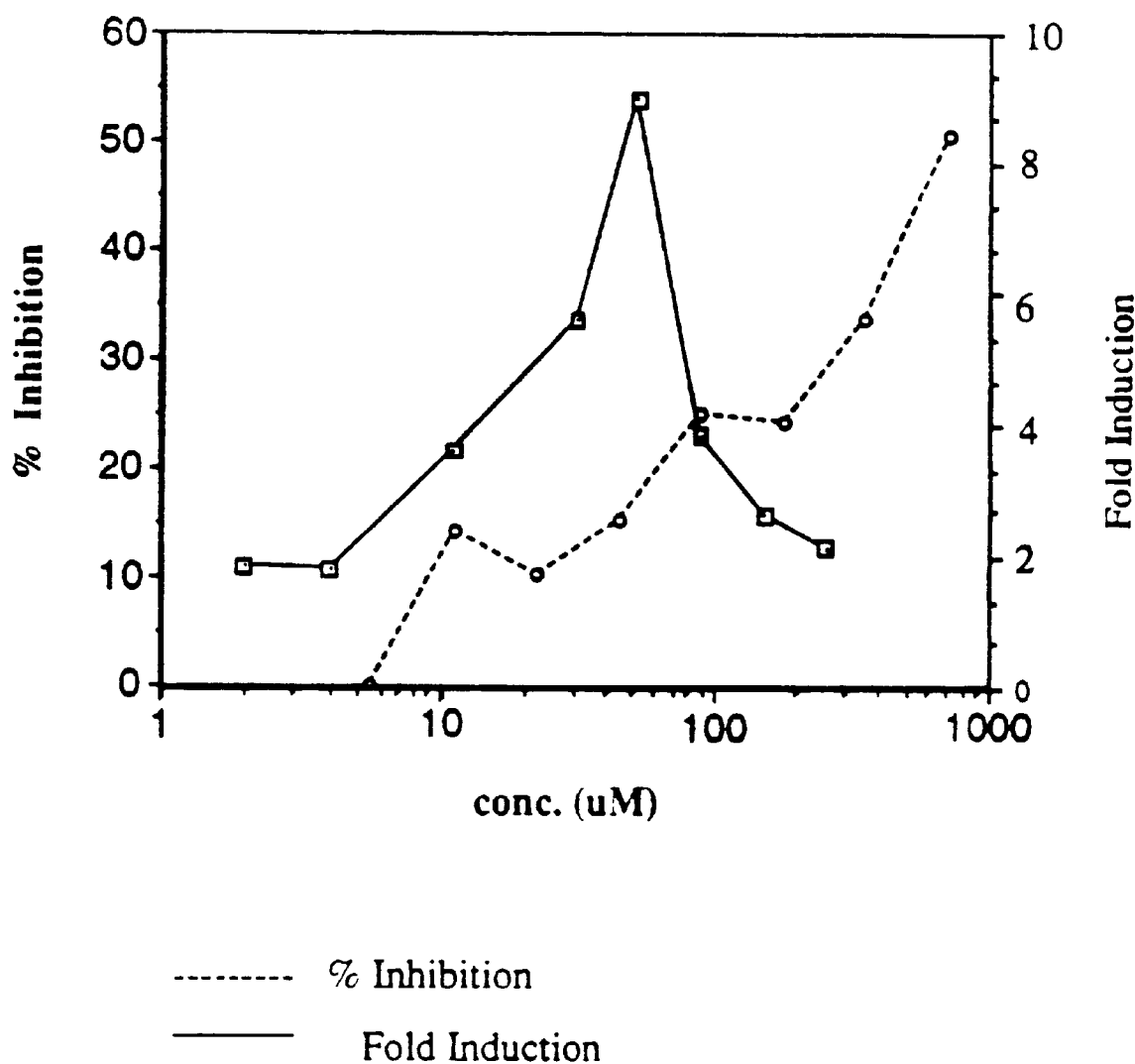

FIG. 56 illustrates a dose response analysis of chemical #542 using the G-CSF reporter cell line G 21 (solid line) and the MTT respiratory inhibition cytotoxicity assay (dotted line). Respiratory inhibition in percent of untreated control cells (Ordinate, left scale) and luciferase expression of #542—treated over solvent-treated cells (ordinate, right scale) are plotted against #542 concentration (abscissa).

DETAILED DESCRIPTION OF THE INVENTION

The present invention provides a method of transcriptionally modulating the expression of a homologous gene-of-interest, the expression of which is associated with a defined physiological or pathological effect within a multicellular organism. The method comprises contacting a cell which is capable of expressing the gene with an amount of a molecule effective to transcriptionally modulate the expression of the gene. Modulating the expression of the gene affects the level of the protein encoded by the gene which is expressed by the cell. As used herein a homologous gene-of-interest means a gene which is naturally associated with an organism or virus encoding and expressing the gene. Therefore, this definition would not include a synthetic or recombinant gene constructed by genetic engineering methods so as to position the gene-of-interest under the control of a heterologous promoter.

The term "physiological effect" as used herein is defined as an effect characteristic of, or appropriate to, an organism's healthy or normal functioning. Further, the term "pathological effect" as used herein is defined as an effect altered or caused by disease.

Molecules useful in the practice of the invention are characterized as follows (a) do not naturally occur in the cell, (b) specifically transcriptionally modulate expression of the gene-of-interest, and (c) bind to DNA or RNA or bind to a protein through a domain of such protein which is not a ligand binding domain of a receptor which naturally occurs in the cell, the binding of a ligand to which ligand binding domain is normally associated with the defined physiological or pathological effect.

In one example of this invention, the molecule would not occur naturally in any cell of a higher eucaryotic organism. In another example of this invention the molecule would not occur naturally in any cell, e.g. minerals. In yet another example, the molecule would not occur naturally, e.g. synthetic molecules.

The phrase "specifically transcriptionally modulate expression of the gene-of-interest" as used herein means modulating the expression of the gene-of-interest without modulating the expression of other genes in the cell in a way which would cause an adverse effect on (a) an organism containing the cell in the case where the cell is within the organism or (b) the growth or the culturing of the cell, in the case where the cell is being grown or cultured to make a product where the amount of product produced is associated with expression of the gene-of-interest. However, within this definition where the drug is used to treat, for example, parasitic infection, drug application is intended to cause an adverse effect on the cells of the parasite (which may contain the gene-of-interest), but not on the cells of the host organism. In this context, a gene-of-interest may constitute a single gene or a limited number of genes whose expression can be functionally coordinated. One example of coordinate gene regulation is exhibited by the physiological growth modulators termed the transforming growth factor-β family of polypeptides (TGF-βs) (90). TGF-βs control the extracellular matrix (ECM) by; (1) increasing expression of the genes encoding ECM polypeptides, e.g. collagen, fibronectin and osteopontin; (2) increasing expression of receptors for the ECM, e.g. the integrins; and (3) increasing expression of protease inhibitors (e.g. TIMP and PAI-I) while decreasing expression of secreted proteases (e.g. collagenase and stromelysin). This coordinate regulation may allow TGF-βs to be useful in the repair of surface wounds, cartilage and bone. Molecules with properties as described in this invention, with lower molecular weights than TGF-β, and which can be either chemically synthesized or readily isolated from natural sources, yet mimic the coordinate regulation of extracellular matrix as induced by the TGF-βs, have significant advantages as therapeutic agents over the use of such complex polypeptides.

Moreover, the phrase "transcriptionally modulate the gene-of-interest" infers a notion of directness. Thus, as used herein, "transcriptionally modulate expression of a gene-of-interest" by a molecule means the effect upon transcription of the gene resulting from either (a) direct binding of the molecule to DNA or RNA, a DNA- or RNA-binding protein, and/or a DNA- or RNA-binding protein complex, or (b) direct binding of the molecule to a protein which directly chemically modifies a DNA- or RNA-binding protein or protein complex.

As used herein "chemically modifies" a DNA- or RNA-binding protein or protein complex means to modify the protein or protein complex through a chemical reaction, including but not limited to, phosphorylation, glycosylation, methylation, acetylation, adenoribosylation, acylation, myristylation, reduction, oxidation, covalent oligomerization or polymerization or proteolytic cleavage.

The invention provides a cell capable of expressing the gene-of-interest, the expression of which is associated with a defined physiological or pathological effect within a multicellular organism. The cell may be a human cell, an animal cell, a plant cell or any eucaryotic cell or procaryotic cell from whatever source.

Further, in the practice of the invention, the gene-of-interest whose expression is associated with a defined physiological or pathological effect within a multicellular organism, may be a human gene.

Moreover, the gene-of-interest may encode a hematopoietic protein. Hematopoietic proteins may include, but are not limited to, colony stimulating factors and erythropoietin (EPO).

Examples of colony stimulating factors useful in the practice of this invention include, but are not limited to, granulocyte-macrophage colony stimulating factor (GM-CSF), granulocyte colony stimulating factor (G-CSF), and macrophage colony stimulating factor (M-CSF).

Further, the gene-of-interest of the invention may encode an interleukin (IL) or a cytokine, or a growth modulating factor. One example of such a growth modulating factor would be a member of the transforming growth factor-β (TGF-β) family i.e. TGF-β1 or TGF-β2 or TGF-β3. A gene-of-interest may also encode a receptor for a steroid hormone, such as the testosterone receptor or the estrogen receptor or for a TGF-β.

The gene-of-interest may also encode a growth hormone. Examples of growth hormones include, but are not limited to, human, bovine, porcine, avian, ovine, piscine, and equine growth hormones. Additionally, the gene-of-interest may also encode polypeptide analogs of the above-identified growth hormones. Additionally, the gene-of-interest could encode a growth hormone releasing factor.

The present invention also provides a viral gene as the gene-of-interest. The viral gene may be a retroviral gene. Retroviral genes of the invention may be from the HIV, HTLV-1, or HTLV-2 virus.

In the practice of the invention the viral gene may be a gene from a hepatitis virus, a herpes virus, a papilloma virus, a cytomegalovirus, or an animal virus.

Animal viruses of the invention may include, but are not limited to, pseudorabies, Marek's, Newcastle's Disease, and IBR viruses.

The gene-of-interest, whose expression is associated with a defined physiological or pathological effect within a multicellular organism, may also be a plant gene. The plant gene may encode an agronomically important trait. Examples of agronomically important traits may include, but are not limited to, germination, sprouting, flowering, fruit ripening, salt tolerance, herbicide resistance, pesticide resistance, fungicide resistance, temperature resistance, and growth.

Additionally, in the practice of the invention the gene-of-interest may be a protozoan gene. Examples of protozoans may include, but are not limited to, a selection from the group consisting of Trypanosoma, Plasmodium, Leishmania, Giardia, Entamoeba, Toxoplasma, Babesia, and Cryptosporidiosis.

Moreover, the gene-of-interest whose expression is associated with a defined physiological or pathological effect within a multicellular organism, may be a helminth gene.

Further, the gene-of-interest may also be an oncogene. Examples of oncogenes may include, but are not limited to, the phl-abl oncogene, the neu oncogene, or the src oncogene. Additionally, the oncogene may be selected from the group consisting of H-ras, N-ras, and K-ras oncogenes.

The present invention additionally provides that the gene-of-interest, whose expression is associated with a defined physiological or pathological effect within a multicellular organism, may encode a naturally occurring receptor. The naturally occurring receptor may be the human low density lipoprotein (LDL) receptor. Further, the receptor may be the receptor for a hemopoietic protein. Examples of hematopoietic proteins may include, but are not limited to, a selection from the group consisting of M-CSF, G-CSF, GM-CSF, and EPO.

The naturally occurring receptor encoded by the gene-of-interest may also be the receptor for an interleukin (IL). Examples of an IL may include, but are not limited to, a selection from the group consisting of IL-1, IL-2, IL-3, IL-4, IL-5, IL-6, IL-7 and IL-8.

Additionally, in the practice of the invention, the naturally occurring receptor may be a cell surface protein which mediates infection of the cell by a virus. Examples of viruses may include, but are not limited to, HIV, HTLV-1, HTLV-2, a hepatitis virus, a herpes virus, a papilloma virus, a cytomegalovirus and a rhinovirus.

In one example of the invention, the receptor which naturally occurs in the cell is a testosterone receptor. In another example of the invention, the receptor which naturally occurs in the cell is an estrogen receptor.

Typically, a ligand, in the context of this invention, is a molecule with a molecular weight of less than 5,000 daltons, more typically less than 2,000 daltons.

This invention also provides a method of determining whether a molecule not previously known to be a modulator of protein biosynthesis is capable of transcriptionally modulating the expression of a gene-of-interest. The method comprises contacting a sample which contains a predefined number of cells with a predetermined amount of a molecule to be tested. Each cell comprises DNA consisting essentially of (i) a modulatable transcriptional regulatory sequence of the gene-of-interest, (ii) a promoter of the gene-of-interest, and (iii) a reporter gene which expresses a polypeptide capable of producing a detectable signal, coupled to, and under the control of, the promoter. The polypeptide expressed by the reporter gene produces the detectable signal under conditions such that the molecule, if capable of acting as a transcriptional modulator of the gene-of-interest, causes a measurable detectable signal to be produced by the polypeptide expressed by the reporter gene.

Quantitatively determining the amount of the signal produced requires comparing the amount of signal produced compared to the amount of produced signal detected in the absence of any molecule being tested or upon contacting the sample with any other molecule. The comparison permits the identification of the molecule as one which causes a change in the detectable signal produced by the polypeptide expressed by the reporter gene and thus identifying the molecule as a molecule capable of transcriptionally modulating the expression of the gene-of-interest.

The phrase "a modulatable transcriptional regulatory sequence of a gene-of-interest" as used herein concerns a DNA sequence capable of regulating the initiation of transcription from the promoter of the gene-of-interest.

Molecules useful in the practice of this invention have the following characteristics. The molecule does not naturally occur in the cell. The molecule specifically transcriptionally modulates expression of the gene-of-interest. Further, the molecule binds to DNA or RNA or binds to a protein through a domain of such protein which is not a ligand binding domain of a receptor which naturally occurs in the cell. The binding of a ligand to the ligand binding domain is normally associated with the defined physiological or pathological effect.

The term "promoter" of a gene-of-interest is defined herein as a minimal DNA sequence necessary for specific initiation of transcription.

In the practice of the invention the sample may comprise cells in monolayers or cells in suspension. The cells of the invention may comprise human, animal, or plant cells. In one example of the invention, the cells are bacterial cells. In another example of the invention, the cells are fungal cells.

Further, the invention provides that the predefined number of cells contained in the sample may be from about $2 \times 10^2$ to about $5 \times 10^5$ cells, typically from about $10^3$ to about $5 \times 10^4$ cells. In theory, the ideal method might use only one cell. In practice, the method may include at least 10 cells per samples. More practically the method may include at least 100 cells per sample.

The invention also provides that the predetermined amount of the molecule to be tested may be based on the volume of the sample. Further, the predetermined amount of the molecule to be tested may be from about 1 pM to about 500 $\mu$M. Typically, in a primary high-throughput screen the predetermined amount would be from about 10 nM to about 500 $\mu$M. Typically in a secondary screen to evaluate initial lead compounds, the predetermined amount would be from about 1 pM to about 20 $\mu$M.

Further, the invention provides that contacting a sample which contains a predefined number of cells with a predetermined amount of a molecule to be tested may be effected from about 1 to about 24 hours, typically from about 2 to about 12 hours. Moreover, contacting a sample which contains a predefined number of cells with a predetermined amount of a molecule to be tested may be effected with more than one predetermined amount of the molecule to be tested. The molecule to be tested may be, but is not limited to, a purified molecule. As used herein, the molecule may also be a mixture of different molecules, e.g. in a fermentation broth or in a natural product extract. Typically, a fermentation broth would be produced by fermentation of a suitable sample under standard conditions known to those skilled in the art. Examples of natural product extracts would include, but are not restricted to, plant extracts, seaweed extracts, insect extracts, spider venoms, etc.

A minimal modulatable transcriptional regulatory sequence may comprise a few nucleotides in length, such as the so-called CCAAT box motif, the octamer binding motif or the heat shock element (91). A gene-of-interest may typically possess multiple motifs with different combinations of modulatable transcriptional regulatory sequences. It has been shown that enhancer elements or other regulatory motifs can be present at many kilobases upstream or downstream from the transcription start site of a gene-of-interest. Thus, as used herein, a modulatable transcriptional regulatory sequence may comprise a few nucleotides or may be naturally or synthetically constructed having multiple elements spanning several hundred kilobases in length. Transcription can also be influenced by the particular nuclear location or local chromatin configuration. In order to optimize a screen for substances that modulate regulatory elements, it may be preferable to situate a reporter gene at the exact chromosomal region where the gene-of-interest resides normally. However, it would be clear to one skilled in the art that the reporter gene may be situated anywhere in a chromosome. In one example in the invention, the modulatable transcriptional regulatory sequence comprises a cloned genomic regulatory sequence. In another example of the invention, the DNA consists essentially of more than one modulatable transcriptional regulatory sequence.

A series of experiments described by K. R. Thomas and M. R. Capecchi (44, 45, 46) have shown that it is possible to direct transfected or microinjected DNA, using homologous DNA sequences, to a specific chromosomal location in mammalian cells. Using homologous recombination, it is possible to replace a gene-of-interest with other sequences at a high frequency. The materials required include a reporter gene (such as luciferase), a selectable marker (such as the neomycin phosphotransferase II gene from Tn5), and sequences derived from the gene-of-interest. These materials would be used to construct a vector which would include, in one embodiment of this invention, a gene-of-interest (free of its normal upstream promoter sequences) and reporter gene, where the reporter gene product was still active.

Two types of selectable markers, one positive and one negative, such as the Herpes Simplex thymidine kinase (TK), greatly enhance the likelihood of achieving homologous recombination. Use of one copy of the TK gene located outside the homologous regions at either end allows for selection of "correct" homologous recombinants. Neomycin resistant cells which are recombined randomly will usually insert via the ends of the linearized, transfected DNA and thus include the TK gene(s). This will allow for selection against these cells in the presence of gancyclovir which is converted to a toxic product. This is the method specifically described by Capecchi. However, this method has not been used to produce cell lines to screen for compounds which modulate the expression of a target gene-of-interest as described herein.

The invention provides that the reporter gene in the DNA contained in the cell sample, which expresses a polypeptide capable of producing a detectable signal coupled to, and under control of, the promoter, may be inserted downstream of the endogenous promoter of the gene-of-interest by homologous recombination. The following provides a method of determining whether a molecule not previously known to be a modulator of protein biosynthesis is capable of transcriptionally modulating the expression of a gene-of-interest which comprises contacting a sample which contains a predefined number of cells with a predetermined amount of a molecule to be tested, each such cell comprising DNA consisting essentially of (i) a modulatable transcriptional regulatory sequence of the gene-of-interest, (ii) a promoter of the gene-of-interest, and (iii) a DNA sequence transcribable into mRNA coupled to and under the control of, the promoter, under conditions such that the molecule, if capable of acting as a transcriptional modulator of the gene-of-interest, causes a measurable difference in the amount of mRNA transcribed from the DNA sequence, quantitatively determining the amount of the mRNA produced, comparing the amount so determined with the amount of mRNA detected in the absence of any molecule being tested or upon contacting the sample with any other molecule, and thereby identifying the molecule as one which causes a change in the detectable mRNA amount of, and thus identifying the molecule as a molecule capable of transcriptionally modulating the expression of the gene-of-interest. In one example of the above-described method, the molecule (a) does not naturally occur in the cell, (b) specifically transcriptionally modulates expression of the gene-of-interest, and (c) binds to DNA or RNA or binds to a protein through a domain of such protein which is not a ligand binding domain of a receptor which naturally occurs in the cell, the binding of a ligand to which ligand binding domain is normally associated with a defined physiological or pathological effect.

Modulatable transcriptional regulatory sequences may also occur within introns of a gene-of-interest. Typically, the exact location of all such regulatory sequences of a gene-of-interest will be unknown. In one example of this invention, the reporter gene will be a reporter gene which can be transcribed into mRNA which can be quantified as a detectable signal. This approach would (i) allow the modulatable transcriptional regulatory sequences of the gene to be in their native environment and arrangement relative to the gene-of-interest including any and all transcriptional regulatory sequences within introns, (ii) obviate the necessity of using permanent cell lines to construct reporter cell lines and (iii) not require knowledge of promoter and modulatable transcriptional regulatory sequences.

In one example of the invention, mRNA is detected by quantitative polymerase chain reaction. Methods for direct detection of mRNA in a rapid and quantitative manner that fulfill the needs of a high throughput screening method described in this invention are not available. A suitable assay would have to meet the following criteria: (i) specific detection of fewer than 50,000 mRNA molecules, (ii) short assay time of a few hours, (iii) simple chemistry, that is amenable to automation. Ideally a "single tube" assay would be used which can be carried out within the same container in which the cells to be tested have been cultured, by eliminating transfer steps which may be time consuming and contribute to assay variation.

Several techniques have been described by others, which may be modified to be useful in the context of this invention. All assays are based on the principle of using a single stranded nucleotide probe containing sequences complementary to the target MRNA transcribed from the gene-of-interest which probe is attached to a solid support to rapidly concentrate (capture) the mRNA out of a crude cell lysate. Cell lysates can be prepared such that ribonucleases are inhibited while hybridization of nucleic acids remains possible, for example in high concentrations of guanidinium isothiocyanate (47). Target mRNA bound to the solid phase can be freed of contaminants by intensive washing and subsequently detected with a second probe which is complementary to a different region of the target mRNA than the capture probe. The second probe would carry an appropriate detectable label.

To obtain optimal sensitivity i.e. obtain a maximal number of labels being specifically bound to a target molecule in the presence of a minimal number of labels being unspecifically retained by other components of the assay mixture, various techniques can be applied to increase signal to noise ratios. A procedure termed reversible target capture has been designed to reduce the background noise by capturing the target molecule - label complexes onto capture probes linked to solid phase, release of the complexes and transfer of the complexes onto new capture probes linked to solid phase and so forth, cycling between steps. Background is reduced by this procedure, because the release step is designed not to release non-specifically bound label that will not therefore be transferred together with the target molecules and will eventually be removed from the mixture (48). This method has a reported sensitivity of 15,000 target mRNA molecules, it has, however the disadvantage of involving multiple transfer steps into new containers.

Beside reducing background the signal to noise ratio can be improved by binding more than one label to a target molecule or by creating many copies of an initial target molecule (amplification). For example, DNA may be detected by a method using an amplification oligonucleotide with a branched structure that can specifically bind to the target molecule and at the same time to many molecules carrying label resulting in an up to 500-fold amplication of specific signal. This method can potentially be carried out in a single tube. Its reported sensitivity is 60,000 target DNA molecules with an assay duration of 4 hours (48). Further methods of amplification include the hybridization dependent replication of RNA via the Q-$\beta$ bacteriophage system (49) or polymerase chain reaction based replication of a cDNA copy of the target mRNA molecule (50). The methods described herein above, have not been used by others in the context of this invention. However, in light of the subject invention, it would be clear to those skilled in the art that use of these methods would facilitate the practice of this invention.

The invention also provides the use of a reporter gene whose product is easily detectable. The reporter gene may encode a luciferase, chloramphenicol acetyltransferase, $\beta$ glucuronidase, $\beta$ galactosidase, neomycin phosphotransferase, or guanine xanthine phosphoribosyltransferase.

The present invention also provides a screening method for determining whether a molecule not previously known to be a modulator of protein biosynthesis is capable of transcriptionally modulating the expression of a gene-of-interest which comprises separately contacting each of a plurality of substantially identical samples, e.g. more than about $10^4$ samples, preferably more than about $10^5$ samples, each sample containing a predefined number of cells under conditions such that contacting is effected with a predetermined amount of each different molecule to be tested.

In theory, the ideal screening method provides contacting one sample with a predetermined amount of each molecule to be tested. In practice, the method may include contacting at least 3 substantially identical samples, with a predetermined amount of each molecule to be tested; more practically, contacting about 9 substantially identical samples with a predetermined amount of each molecule to be tested.

Moreover, the invention provides a method of essentially simultaneously screening molecules to determine whether the molecules are capable of transcriptionally modulating one or more genes of interest in a panel of such genes. The method comprises essentially simultaneously screening the molecules against each of the genes of interest by separately contacting each of a plurality of substantially identical samples, each of which contains a predefined number of cells, with a predetermined amount of a different molecule to be tested.

The screening method also provides a quantitative testing range wherein at least about $10^3$ samples per week are contacted with different molecules against either one or a panel of such genes of interest.

Further, in the practice of this invention a method for determining whether a molecule not previously known to be a modulator of protein biosynthesis is capable of transcriptionally modulating the expression of a gene-of-interest is provided. This method works in human and in animal cells. Data is presented so that one skilled in the art could make the method work in fungal cells. In addition, one skilled in the art would realize that the method may be effected in plant cells or in bacterial cells. In the case wherein luciferase is used as a reporter, this enzyme has been shown by others to be active in plant cells (89).

The invention also provides a method for transcriptionally modulating in a multicellular organism, the expression of a gene-of-interest, the expression of which is associated with a defined physiological or pathological effect in the organism. The method comprises administering, e.g. oral administration, administration as a suppository, topical contact, intravenous, intramuscular or subcutaneous administration, to the organism an amount of a molecule effective to transcriptionally modulate expression of the gene thereby affecting the defined physiological or pathological effect. The molecule (a) does not naturally occur in the organism, (b) specifically transcriptionally modulates expression of the gene-of-interest, and (c) binds to DNA or RNA or binds to a protein through a domain of such protein which is not a ligand binding domain of a receptor which naturally occurs in the organism. Moreover, the binding of a ligand to the ligand binding domain is normally associated with the defined physiological or pathological effect.

In the practice of the invention, examples of a multicellular organism include, but are not limited to, a human, an animal, or a plant.

The defined pathological effect may be associated with a disorder and the modulated expression of the gene-of-interest may be associated with amelioration of the disorder. Further, examples of disorders include but are not limited to, a selection from the group consisting of cancer, a hematopoietic dysfunction, diabetes, tissue inflammation, atherosclerosis, dysfunctions of memory or learning, dysfunctions in a cholesterol or other metabolic pathway; viral, fungal or parasitic infections. Thus, the gene-of-interest is not necessarily part of the normal genetic make-up of the multicellular organism but rather can be introduced via infection by a pathogen. In one example of the invention, the defined physiological effect is growth and the organism is an animal such as a man, cow, a pig, a bird, a fish, a sheep or a horse. The gene-of-interest associated with growth could be the gene encoding growth hormone or growth hormone releasing factor. In another example of the invention the defined physiological or pathological effect is an agronomically important trait. In a further example of the invention administration comprises topical contact. Further in another example of the invention, administration comprises oral, transdermal, intravenous, intramuscular or subcutaneous administration. Further in one example of the invention, provides the gene-of-interest encodes a naturally occurring receptor. Further, in one example of the invention, the receptor is a testosterone receptor. Further, in another example of the invention the receptor is an estrogen receptor. Further, in another example of the invention, the receptor which naturally occurs in the cell is a testosterone receptor. Further, in another example of the invention the receptor which naturally occurs in the cell is an estrogen receptor. Further, in another example of the invention the gene-of-interest encodes a TGF-β receptor. Moreover, in another example of this invention, the gene-of-interest encodes a TGF-β. In one example of the invention the TGF-β is TGF-β1. Further, in another example of the invention the TGF-β is TGF-β2. Further, in another example of the invention the TGF-β is TGF-β3. Further, in another example of the invention the gene-of-interest encodes an oncogene. Further, in another example of the invention the oncogene is the neu oncogene. Further, in another example of the invention the oncogene is selected from the group consisting of H-, N-, and K-ras oncogenes.

This invention further provides a method for modulating the expression of a polypeptide by a cell which i) comprises DNA encoding and ii) is capable of expressing such a polypeptide, which comprises contacting the cell with an amount of a molecule effective so to transcriptionally modulate expression of the polypeptide by the cell which molecule (a) does not naturally occur in the cell and (b) binds to DNA or RNA, or binds to a protein through a domain of such protein which is not a ligand-binding domain of a receptor which naturally occurs in the cell, the binding of a ligand to which ligand binding domain is normally associated with modulating transcriptional expression of a polypeptide. In one example of the invention, wherein the polypeptide is a homologous polypeptide. In another example of the invention, the molecule specifically transcriptionally modulates expression of the polypeptide. Further, in another example of the invention the polypeptide is a desired product. Further, in another example of the invention, the desired product is a monoclonal antibody. Moreover, in a further example of the invention, the DNA is recombinant DNA. Further, in another example of the invention, the cell is a animal cell. Further, in another example of the invention, the cell is a plant cell. Further, in another example of the invention, the cell is a bacterial cell. Further, in another example of the invention, the cell is a fungal cell. Further, in another example of the invention, the polypeptide is associated with production of a desired product. Further, in another example of the invention, the desired product is an antibiotic. Further, in another example of the invention, the desired product is citric acid. The following provides a biological method for recovering a substance from a mixture containing the substance which involves contacting the mixture with cells so as to separately recover the substance, which cells (i) comprise DNA encoding, and (ii) are capable of expressing a gene product, which gene product facilitates separating the substance from the mixture so as to recover the substance from the mixture, the improvement comprising (1) treating the cells with a molecule which (a) does not naturally occur in the cell and (b) binds to DNA or RNA or binds to a protein through a domain of such protein which is not a ligand binding domain of a receptor which naturally occurs in the cell, the binding of a ligand to which ligand binding domain is normally associated with increased production of the gene product. Further, in another example of the invention, the substance is a metal. The following provides a biological method for treating a substance with cells so as to effect a biochemical transformation by contacting the substance with cells which (i) comprises DNA encoding, and (ii) is capable of expressing a gene product which permits biochemical transformation, the improvement comprising contacting the cells with a molecule which (a) does not naturally occur in the cell and (b) binds to DNA or RNA or binds to a protein through a domain of such protein which is not a ligand binding domain of a receptor which naturally occurs in the cell, the binding of a ligand to which ligand binding domain is normally associated with enhanced production of the gene product. Further, in another example of the invention, the biochemical transformation is associated with the production of a steroid. Further, in another example of the invention, the biochemical transformation is associated with the production of an alcohol. Further, in another example of the invention, the biochemical transformation is associated with the degradation of petroleum products.

Clearly, this invention would have commercial applications both in the case where the polypeptide itself is commercially important, and in the case where expression of the polypeptide mediates the production of a molecule which is commercially important. Examples include, but are not limited to:

1. increasing expression of a polypeptide which is associated with the rate limiting step in antigen production wherein the antigen is produced for a vaccine. Vaccines can be used against viral, bacterial or parasitic infections. Such viral vaccines include poliomyelitis, measles, mumps and rubella. In addition, foot and mouth disease vaccine and rabies vaccine are of major commercial importance. Viable, disease-associated viruses can be subsequently inactivated, live viruses can be attenuated to lose their pathogenicity or genetically engineered. The expression of a viral antigen could be under the control of a heterologous promoter (80);

2. increasing expression of monoclonal antibodies by hybridoma cells, i.e., cell lines resulting from the fusion of a B-lymphocytes with a myeloma cell lines. Monoclonal antibodies could be produced by growing the hybridoma in tissue culture or in vivo (80);

3. increasing the expression of a heterologous polypeptide by a cell i.e. a polypeptide introduced into the cell by genetic engineering and, typically, under the control of a strong promoter. Examples of such promoters include the promoter of the SV40 virus, the immediate early promoter of the cytomegalovirus or the baculovirus promoter. Examples of heterologous polypeptides would include tissue plasminogen activator, human or animal growth hormones, blood clotting factors, erythropoietin, interleukins, interferons, the colony stimulating factors G-, GM- and M-CSF, and trans-forming growth factors-β1, -β2 and -β3. In a variation of this invention, the polypeptide of interest could be expressed by the cell without genetic engineering. One example would be the production of interferon alpha by the lymphoblastoid cell line 'Namalva' (80);

4. increasing plant derived products as used in fragrances and perfumes, flavoring compounds or sweeteners e.g. the basic proteins from *Thaumatococcus danielli*, insecticides, anti-fungal compounds or pesticides (79);

5. increasing the expression of a polypeptide which is associated with the rate limiting step in bioleaching of metals such as uranium, copper, silver, manganese etc. For example, as carried out by the organism Thiobacillus sp., algae or fungi (81);

6. increasing the expression of a polypeptide which is associated with the rate limiting step in removal of nitrogen or phosphate or toxic waste minerals from water, e.g. as carried out by Nitrobacter sp. or Acinetobacter sp. (82);

7. increasing the expression of a polypeptide which is associated with the rate limiting step in stimulating methane production from biological waste, typically from the methanogenic micro-organisms archaebacteria (83);

8. increasing the expression of a polypeptide which is associated with the rate limiting step in the biodegradation of marine oil spills (e.g., aliphatic hydrocarbons, halogenated aliphatics, halogenated aromatics). In one instance, biodegradation is effected by the conversion of petroleum products to emulsified fatty acids. Bacteria useful in this invention include, but are not restricted to, Archromobacter, Arthrobacter, Flavobacterium, Nocardia, Pseudomonas (e.g. *Pseudomonas oleovorans*) and Cytophaga. Yeast useful in this invention include, but are not restricted to, Candida (e.g., *Candida tropicalis*), Rhodotorula, and Trichosporon (84);

9. increasing the expression of a polypeptide which is associated with the rate limiting step in biodegradation of lignin (84);

10. increasing the expression of a polypeptide which is associated with the rate limiting step in the biotransformation of:

steroids and sterols (71), e.g., by Rhizopus sp., Saccharomyces (70) Corynebacterium sp.

D sorbitol to L sorbose by Acetobacter suboxydans (78)

racemic mixtures (77)

prochiral substrates terpenoids (72)

alicyclic and heteroalicyclic compounds (73)

antibiotics (74)

aromatic and heterocyclic structures including phthalic acid esters, lignosulfonates, surfactants and dyes (75)

naphthyridines by Penicillium sp (75)

polynuclear aromatic hydrocarbons (75)

aliphatic hydrocarbons (76)

amino acid and peptides (77)

glucose to fructose (78)

glucose to gluconic acid (78)

raffinose to sucrose and galactose (79)

lactose sucrose 12. increasing the expression of a polypeptide which is associated with the rate limiting step in the production of commercially important enzymes from micro-organisms, e.g. lactase from *Aspergillus oryzae, Escherichia coli, Bacillus stearothermophilus;*

13. increasing the expression of a polypeptide which is associated with the rate limiting step in the growth of Saccharomyces on molasses (51);

14. increasing the expression of a polypeptide which is associated with the rate limiting step in the growth of Candida on spent sulphite liquor (51);

15. increasing the expression of a polypeptide which is associated with the rate limiting step in the growth of yeast on higher n-alkanes (52);

16. increasing the expression of a polypeptide which is associated with the rate limiting step in the growth of bacteria on higher n-alkanes (52);

17. increasing the expression of a polypeptide which is associated with the rate limiting step in the growth of bacteria or yeast on methane or methanol (53);

18. increasing the expression of a polypeptide which is associated with the rate limiting step in the assimilation of atmospheric nitrogen by e.g., Azotobacteria sp., Rhizobium sp., or Cyanobacteria;

19. increasing the expression of a polypeptide which is associated with the rate limiting step in the production of insectides from Bacillus sp., e.g. *Bacillus thuringiensis* (54);

20. increasing the expression of a polypeptide which is associated with the rate limiting step in the production of insectides from entomogenous fungi such as Deuteromycetes, e.g. *Verticillium lecanii* and *Hirsutella thompsonii* (55);

21. increasing the expression of a polypeptide which is associated with the rate limiting step in the production of ethanol from cellulosic materials, starch crops, sugar cane, fodder beats, molasses by, for example, *Saccharomyces cerevisiae, S. uvarum, Schizosaccharomyces pombe* or Kluyveromyces sp. (55,59);

22. increasing the expression of a polypeptide which is associated with the rate limiting step in acetic acid production from ethanol by Acetobacter sp. or Gluconobacter sp. (55);

23. increasing the expression of a polypeptide which is associated with the rate limiting step in the lactic acid production by the family of Lactobacillaceae (56);

24. increasing the expression of a polypeptide which is associated with the rate limiting step in the citric acid production by Candida sp., *Aspergillus niger* using e.g., molasses or starch (56);

25. increasing the expression of a polypeptide which is associated with the rate limiting step in gluconic acid production by e.g. Pseudomonas sp., Gluconobacter sp., and Acetobacter sp. (57);

26. increasing the expression of a polypeptide which is associated with the rate limiting step in the production of amino acids by bacteria or fungi (58);

27. increasing the expression of a enzyme in a cell, which enzyme catalyzes the resolution of racemic mixtures of amino acids (58);

28. increasing the expression of a polypeptide which is associated with the rate limiting step in the production of extracellular polysaccharides, e.g. by Corynebacterium sp., Pseudomonas sp., or Erwinia tahitica. Other examples include the production of scleroglycan from the fungus Sclerotium sr., pullulan from *Aureobasidium pullulans*, curdlan from *Alcaligens faecalis*, and dextrans from Streptobacterium sp. or Streptocucus sp. Other Examples include anionic polysacharides from *Arthrobacter viscosus*, bacterial alginates from *Azotobacter vinelandii*, xanthan from *Xanthomonas campestris*.

29. increasing the expression of a polypeptide which is associated with the rate limiting step in the production of an antifungal compound (e.g. Griseofulvin) and penicillins from Penicillium sps.

30. increasing the expression of a polypeptide which is associated with the rate limiting step in the production of antibiotics by fungi, e.g. polyether antibiotics (66), chloramphenicol (66), ansamycines (65), tetracyclines (64), macrolides (63), aminoglycosides (62), clavans, cephalosporins, cephamycins (61) from Streptomyces sp.;

31. increasing the expression of a polypeptide which is associated with the rate limiting step in the production of antitumor substances, e.g., actinomycin D, anthracyclines, and bleomycin from Streptomyces sp.;

32. increasing the expression of a polypeptide which is associated with the rate limiting step in the production of nucleic acids, nucleotides and related compounds, e.g., 5' inosinate (IMP), 5' guanylate (GMP), cAMP by e.g. *Brevibacterium ammoniagenes* (60);

33. increasing the expression of a polypeptide which is associated with the rate limiting step in the production of vitamins, e.g. vitamin B12 by *Pseudomonas denitrificans, Propionibacterium shermanii*, or *Rhodopseudomonas protamicus*;

34. increasing the expression of a polypeptide which is associated with the rate limiting step in the production of riboflavin by *Ashbya gossypii* or *Bacillus subtilis.*;

35. increasing the expression of a polypeptide which is associated with the rate limiting step in the production of ergosterol by yeast, e.g. *Saccharomyces cerevisiae;*

36. increasing the expression of a polypeptide which is associated with the rate limiting step in the production of ergot alkaloids by Claviceps sp (67);

37. increasing the expression of a polypeptide which is associated with the rate limiting step in the production of secondary metabolites useful for selected therapeutic uses in human medicine, e.g. cyclosporin from *Trichoderma polysporum* (68);

38. increasing the expression of a polypeptide which is associated with the rate limiting step in the production of secondary products from plant cell cultures, e.g. cinnamic acid derivatives in Coleus blume; shikonins from Lithospermum erythrophizon (69);

39. increasing the expression of a polypeptide which is associated with the rate limiting step in the production of wine and beer by Sacchromyces sp. (85,86);

40. increasing the expression of a polypeptide which is associated with the rate limiting step in the production of yogurt or cheese by Staphylococcus sp., Lactobacillus sp. and Propionibacterium sp. (87,88);

41. increasing the expression of a polypeptide which is associated with the rate limiting step in the fermentation of cocoa from Theobroma cacao by fungi and bacteria;

42. increasing the expression of a polypeptide which is associated with the rate limiting step in the fermentation of coffee beans from Coffea sp. by fungi and bacteria.

In each case the invention would include the following steps (i) identification of the protein responsible for controlling the rate limiting step and (ii) screening for molecules capable of increasing the production of that protein using the methods described herein as will be clearly and readily understood by one skilled in the art. The invention provides both for the method of screening for such molecules and for the use of such molecules to regulate expression of a rate limiting polypeptide as described herein.

Additionally, the method for transcriptionally modulating in a multicellular organism the expression of a gene-of-interest provides that growth may be the defined physiological effect and the organism is an animal such as a cow, a pig, a bird, a fish, a sheep, or a horse.

Further, the method for transcriptionally modulating in a multicellular organism the expression of a gene-of-interest provides that the agronomically important trait may be the defined physiological or pathological effect.

This invention provides a method for enhancing the expression of human growth hormone by a cell which (i) comprises DNA encoding, and (ii) is capable of expressing, human growth hormone. The method comprises contacting the cell with an amount of a molecule having the structure:

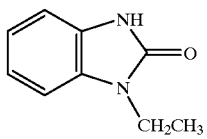

effective to enhance the expression of human growth hormone by the cell.

Additionally, this invention provides a method of increasing the growth of a human being who (i) comprises DNA encoding, and (ii) is capable of expressing, human growth hormone, comprising administering to the human being an amount of a molecule having the structure:

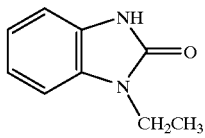

effective to enhance expression of human growth hormone by, and thus growth of, the human being.

The invention also provides a method for enhancing the expression of human growth hormone by a cell which (i) comprises DNA encoding, and (ii) is capable of expressing, human growth hormone, comprising contacting the cell with an amount of a molecule having the structure:

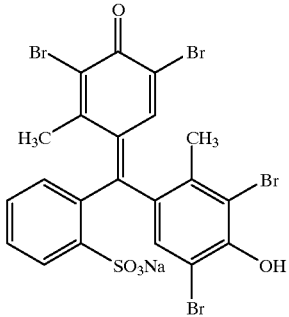

effective to enhance the expression of human growth hormone by the cell.

Another provision of the present invention concerns a method of increasing the growth of a human being who (i) comprises DNA encoding, and (ii) is capable of expressing, human growth hormone. The method comprises administering to the human being an amount of a molecule having the structure:

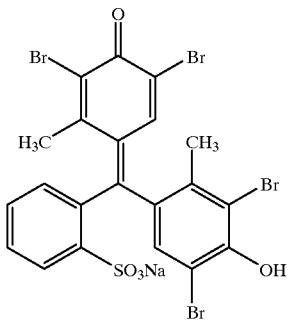

effective to enhance expression of human growth hormone by, and thus growth of, the human being.

This invention also concerns a method for enhancing the expression of human growth hormone by a cell which (i) comprises DNA encoding, and (ii) is capable of expressing, human growth hormone, comprising contacting the cell with an amount of a molecule having the structure:

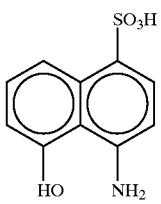

effective to enhance the expression of human growth hormone by the cell.

Further, this invention provides a method of increasing the growth of a human being who (i) comprises DNA encoding, and (ii) is capable of expressing, human growth hormone, comprising administering to the human being an amount of a molecule having the structure:

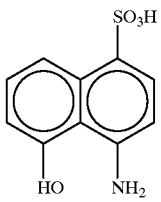

effective to enhance expression of human growth hormone by, and thus growth of, the human being.

Additionally, this invention concerns a method for enhancing the expression of human growth hormone by a cell which (i) comprises DNA encoding, and (ii) is capable of expressing, human growth hormone, comprising contacting the cell with an amount of a molecule having the structure:

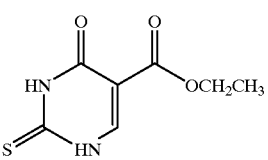

effective to enhance the expression of human growth hormone by the cell.

Additionally, the invention provides a method of increasing the growth of a human being who (i) comprises DNA encoding, and (ii) is capable of expressing, human growth hormone. The method comprises administering to the human being an amount of a molecule having the structure:

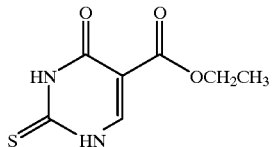

effective to enhance expression of human growth hormone by, and thus growth of, the human being.

Further, the invention provides another method for enhancing the expression of human growth hormone by a cell which (i) comprises DNA encoding, and (ii) is capable of expressing, human growth hormone. The method comprises contacting the cell with an amount of a molecule having the structure:

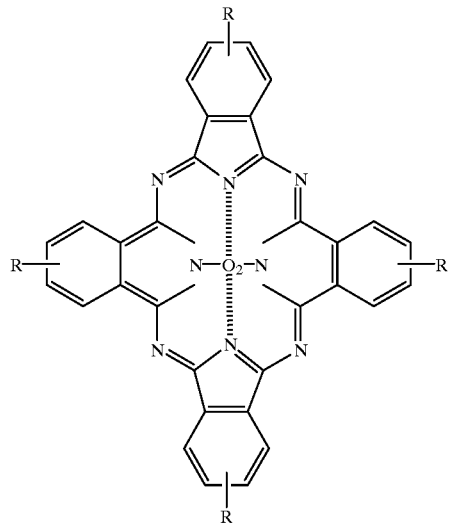

wherein R is 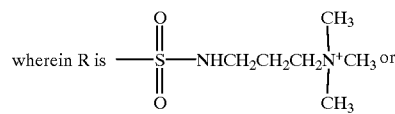 or

effective to enhance the expression of human growth hormone by the cell.

Additionally, the invention provides a method of increasing the growth of a human being who (i) comprises DNA encoding, and (ii) is capable of expressing, human growth hormone, comprising administering to the human being an amount of a molecule having the structure:

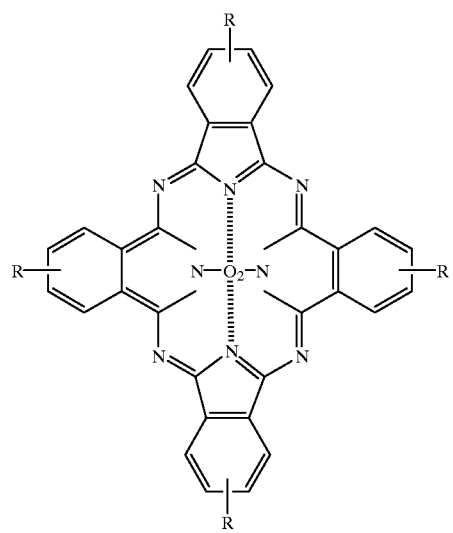

wherein R is 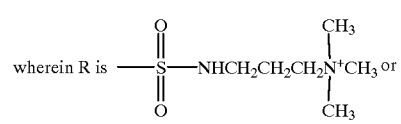 or

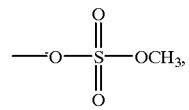

effective to enhance expression of human growth hormone by, and thus growth of, the human being.

Further, this invention provides a method for enhancing the expression of human growth hormone by a cell which (i) comprises DNA encoding, and (ii) is capable of expressing, human growth hormone. The method comprises contacting the cell with an amount of a molecule having the structure:

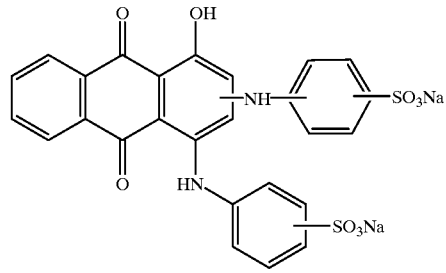

effective to enhance the expression of human growth hormone by the cell.

Further more, this invention provides a method of increasing the growth of a human being who (i) comprises DNA encoding, and (ii) is capable of expressing, human growth hormone. The method comprises administering to the human being an amount of a molecule having the structure:

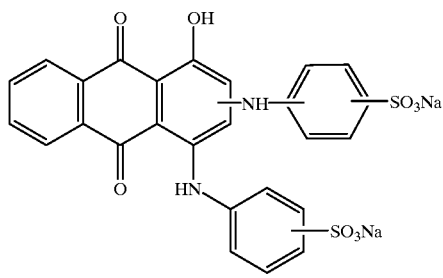

effective to enhance expression of human growth hormone by, and thus growth of, the human being.

The present invention provides a method for enhancing the expression of G-CSF by a cell which (i) comprises DNA encoding, and (ii) is capable of expressing, G-CSF. The method comprises contacting the cell with an amount of a molecule having the structure:

effective to enhance the expression of G-CSF by the cell.

The present invention also provides a method for increasing the formation of neutrophils in a human being who (i) comprises DNA encoding, and (ii) is capable of expressing, G-CSF. The method comprises administering to the human being an amount of a molecule having the structure:

effective to enhance the expression of GCSF by, and thus increase the formation of neutrophils in, the human being.

The present invention also provides a method for enhancing the expression of G-CSF by a cell which (i) comprises DNA encoding, and (ii) is capable of expressing, G-CSF. The method comprises contacting the cell with an amount of a molecule having the structure:

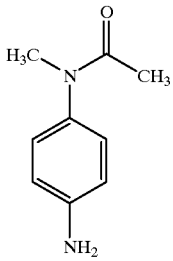

effective to enhance the expression of G-CSF by the cell.

Additionally, the invention provides a method of increasing the formation of neutrophils in a human being who (i) comprises DNA encoding, and (ii) is capable of expressing, G-CSF. The method comprises administering to the human being an amount of a molecule having the structure:

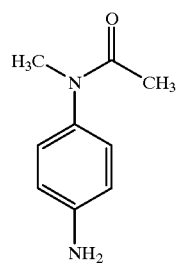

effective to enhance expression of G-CSF by, and thus increase the formation of neutrophils in, the human being.

Further, the invention provides another method for enhancing the expression of G-CSF by a cell which (i) comprises DNA encoding, and (ii) is capable of expressing, G-CSF. The method comprises contacting the cell with an amount of a molecule having the structure:

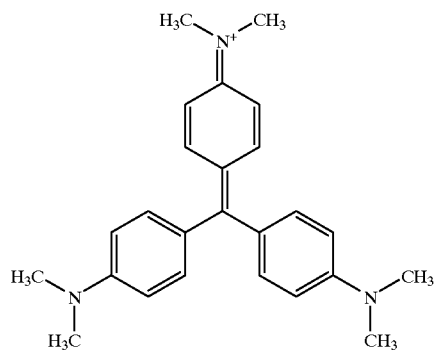

effective to enhance the expression of G-CSF by the cell.

The present invention provides another method of increasing the formation of neutrophils in a human being who (i) comprises DNA encoding, and (ii) is capable of expressing, G-CSF. The method comprises administering to the human being an amount of a molecule having the structure:

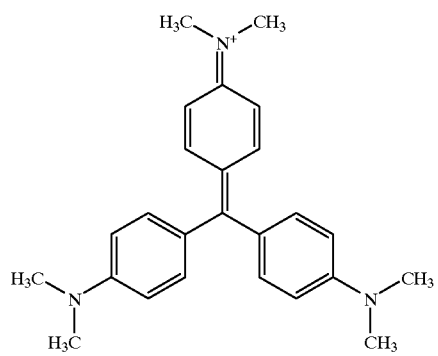

effective to enhance expression of G-CSF by, and thus increase the formation of neutrophils in, the human being.

The invention also concerns a method for enhancing the expression of G-CSF by a cell which (i) comprises DNA encoding, and (ii) is capable of expressing, G-CSF comprising contacting the cell with an amount of a molecule having the structure:

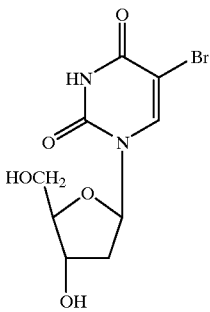

effective to enhance the expression of G-CSF by the cell.

Additionally, the invention concerns a method of increasing the formation of neutrophils in a human being who (i) comprises DNA encoding, and (ii) is capable of expressing, G-CSF, comprising administering to the human being an amount of a molecule having the structure:

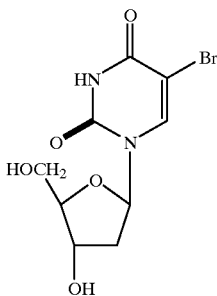

effective to enhance expression of G-CSF by, and thus increase the formation of neutrophils in, the human being.

This invention further concerns a method for enhancing the expression of G-CSF by a cell which (i) comprises DNA encoding, and (ii) is capable of expressing G-CSF. The method comprises contacting the cell with an amount of a molecule having the structure:

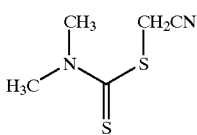

effective to enhance the expression of G-CSF by the cell.

Further the invention provides a method of increasing the formation of neutrophils in a human being who (i) comprises DNA encoding, and (ii) is capable of expressing, G-CSF, comprising administering to the human being an amount of a molecule having the structure:

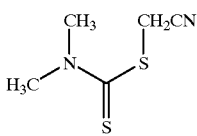

effective to enhance expression of G-CSF by, and thus increase the formation of neutrophils in, the human being.

Additionally, the present invention concerns a method for enhancing the expression of G-CSF by a cell which (i) comprises DNA encoding, and (ii) is capable of expressing, G-CSF, comprising contacting the cell with an amount of a molecule having the structure:

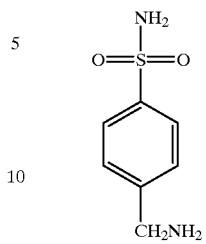

effective to enhance the expression of G-CSF by the cell.

The invention further concerns a method of increasing the formation of neutrophils in a human being who (i) comprises DNA encoding, and (ii) is capable of expressing G-CSF wherein the method comprises administering to the human being an amount of a molecule having the structure:

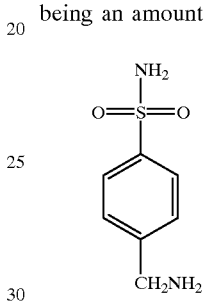

effective to enhance expression of G-CSF by, and thus increase the formation of neutrophils in, the human being.

Also, the invention provides a method for enhancing the expression of G-CSF by a cell which (i) comprises DNA encoding, and (ii) is capable of expressing G-CSF. The method comprises contacting the cell with an amount of a molecule having the structure:

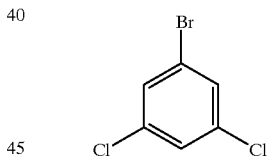

effective to enhance the expression of G-CSF by the cell.

The invention additionally concerns a method of increasing the formation of neutrophils in a human being who (i) comprises DNA encoding, and (ii) is capable of expressing, G-CSF, wherein the method comprises administering to the human being an amount of a molecule having the structure:

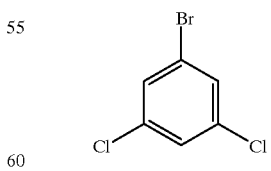

effective to enhance expression of G-CSF by, and thus increase the formation of neutrophils in, the human being.

Another provision of the present invention is a method for enhancing the expression of G-CSF by a cell which (i) comprises DNA encoding, and (ii) is capable of expressing G-CSF. The method comprises contacting the cell with an amount of a molecule having the structure:

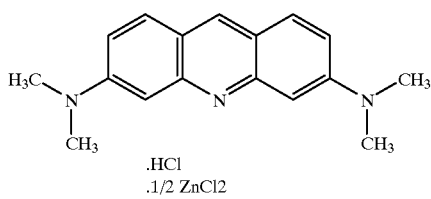

.HCl
.1/2 ZnCl2 effective to enhance the expression of G-CSF by the cell.

Additionally, the invention provides a method of increasing the formation of neutrophils in a human being who (i) comprises DNA encoding, and (ii) is capable of expressing G-CSF. The method comprises administering to the human being an amount of a molecule having the structure:

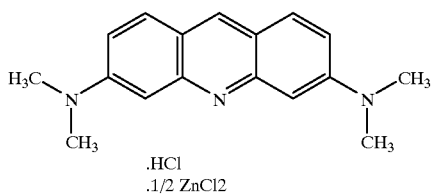

.HCl
.1/2 ZnCl2 effective to enhance expression of G-CSF by, and thus increase the formation of neutrophils in the human being.

The present invention provides another method for enhancing the expression of G-CSF by a cell which (i) comprises DNA encoding, and (ii) is capable of expressing, G-CSF. The method comprises contacting the cell with an amount of a molecule having the structure:

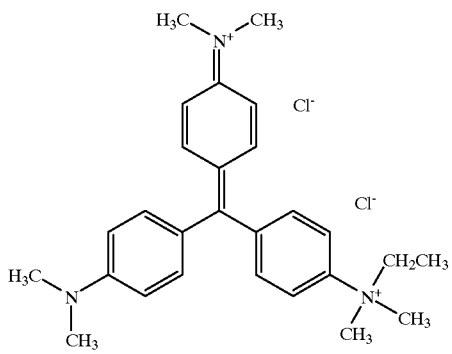

effective to enhance the expression of G-CSF by the cell.

Further, the present invention concerns a method of increasing the formation of neutrophils in a human being who (i) comprises DNA encoding, and (ii) is capable of expressing G-CSF. The method comprises administering to the human being an amount of a molecule having the structure:

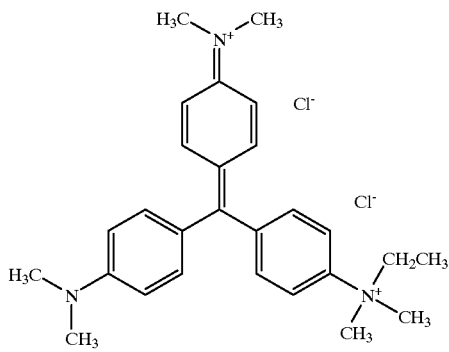

effective to enhance expression of G-CSF by, and thus increase the formation of neutrophils in, the human being.

This invention also concerns a method of decreasing the expression of G-CSF by a cell which (i) comprises DNA encoding, and (ii) is capable of expressing, G-CSF. The method comprises contacting the cell with an amount of a molecule having the structure:

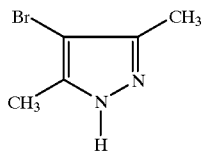

effective to decrease the expression of G-CSF by the cell.

Additionally, this invention provides a method of decreasing the formation of neutrophils and affecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

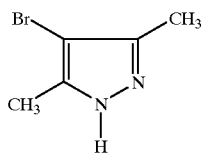

effective to decrease expression of G-CSF by, and thus decrease the formation and affect the metabolic functions of neutrophils in, the human being.

Further, the invention also concerns a method of decreasing the expression of G-CSF by a cell which (i) comprises DNA encoding, and (ii) is capable of expressing, G-CSF. The method comprises contacting the cell with an amount of a molecule having the structure:

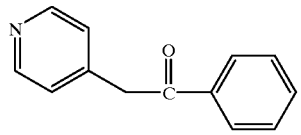

effective to decrease the expression of G-CSF by the cell.

Additionally, this invention provides a method of decreasing the formation of neutrophils and affecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

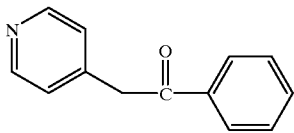

effective to decrease expression of G-CSF by, and thus decrease the formation and affect the metabolic functions of neutrophils in, the human being.

The invention further provides a method of decreasing the expression of G-CSF by a cell which (i) comprises DNA encoding, and (ii) is capable of expressing, G-CSF. The method comprises contacting the cell with an amount of a molecule having the structure:

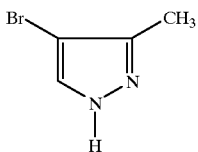

effective to decrease the expression of G-CSF by the cell.

Additionally, this invention provides a method of decreasing the formation of neutrophils and effecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

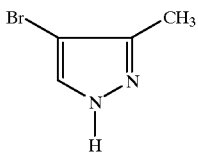

effective to decrease expression of G-CSF by, and thus decrease the formation and affect the metabolic functions of neutrophils in, the human being.

Further, the present invention a method of decreasing the expression of G-CSF by a cell which (i) comprises DNA encoding, and (ii) is capable of expressing, G-CSF. The method comprises contacting the cell with an amount of a molecule having the structure:

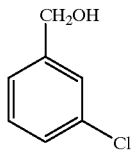

effective to decrease the expression of G-CSF by the cell.

Additionally, this invention provides a method of decreasing the formation of neutrophils and affecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

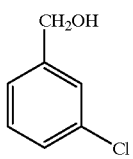

effective to decrease expression of G-CSF by, and thus decrease the formation and affect the metabolic functions of neutrophils in, the human being.

The present invention further provides a method of decreasing the expression of G-CSF by a cell which (i) comprises DNA encoding, and (ii) is capable of expressing, G-CSF. The method comprises contacting the cell with an amount of a molecule having the structure:

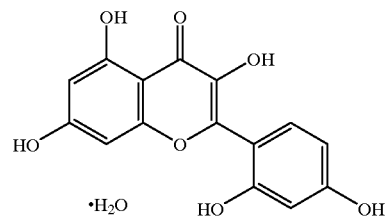

effective to decrease the expression of G-CSF by the cell.

Further still the invention provides a method of decreasing the formation of neutrophils and affecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

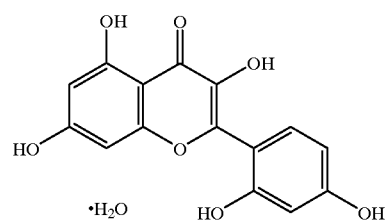

effective to decrease expression of G-CSF by, and thus decrease the formation and affect the metabolic functions of neutrophils in, the human being.

The present invention also concerns a method of decreasing the expression of G-CSF by a cell which (i) comprises DNA encoding, and (ii) is capable of expressing, G-CSF. The method comprises contacting the cell with an amount of a molecule having the structure:

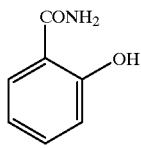

effective to decrease the expression of G-CSF by the cell.

Additionally, the present invention concerns a method of decreasing the formation of neutrophils and affecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

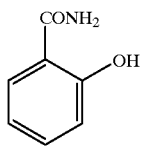

effective to decrease expression of G-CSF by, and thus decrease the formation and affect the metabolic functions of neutrophils in, the human being.

The present invention also concerns a method of decreasing the expression of G-CSF by a cell which (i) comprises DNA encoding, and (ii) is capable of expressing, G-CSF. The method comprises contacting the cell with an amount of a molecule having the structure:

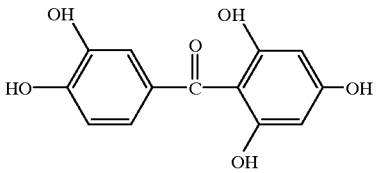

effective to decrease the expression of G-CSF by the cell.

Further, the invention concerns a method of decreasing the formation of neutrophils and affecting the metabolic functions of neutrophils, which has implications for the treatment of inflammatory and autoimmune disorders in a human being who (i) comprises DNA encoding, and (ii) is capable of expressing, G-CSF, comprising administering to the human being an amount of a molecule having the structure:

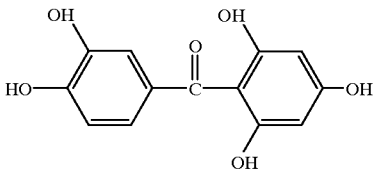

effective to decrease expression of G-CSF by, and thus decrease the formation and affect the metabolic functions of neutrophils in, the human being.

Moreover, the invention provides a method of decreasing the expression of a mammary tumor virus by a cell which (i) comprises DNA encoding, and (ii) is capable of expressing, a mammary tumor virus. The method comprises contacting the cell with an amount of a molecule having the structure:

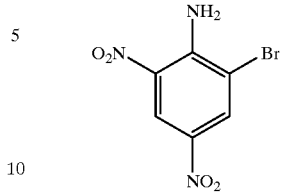

effective to decrease the expression of a mammary tumor virus by the cell.

Finally, the invention also provides a method of suppressing the proliferation of a mammary tumor virus in a subject who (i) comprises DNA encoding, and (ii) is capable of expressing, a mammary tumor virus, comprising administering to the subject an amount of a molecule having the structure:

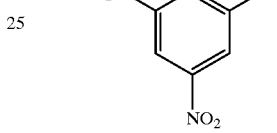

effective to suppress the proliferation of a mammary tumor virus in the subject.

EXPERIMENTAL DETAILS

Materials and Methods

A. Cell Culture

All media and reagents used for routine cell culture were purchased from Gibco (Grand Island, N.Y.), Hazelton (Lenexa, Kans.), or Whittaker M.A. Biologicals (Walkersville, Md.). Fetal calf serum (FCS) was from Hyclone (Logan, Utah), and nutrients used for serum-free defined media were purchased from Sigma (St. Louis, Mo.), Boehringer Mannheim (Indianapolis, Ind.), Bachem (Torrance, Calif.) and Collaborative Research (Bedford, Mass.).

NIH/3T3 fibroblast cells (ATCC number CRL 1658) were used for transfection of plasmids containing the mouse mammary tumor virus (MMTV) promoter linked to firefly luciferase coding sequences (see below). Cells were propagated in Dulbecco's modified Eagle's medium (DMEM) obtained from Gibco, Grand Island, N.Y. and supplemented with 10% FCS. For high-throughput (HTP) screening, transfected NIH/3T3 clones were transferred to serum free defined medium consisting of Iscove's modified Eagle's medium (IMEM) and Ham's F12 medium (1:1) supplemented with growth factors, hormones and nutrients as described previously (43).

A rat pituitary cell line, designated GC, (4, 25) was used for transfection of plasmids containing the human growth hormone promoter (see below) and was maintained in DMEM and Ham's F12 medium (1:1), supplemented with 12.5% FCS. For HTP screening, transfected GC clones were transferred to serum free defined medium consisting of DMEM and Ham's F12 medium (1:1) supplemented with growth factors, hormones and nutrients as described previously (17, 5).

A human bladder carcinoma cell line (U5637, ATCC number HTB 9) was used for transfection of plasmids containing the human Granulocyte-Colony Stimulating Factor (G-CSF) promoter (see below) and was maintained in RPMI medium supplemented with 10% FCS. For HTP screening, transfected 5637 clones were transferred to a serum free defined medium identical to that used for the NIH/3T3 clones.

G418 (Geneticin, Gibco) at 0.2 mg/ml was routinely added to both serum and serum free defined media for selection and maintenance of cell lines transfected with the neomycin resistance gene.

B. Plasmid Construction and Molecular Cloning of Promoter-Reporter Fusion Constructs to be Transfected into Cells Used for a 2,000-Chemical Transcription Screen This section describes (a) the molecular cloning of the human G-CSF promoter and adjacent 5' transcriptionally modulatable regulatory sequences and (b) the making of constructs where there regulatory sequences or those of the human growth hormone (hGH) gene or those of the mouse mammary tumor virus (MMTV) long terminal repeat (LTR) control the expression of the firefly luciferase gene. These constructs were transfected into cells as described in Section E and used for a high-throughput pilot screen of 2,000 chemicals to identify chemicals acting as specific transcriptional modulators (see Section G and "Results").

Unless otherwise indicated cloning procedures were performed essentially according to Maniatis et al. (1982) (28). Oligonucleotides were synthesized by the beta-cyanoethyl phosphoramidite method according to protocols provided by the manufacturer of the DNA-synthesizer (Model 380A, Applied Biosystems (Foster City, Calif.).

1. Construction of the MMTV Promoter-Luciferase fusion plasmid (pMluci)

Figure 1:
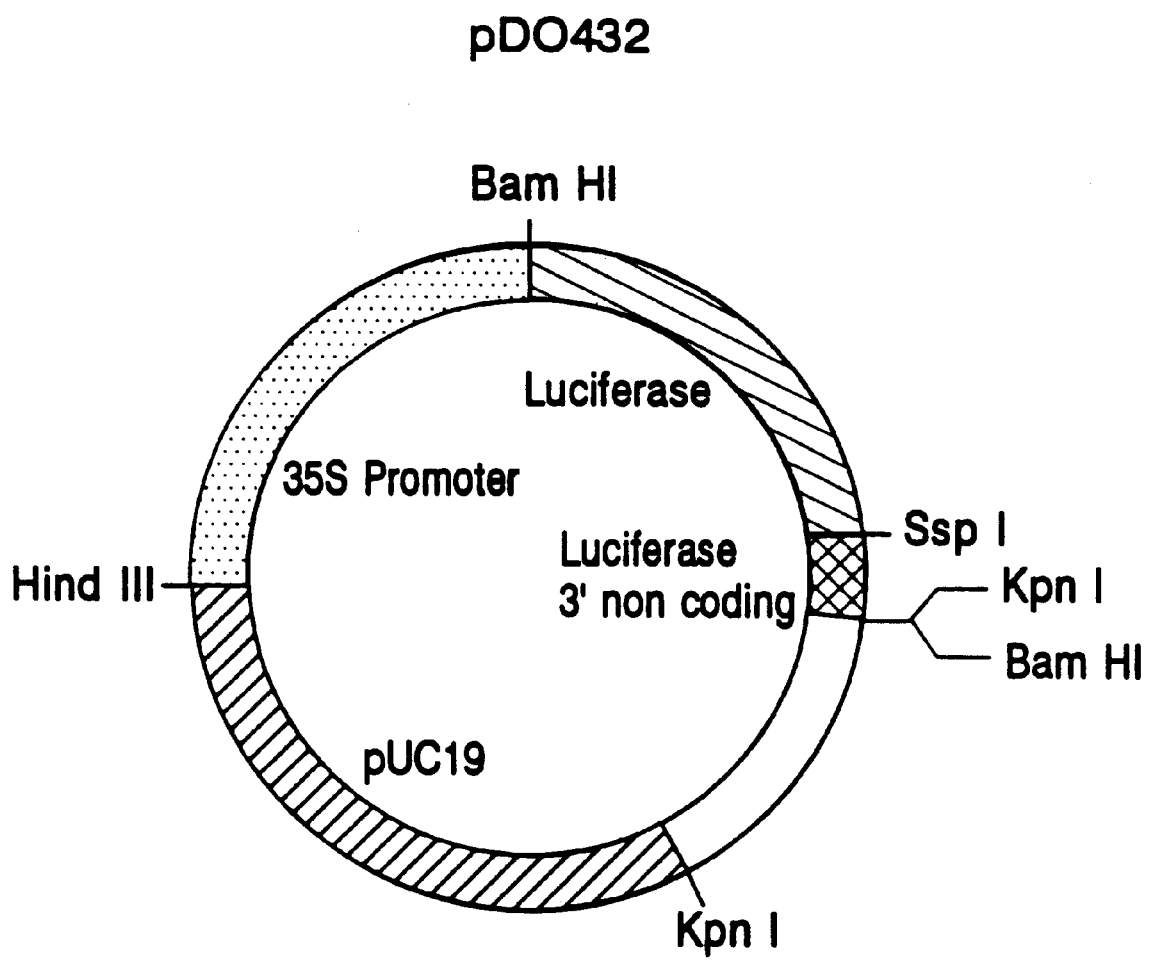
FIG. 1 is a partial restriction enzyme cleavage map of the plasmid pD0432 which contains the luciferase gene from the firefly, *Photinus pyralis*.
Figure 2:
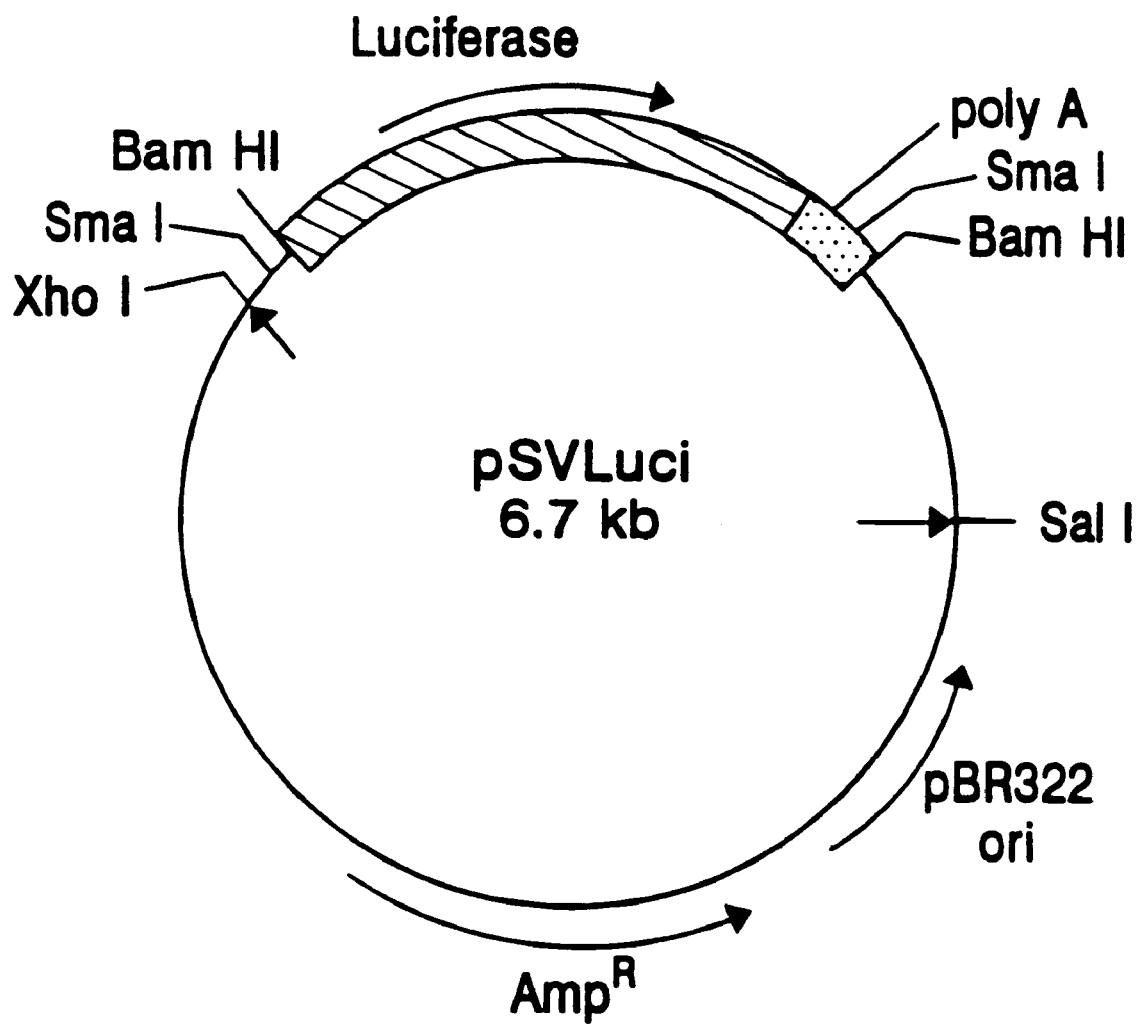
FIG. 2 is a partial restriction enzyme cleavage map of the plasmid pSVLuci which contains the luciferase gene from the firefly, *Photinus pyralis*.
Figure 3:
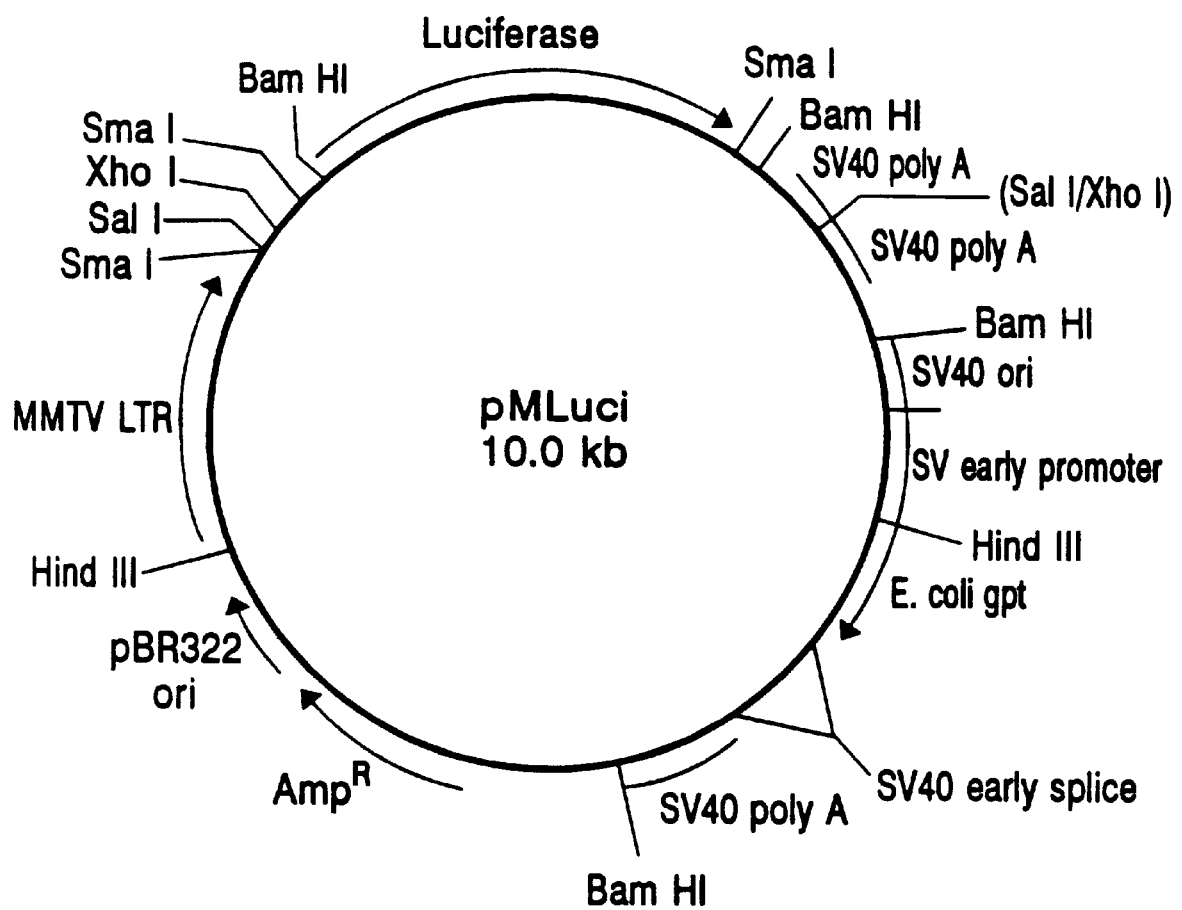
FIG. 3 is a partial restriction enzyme cleavage map of the plasmid pMLuci which contains the luciferase gene of the firefly, *Photinus pyralis* and the mouse mammary tumor virus long terminal repeat.

The firefly luciferase gene was removed from the plant expression plasmid pDO432 (33) (FIG. 1) as a 1.9 kb BamHI fragment and cloned into the BamHI site of pSVL (Pharmacia, Piscataway, N.J.), a mammalian expression vector containing the SV40 promoter. The resulting plasmid (pSVLuci; FIG. 2) was digested with XhoI and SalI to produce a 2.4 kb fragment containing the luciferase coding sequences and the SV40 late polyadenylation site. This fragment was inserted into the XhoI site of pMSG (Pharmacia, Piscataway, N.J.), a eukaryotic expression vector containing the MMTV promoter. The resulting MMTV promoter-luciferase fusion plasmid (pMLuci; FIG. 3) was used to transfect NIH/3T3 cells as described below (section E1). Similar constructs can be made using luciferase vectors from Clontech (Palo Alto, Calif.).

Figure 4:
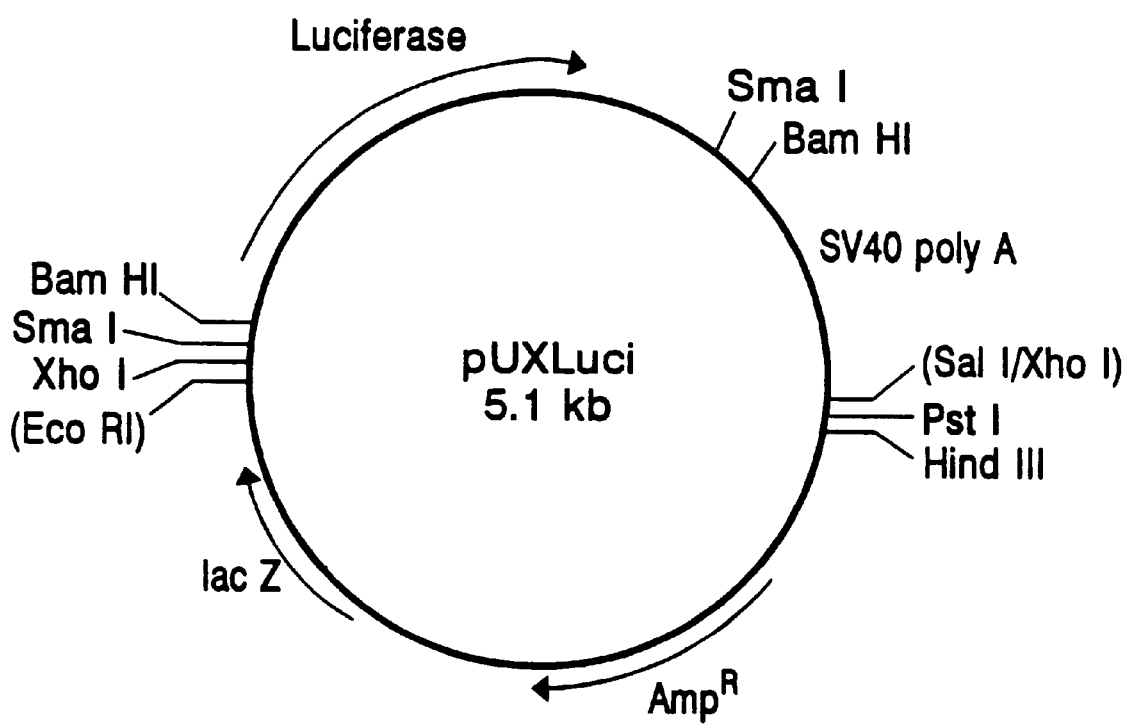
FIG. 4 is a partial restriction enzyme cleavage map of the plasmid pUXLuci which contains the luciferase gene from the firefly, *Photinus pyralis*.
Figure 5:
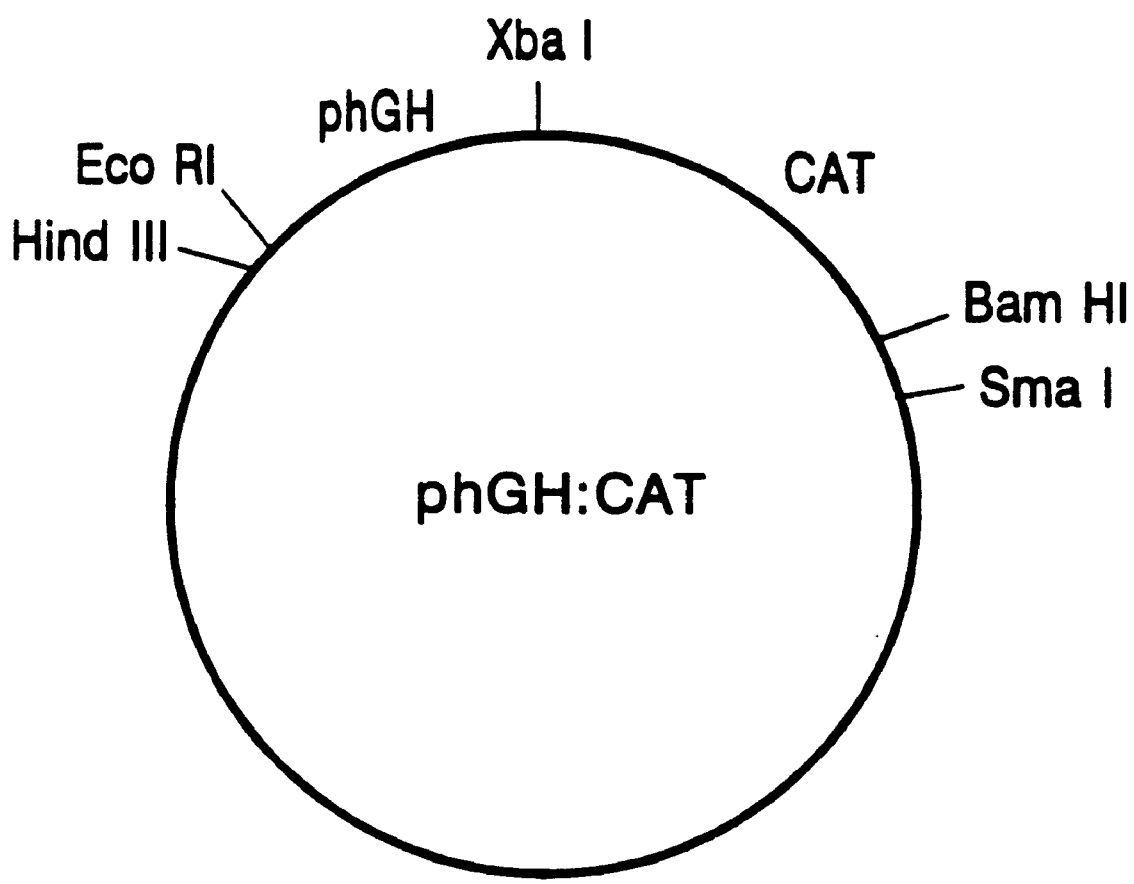
FIG. 5 is a partial restriction enzyme cleavage map of the plasmid phGH:CAT which contains the CAT gene and human growth hormone promoter sequences.
Figure 6:
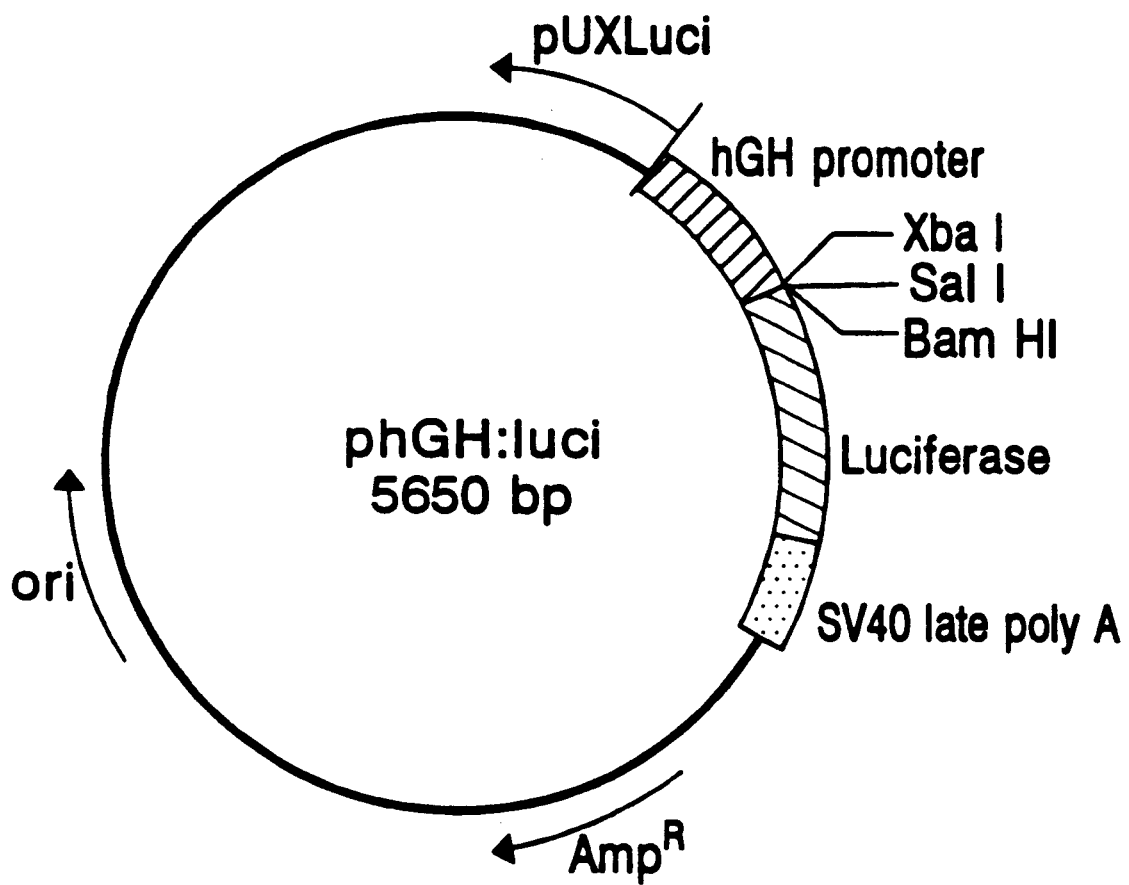
FIG. 6 is a partial restriction enzyme cleavage map of the plasmid phGH-Luci which contains the luciferase gene from the firefly, *Photinus pyralis* and human growth hormone promoter sequences.

2. Construction of the human growth hormone (hGH) promoter-luciferase fusion plasmid The SalI-XhoI fragment of pSVLuci (FIG. 2) containing the luciferase coding sequences and the SV40 late polyadenylation site was inserted into pUC 8 (Biorad, Richmond, Calif.), which had been linearized by a SmaI/HinCII digestion and ligated to XhoI linkers (New England Biolabs, Beverly, Mass.). The new plasmid thus generated (pUXLuci; FIG. 4) was linearized by XhoI digestion followed by incubation with the Klenow fragment of E. coli DNA polymerase and the four deoxyribonucleotides to fill in the single-stranded ends of the vector. This linear (5.1 KB) form of pUXLuci was then ligated to the filled-in 550 bP HindIII-XbaI fragment of the plasmid phGH:CAT (FIG. 5) (25). Human growth hormone promoter sequences located on the HindIII-XbaI fragment were thus fused to the luciferase coding sequences located on pUXLuci generating the plasmid phGH-Luci (FIG. 6), which was used in transfections of GC cells as described below (Section E2).

3. Construction of the human Granulocyte-Colony stimulating factor (hG-CSF) Promoter-Luciferase fusion plasmid (pG-Lucl)

Figure 7:
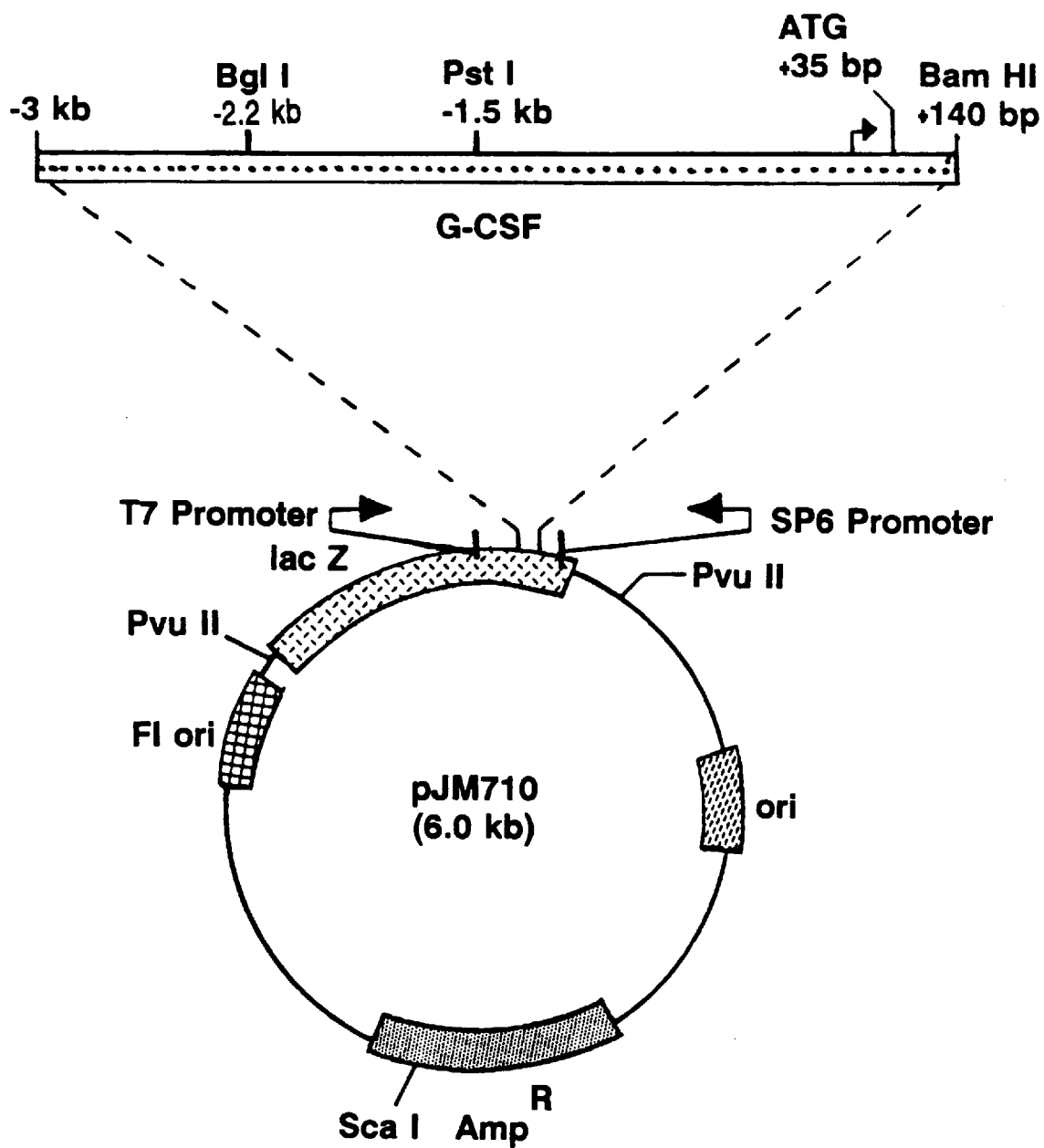
FIG. 7 is a partial restriction enzyme cleavage map of the plasmid pJM710 which contains G-CSF upstream sequences.
Figure 8:
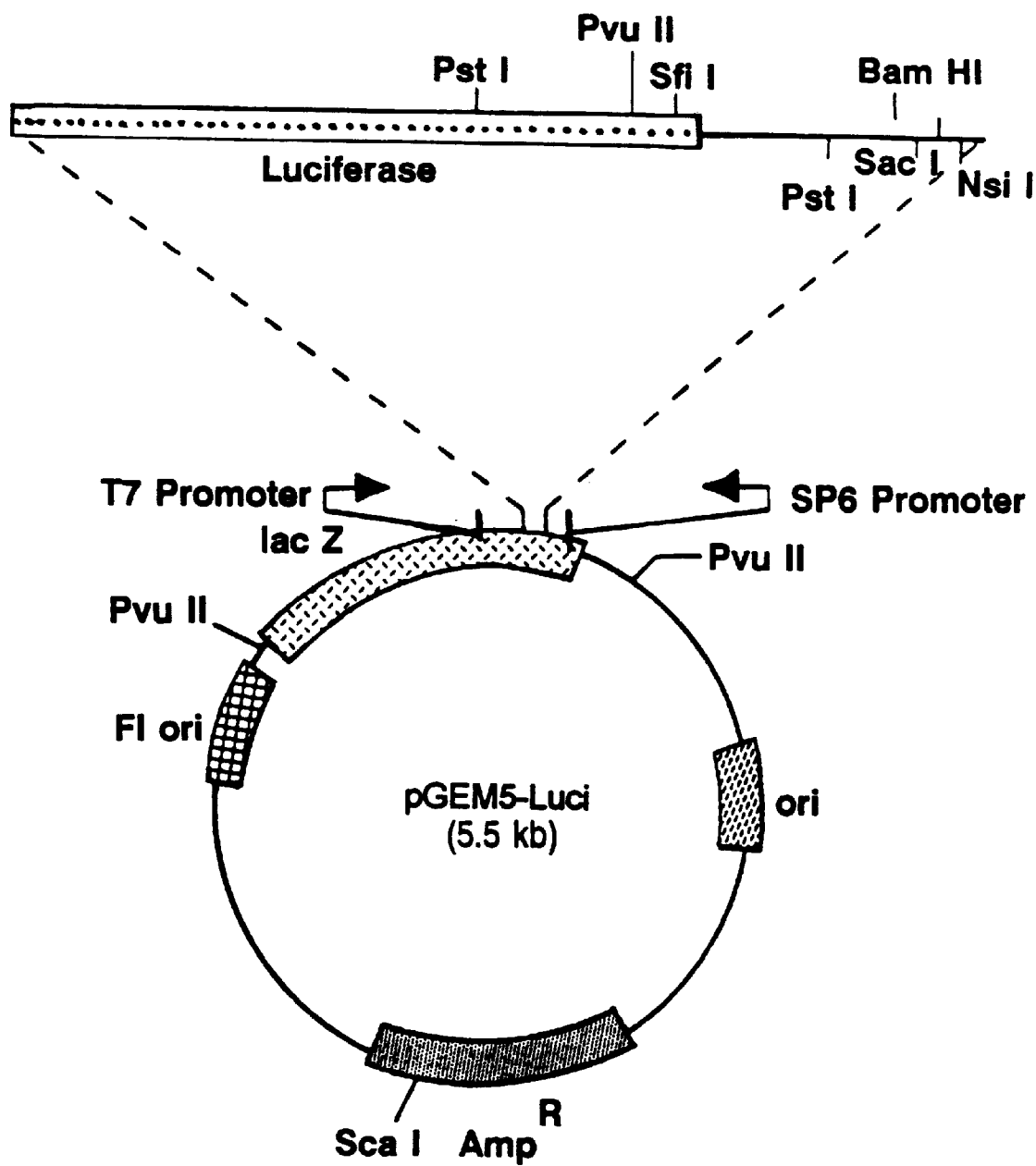
FIG. 8 is a partial restriction enzyme cleavage map of the plasmid pGEM5-Luci which contains the luciferase gene from the firefly, *Photinus pyralis*.
Figure 9:
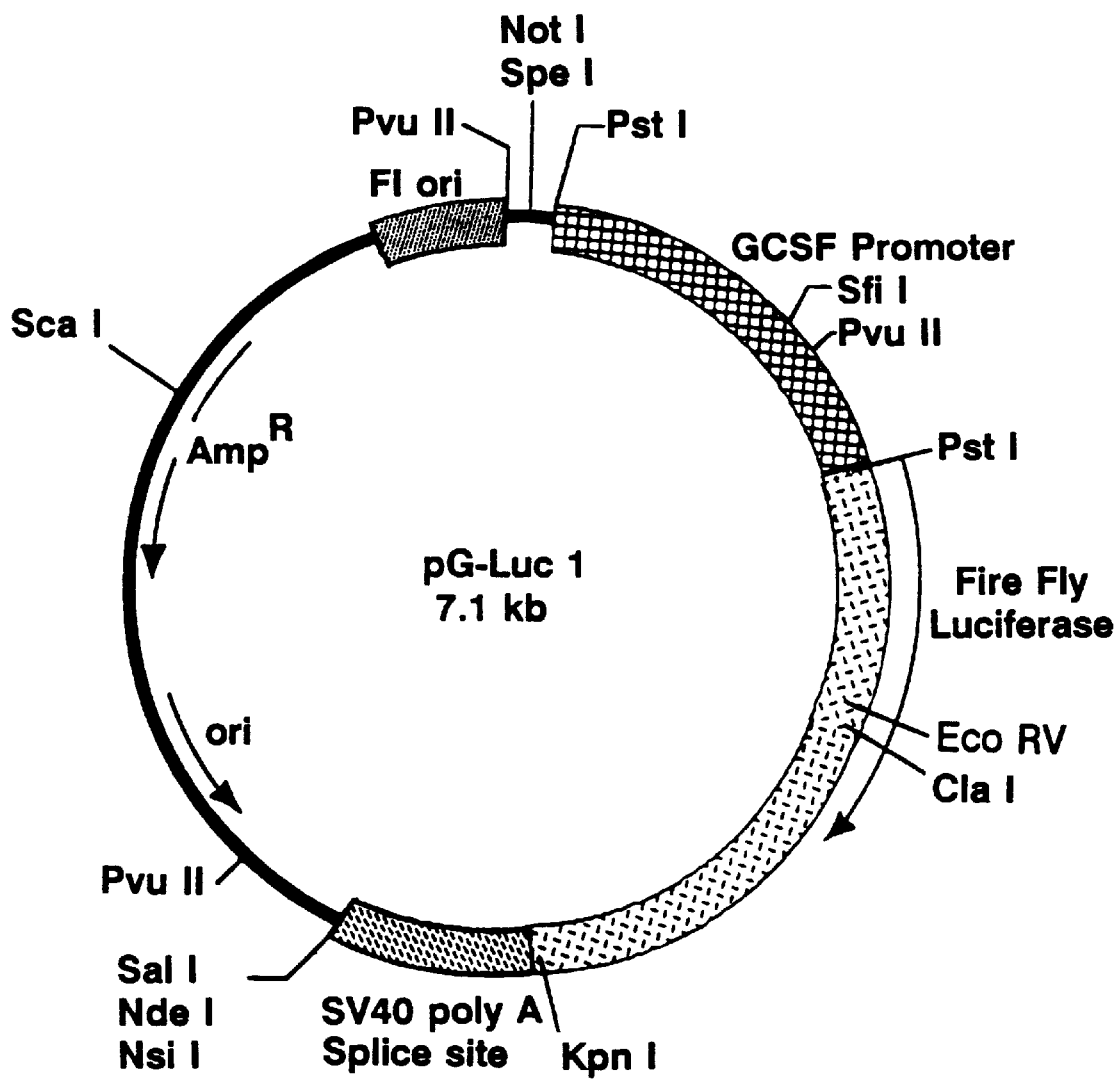
FIG. 9 is a partial restriction enzyme cleavage map of the plasmid PG-Luc 1 which contains both the luciferase gene from the firefly, *Photinus pyralis*, and G-CSF upstream sequences.

Information on the G-CSF upstream and coding sequences was published by Nagata et al. (1986) and was used to synthesize 5 oligonucleotide probes (OL-1 to OL-5) to screen a human leukocyte genomic DNA library (Clontech, Palo Alto, Calif.) according to the supplier's instructions. The sequences of the oligonucleotide probes were:

5' GCTTTTTGTTCCAACCCCCCTGCATT 3' (OL-1);

5' CCCTGCATTGTCTTGGACACCAAAT 3' (OL-2);

5' GCGCTCCAGGAGAAGCTGGTGAGT 3' (OL-3);

5' AAGCTGATGGGTGAGTGTCTTGGC 3' (OL-4);

5' ATCAGCGGCTCAGCCTTCTT 3' (OL-5);

The sequences of OL-1, OL-2 and OL-5 recognize the G-CSF promoter region, OL-4 recognizes the first intron/exon junction and OL-3 recognizes sequences within the second exon (32). One of the clones isolated from the leukocyte library using these oligonucleotide probes contains a 3.5 kb SalI-BamHI fragment of G-CSF genomic sequence consisting of 3.3 kb of promoter sequence and two hundred base pairs of the coding region. This fragment was inserted into the vector pGEM-7-Zf (Promega, Madison, Wis.) which had previously been digested with SalI/BamHI, resulting in the vector pJM710 (FIG. 7). pJM710 was then digested with PstI, and the resulting 1.6 kb fragment containing G-CSF upstream sequences and the first 15 bases of the G-CSF leader sequence was inserted into the PstI site of pGEM5-Luci (FIG. 8) to generate pG-Lucl (FIG. 9). This construct was then used for transfections of 5637 human bladder carcinoma cells as described below in section E3. pGEM5-Luci (FIG. 8) had previously been constructed by inserting the XbaI/SalI fragment from pSVLuci (FIG. 2) containing the luciferase coding sequence and the SV40 late polyadenylation signal into pGEM5-Zf (Promega, Madison Wis.) digested with XhoI/SalI.

C. Construction of the OSI Mammalian Expression Shuttle Vector

Figure 10:
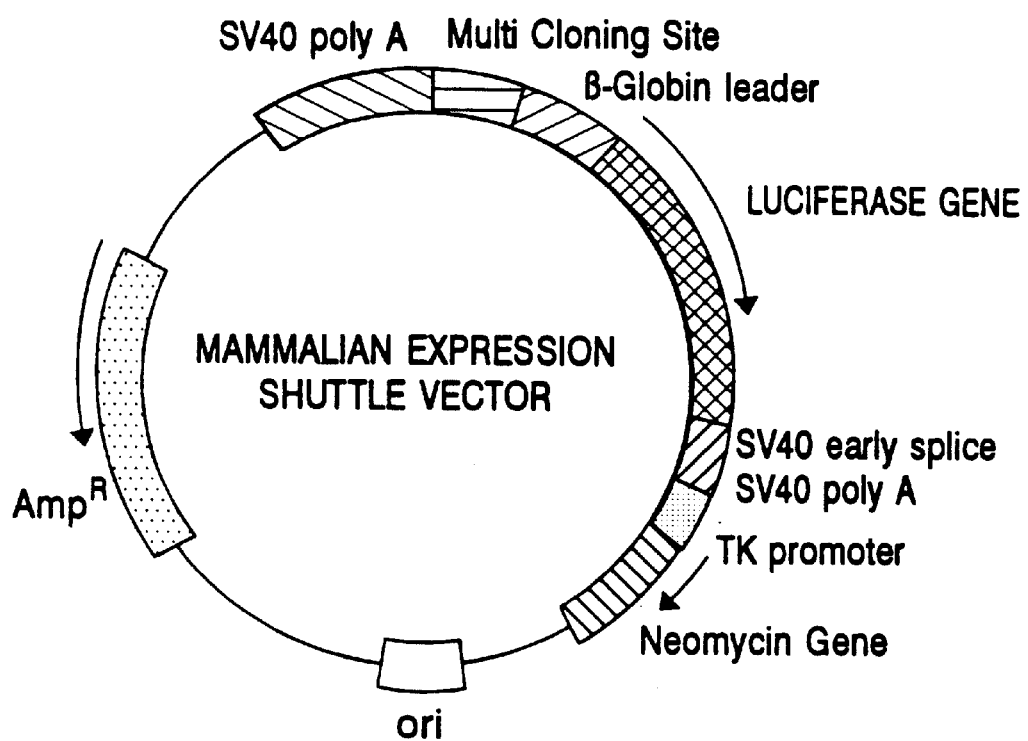
FIG. 10 is a view of the mammalian expression shuttle vector pUV102 with its features. The mammalian expression shuttle vector was designed to allow the construction of the promoter-reporter gene fusions and the insertion of a neomycin resistance gene coupled to the herpes simplex virus thymidine kinase promoter (TK-NEO).

A mammalian expression shuttle vector was designed to allow the construction of the promoter-reporter gene fusions to be used in high-throughput screens to identify transcriptionally modulating chemicals. Features of the plasmid are shown in FIG. 10. The shuttle vector was constructed in several steps. Initially six oligonucleotides (pUV-1 through pUV-6) were synthesized see FIG. 11a for sequence). The sequences of pUV-1, pUV-2 and pUV-3 correspond to a multicloning site, the b-globin leader sequence and the first 53 bases of the firefly luciferase coding region. The sequences of pUV-4, pUV-5 and pUV-6 are complementary to the first three oligonucleotides. The pUV oligonucleotides were annealed, ligated and inserted into the SalI/EcoRI sites of pTZ18R (Pharmacia, Piscataway N.J.) (FIG. 11(b)). The resulting vector was then digested with SmaI/PvuII and the oligonucleotide containing fragment was cloned into the bluescript KS(+) plasmid (Stratagene, La Jolla, Calif.), previously digested with PvuII, to yield pUV001 (FIG. 11(b)). Several fragments were ligated into pUV001 to create pUV100. The luciferase coding sequences (except first 53 bases) and polyadenylation site were obtained as a 1.8 kilobase XbaI/XmaI fragment from pMLuci (section B-1, FIG. 3). The SV40 early splice site and the SV40 late polyadenylation site were obtained as an 871 bp XmaI/ BamHI fragment from pMSG (Pharmacia, Piscataway N.J., FIG. 12). Both DNA fragments were cloned into pUV001, previously digested with XbaI/BamHI to yield pUV100 (FIG. 12).

Figure 13:
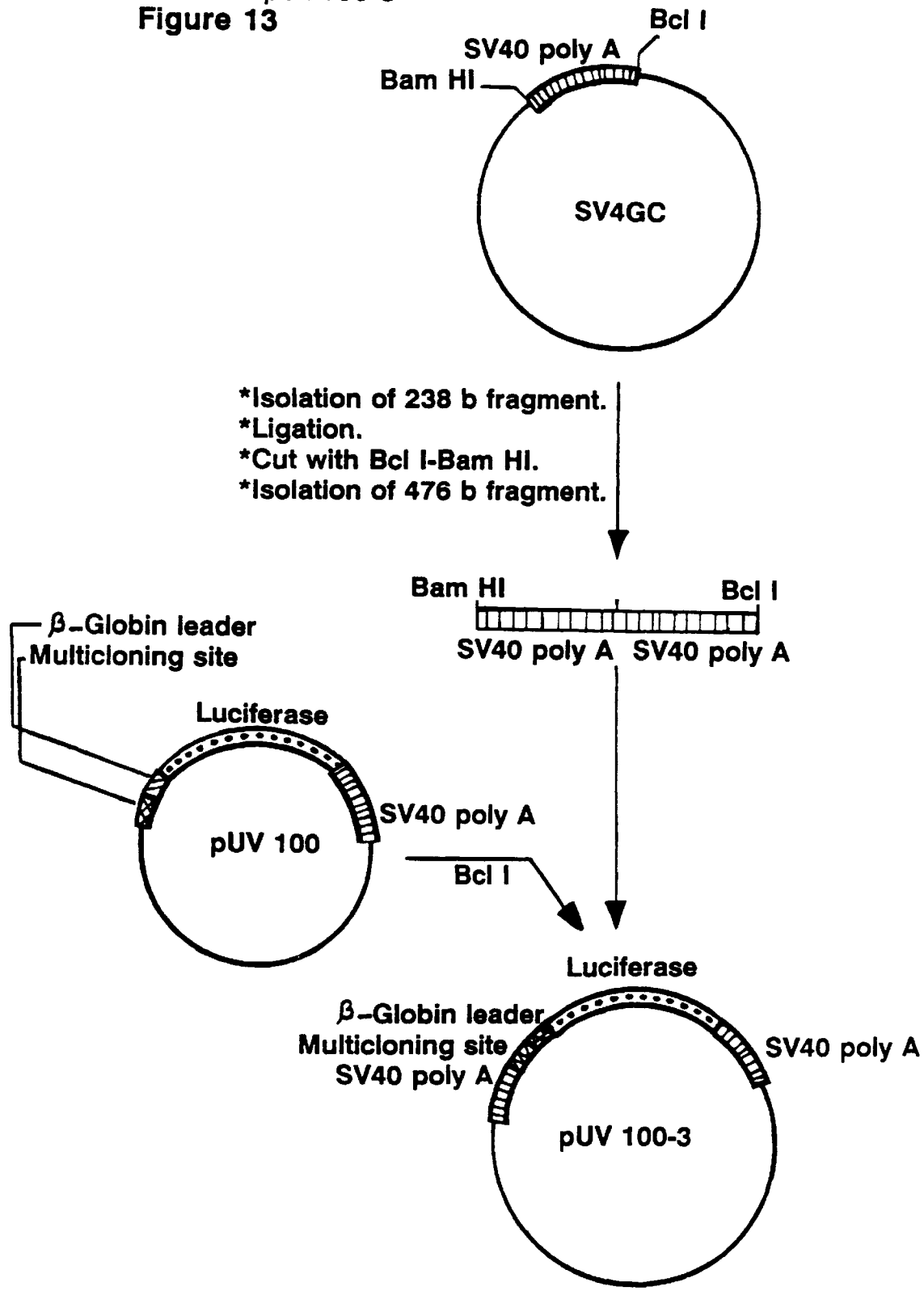
FIG. 13 is a diagrammatic representation of the construction of the plasmid pUV100-3 from the plasmid pUV100 and a 476 b fragment containing a dimeric SV40 polyadenylation site.

A 476 b fragment containing a dimeric SV40 polyadenylation site was then cloned into the BclI site of pUV100 (FIG. 13). To do this, a 238 bp BlcI/BamHI fragment was obtained from SV40 genomic DNA (BRL), ligated, digested with BclI/BamHI, gel isolated, and inserted into pUV100, resulting in the vector pUV100-3 (FIG. 13). Linkers containing one SfiI and one NotI restriction site were then cloned into the PvuII/BamHI sites of pUV100-3. Two sets of linkers were synthesized containing the SfiI site in opposite orientations (oligonucleotides D-link1 and D-link2 and oligonucleotides R-link1 and R-link2). The sequences of the oligonucleotides were:

5' GATCGGCCCCTAGGGCCGCGGCCGCAT 3' (D-link1)

5' ATGCGGCCGCGGCCCTAGGGGCC 3' (D-link2)

5' GATCGGCCCTAGGGGCGGCCGCAT 3' (D-link1)

5' ATGCGGCCGCGGCCCCCTAGGGCC 3' (R-link2)

Figure 14:
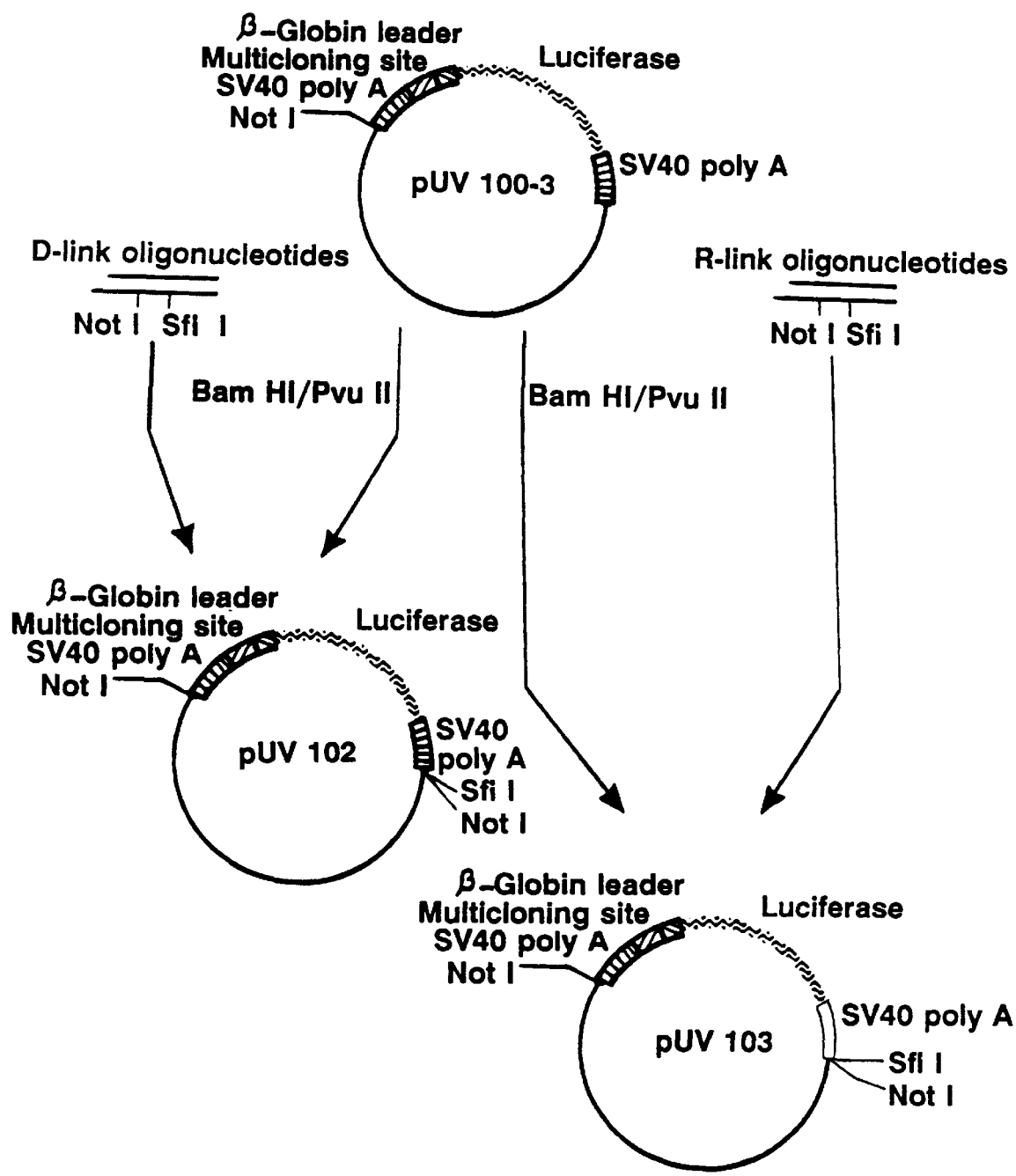
FIG. 14 is a diagrammatic representation of the construction of the plasmids pUV102 and pUV103 from the plasmid pUV100-3 and D-link oligonucleotides and the plasmid pUV100-3 and R-link oligonucleotides, respectively.

The plasmid that contains D-link oligonucleotides was named pUV102 and the plasmid that contains R-link oligonucleotides was named pUV103 (FIG. 14).

Figure 16:
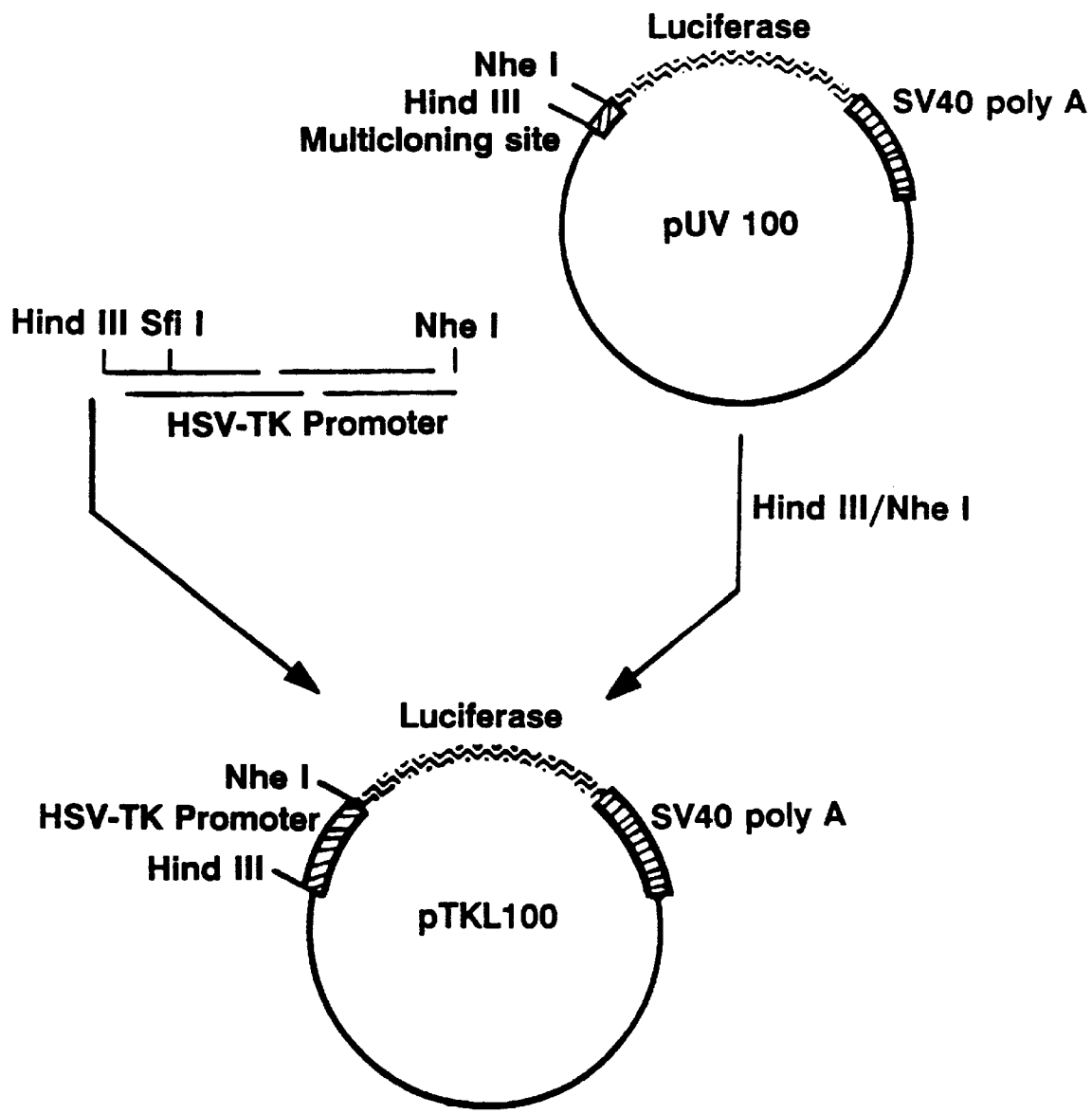
FIG. 16 is a diagrammatic representation of the construction of the plasmid pTKL100 which contains the luciferase gene from the firefly, *Photinus pyralis* and the HSV-TK promoter sequence.
Figure 17:
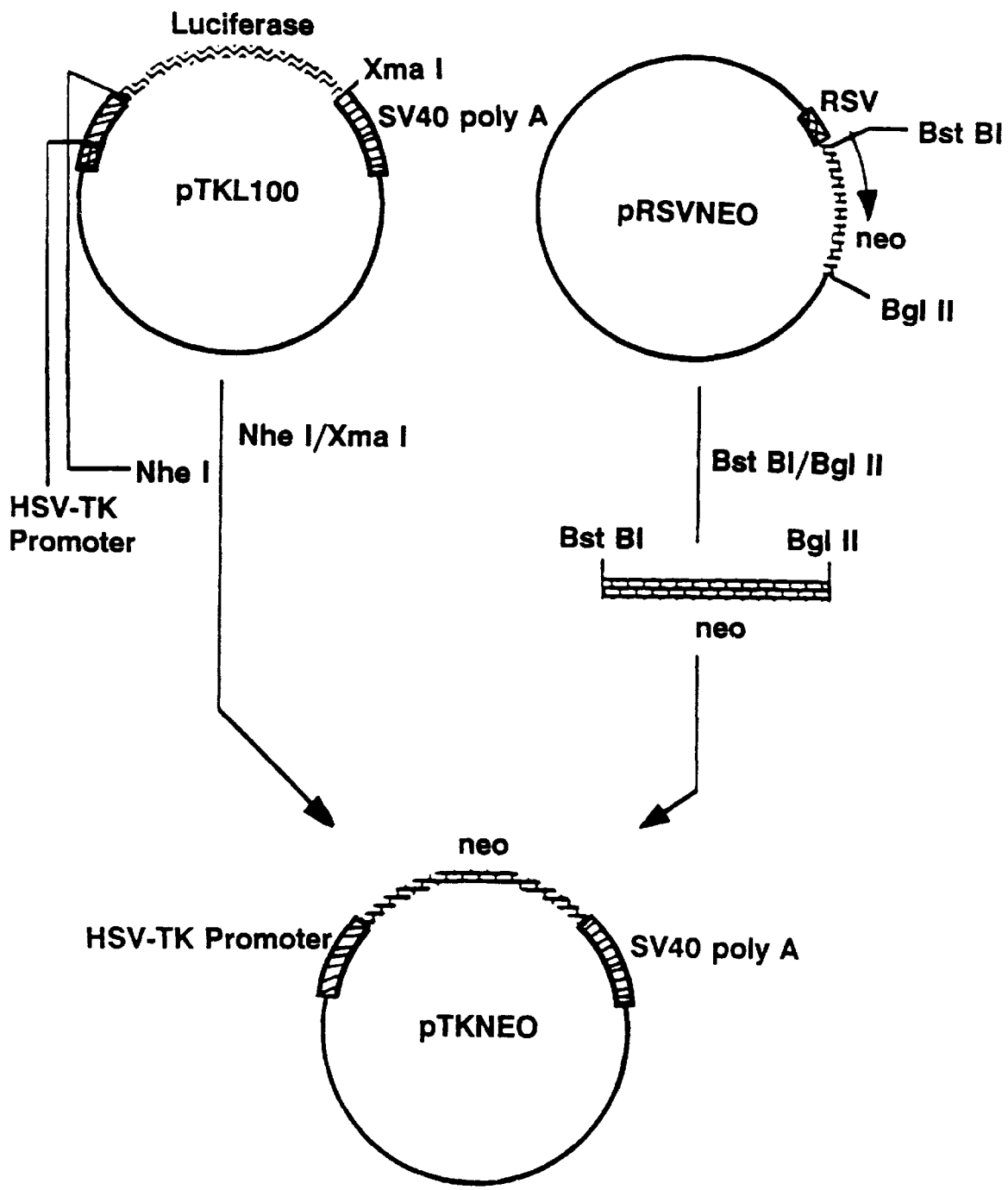
FIG. 17 is a diagrammatic representation of the construction of the plasmid pTKNEO which contains the neo gene, from about 3.5 kg NheI/XmaI fragment from pTLK100, and the about 0.9 kg BstBI/BGlII fragment containing the neo coding region from pRSVNEO.
Figure 18:
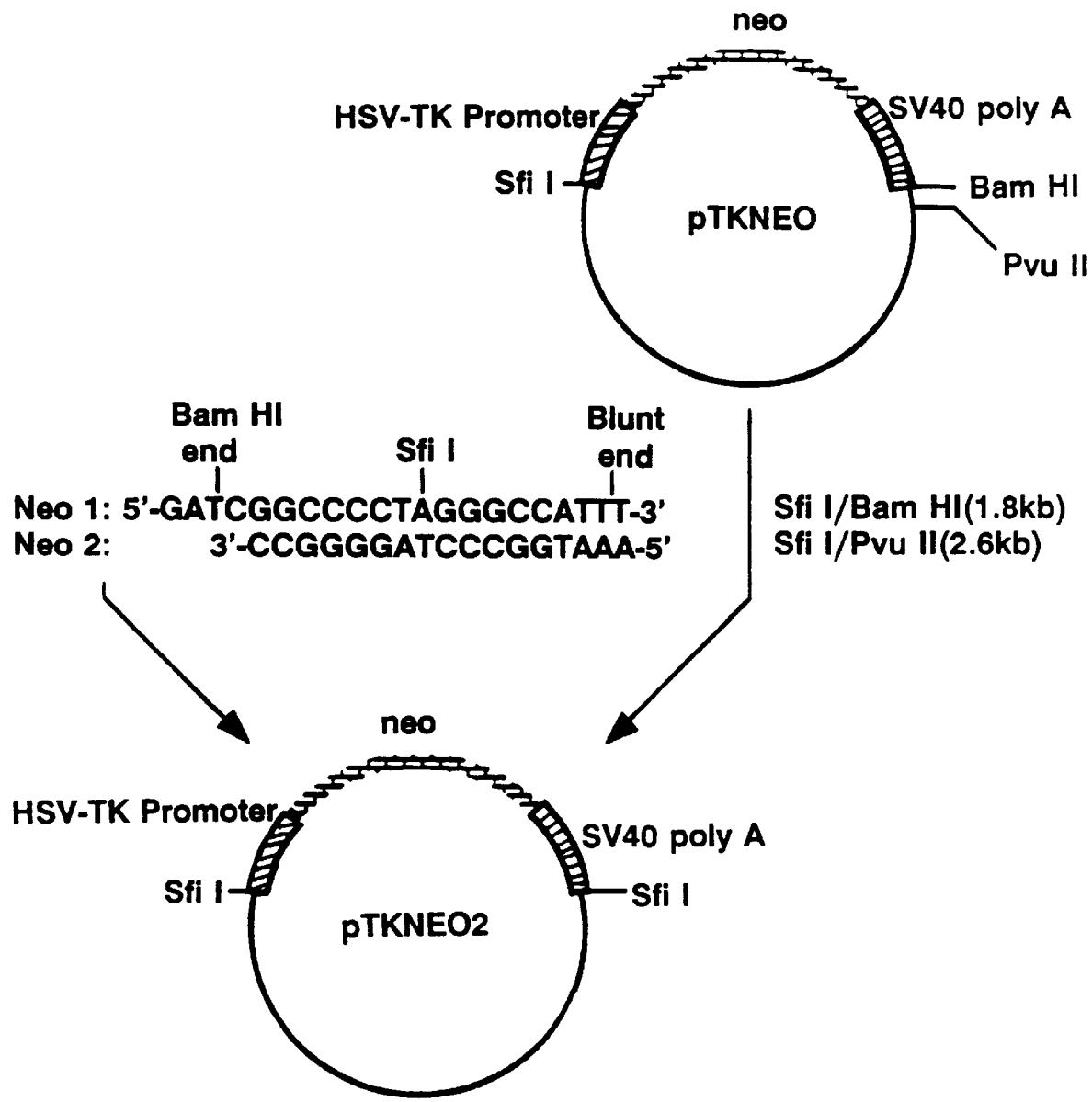
FIG. 18 is a diagrammatic representation of the construction of the plasmid pTKNEO2 from the plasmid pTKNEO and the oligonucleotides Neo 1 and 2.
Figure 19:
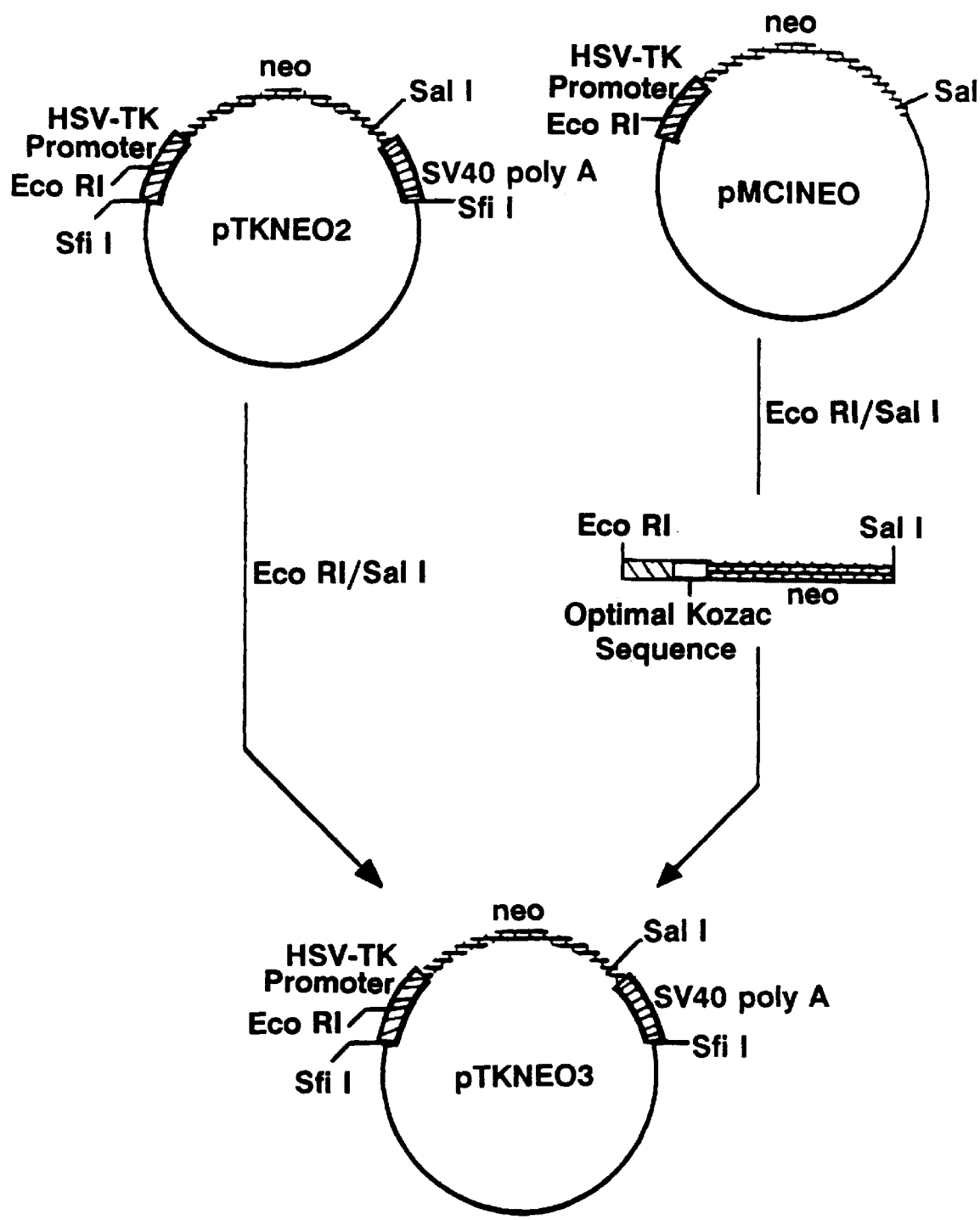
FIG. 19 is a diagrammatic representation of the construction of the plasmid pTKNEO3 from the plasmid PTKNEO2 and about 0.9 kb EcoRl/SalI fragment from pMC1NEO.

The neomycin resistance gene (neo) was then placed under control of the Herpes Simplex Virus thymidine kinase (HSV-TK) promoter to generate a resistance cassette which is free of known enhancer sequences. To do this the HSV-TK promoter was synthesized using four oligonucleotides (FIG. 15) designed according to published sequence information (31), and including an SfiI restriction site 5' of the HSV-TK sequences. These oligonucleotides were phosphorylated, annealed, ligated and inserted into pUV100 digested previously with HindIII/NheI, generating the vector pTKL 100 (FIG. 16). After verifying the HSV-TK sequence, the about 3.5 kb NheI/SmaI fragment was isolated from pTKL100, and the about 0.9 kb BstBI/BglII fragment containing the neo coding region was isolated from pRSVNEO (14). These two fragments were filled in with Klenow polymerase and ligated to form pTKNEO (FIG. 17). An additional SfiI site was then inserted 3' of the neo gene by isolating the about 1.8 kb SfiI/BamHI and about 2.6 kb SfiI/PVUII fragments of pTKNEO and conducting a three way ligation along with a synthesized SfiI oligonucleotide generating pTKNEO2 (FIG. 18). The HSV-TK/NEO vector containing an optimized Kozac sequence was also utilized (Stratagene, La Jolla, Calif., pMC1NEO). An additional vector was constructed by replacing the about 0.9 kb EcoRI/SalI fragment of pTKNEO2 with the about 0.9 kb EcoRI/SalI fragment from pMC2NEO. This vector was termed pTKNEO3. (FIG. 19).

D. Molecular Cloning of Hematopoietic Promoters and Insertion into the OSI Mammalian Expression Shuttle Vector 1. Strategy This section describes: (a) the molecular cloning of transcriptionally modulatable regulatory sequences of several genes of interest (in this case members of the family of hematopoietic growth factors) and (b) the making of constructs where these regulatory sequences now control the expression of the luciferase gene. To make such constructs, several kilobases of sequence upstream of the transcription start site, along with 5' untranslated sequences up to the translation start site (ATG), of a gene of interest were inserted 5' of the luciferase coding region. In this way constructs can be made where all sequences upstream of their translation start site are from the gene of interest, and all coding sequences are from the luciferase gene. How this was accomplished for the hematopoietic growth factor genes is described in sections D2-6.

2. Human Granulocyte-Macrophage Colony Stimulating Factor (GM-CSF)

Figure 20:
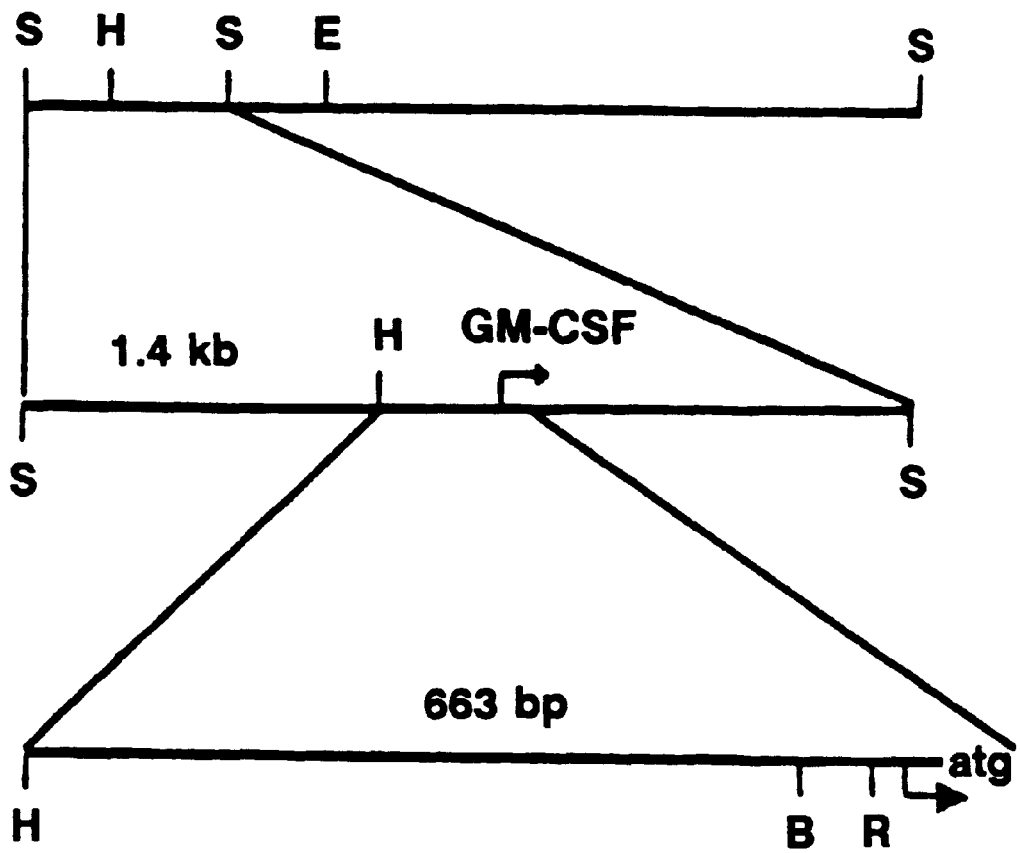
FIG. 20 is a partial restriction enzyme cleavage map of a human genomic clone which contains the entire GM-CSF coding region.

Cloning of GM-CSF promoter sequences was performed by using oligonucleotide probes based on the GM-CSF genomic sequence (20). Two DNA oligonucleotide probes were synthesized, one corresponding to GM-CSF sequences 5' of the coding region (5' GGTGACCACAAAATGC-CAGGGAGGCGGG 3') and the other to sequences in the first exon (5' GCAGGCCACAGTGCCCAAGAGACAG-CAGCAGGCT 3'). The oligonucleotide probes were used to screen a human leukocyte cell genomic DNA library (Clontech, Palo Alto, Calif.) following the manufacturer's instructions. One clone was obtained which contains the entire GM-CSF coding region along with 2 kb of upstream sequences (see FIG. 20).

Figure 23:
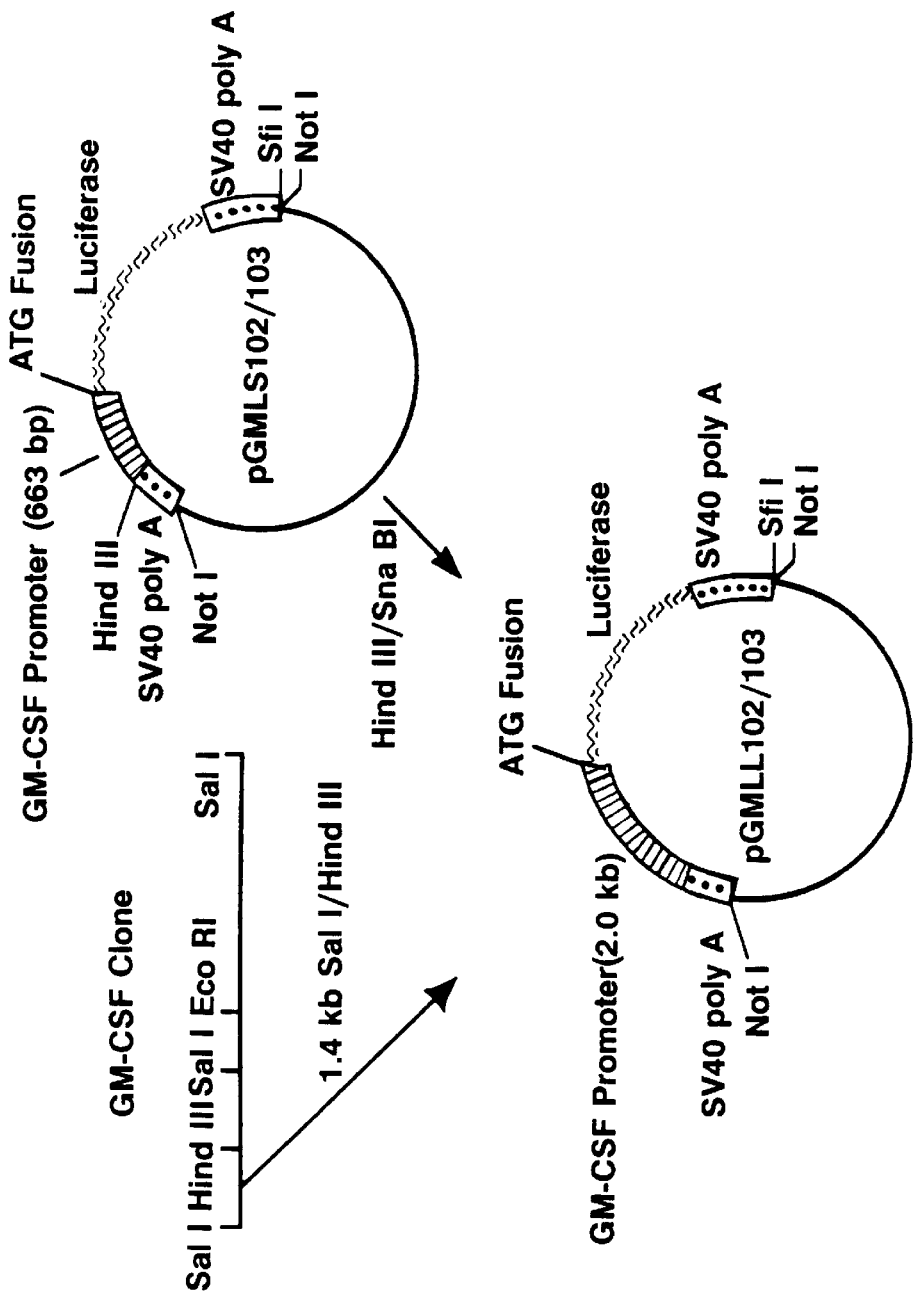
FIG. 23 is a diagrammatic representation of the construction of plasmids pGMLL102 and pGMLL103 from the plasmid pGMLS102 and the GM-CSF clone and the plasmid pGMLS103 and the GM-CSF clone, respectively.

All routine subcloning procedures were performed as described by Maniatis et al. (1982), (28) unless otherwise noted. The about 0.7 kb HindIII/RsaI fragment of the GM-CSF clone (FIG. 20) was inserted into pUC 18 previously digested with HindIII/HincII. The about 0.7 kb HindIII/SmaI fragment was then isolated from the resulting vector and cloned into pUV 100 digested previously with HindIII/SnaBI, thereby generating pGMLUCI (FIG. 22.) In order to correctly fuse the GM-CSF ATG with the coding region of luciferase, four oligonucleotides (FIG. 21) were synthesized, phosphorylated, annealed, ligated, and inserted into pUC19 previously digested with Eco RI/XbaI, generating pGM-1 (FIG. 22). pGM-1 was then sequenced (Sequenase Kit, US Biochemicals, Cleveland, Ohio) using the M13 forward (U.S. Biochem.) and reverse primers (Pharmacia, Piscataway, N.J.) to ensure that there were no mutations in the synthesized oligonucleotides. The about 1.8 kb BstEII/ScaI fragment from pGM-1 was then isolated and ligated to about 1.5 kb BstEII/ScaI fragment from pGM-LUCI to generate pGM-2 (FIG. 22). pGM-2 was then digested with Hind III/XbaI and about 0.7 kb fragment was cloned into pUV 102 and pUV 103 previously digested with HindIII/XbaI. This generated pGMLS102 and pGMLS103 (FIG. 22), which contain 663 bp of GM-CSF sequence 5' of the ATG fused directly to the second (correct) ATG of luciferase and the rest of the luciferase coding region. An additional about 1.4 kb of upstream sequences were cloned into this construct by isolating the about 1.4 kb SalI/HindIII fragment from the GM-CSF clone (FIG. 20), blunting the SalI end by filling in with Klenow polymerase, and inserting the fragment into pGMLS102 and pGMSL103 previously digested with HindIII/SnaBI. This step generated pGMLL102 and PGMLL103, respectively (FIG. 23). Finally, the pTKNEO2 and PTKNEO3 about 1.8 kb SfiI fragments were cloned directly into the SfiI site of pGMLL103 to generate pGMLL103 NEO2 and pGMLL103 NEO3.

3. Human Macrophage Colony Stimulating Factor (M-CSF or CSF-1)

Sequence information on the M-CSF gene (23) was used to synthesize an oligonucleotide probe (CSF1-a) to screen a human leukocyte genomic DNA library (Clontech, Palo Alto, Calif.) according to the supplier's instructions. The sequence of the oligonucleotide probe was:

5' CCGGCGCGGTCATACGGGCAGCTGG 3' (CSF1-a)

Figure 24:
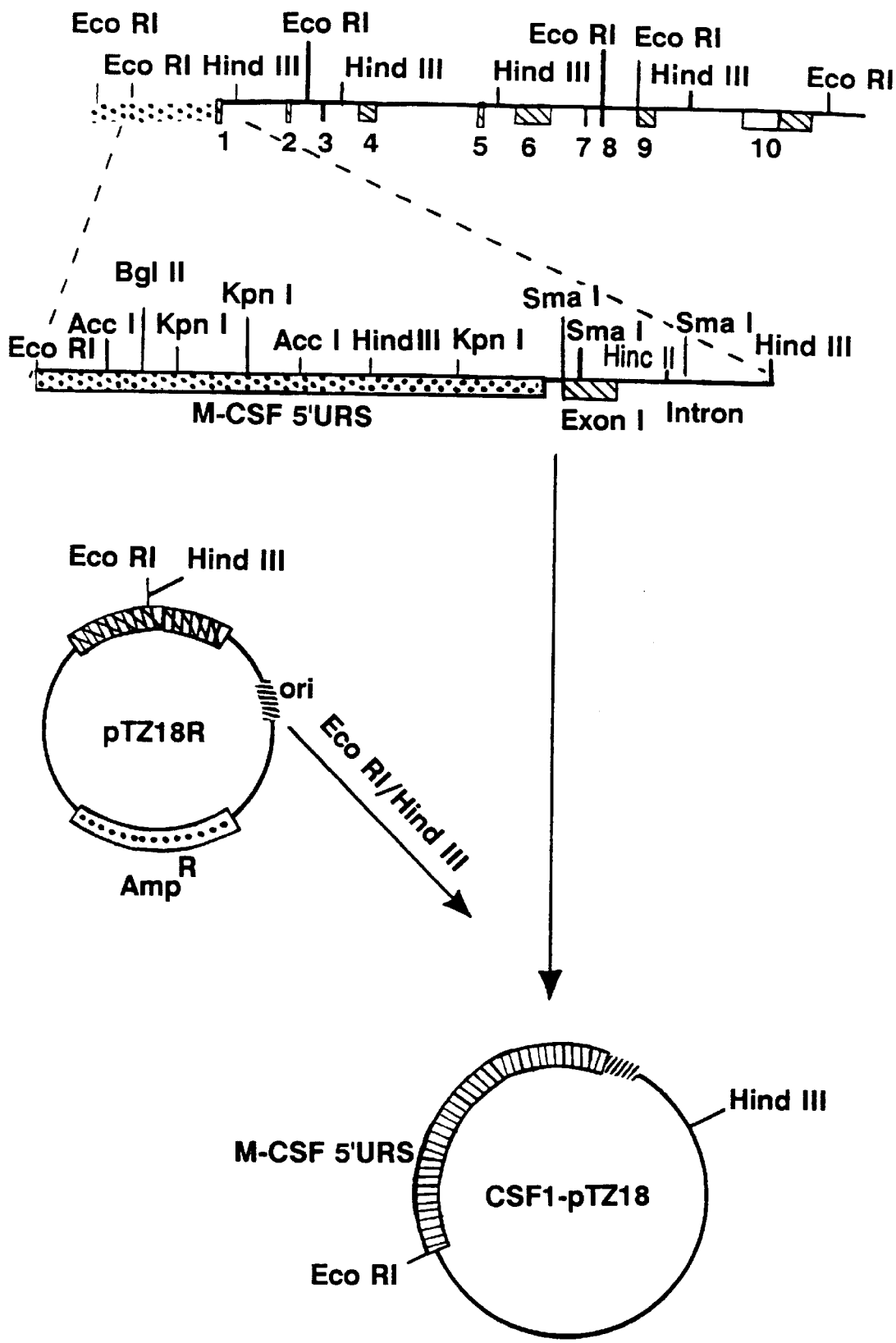
FIG. 24 is a diagrammatic representation of the construction of the plasmid CSF1-pTZ18 from the plasmid pTZ18R and a gene fragment comprising the first exon and 5' flanking region of M-CSF.
Figure 25:
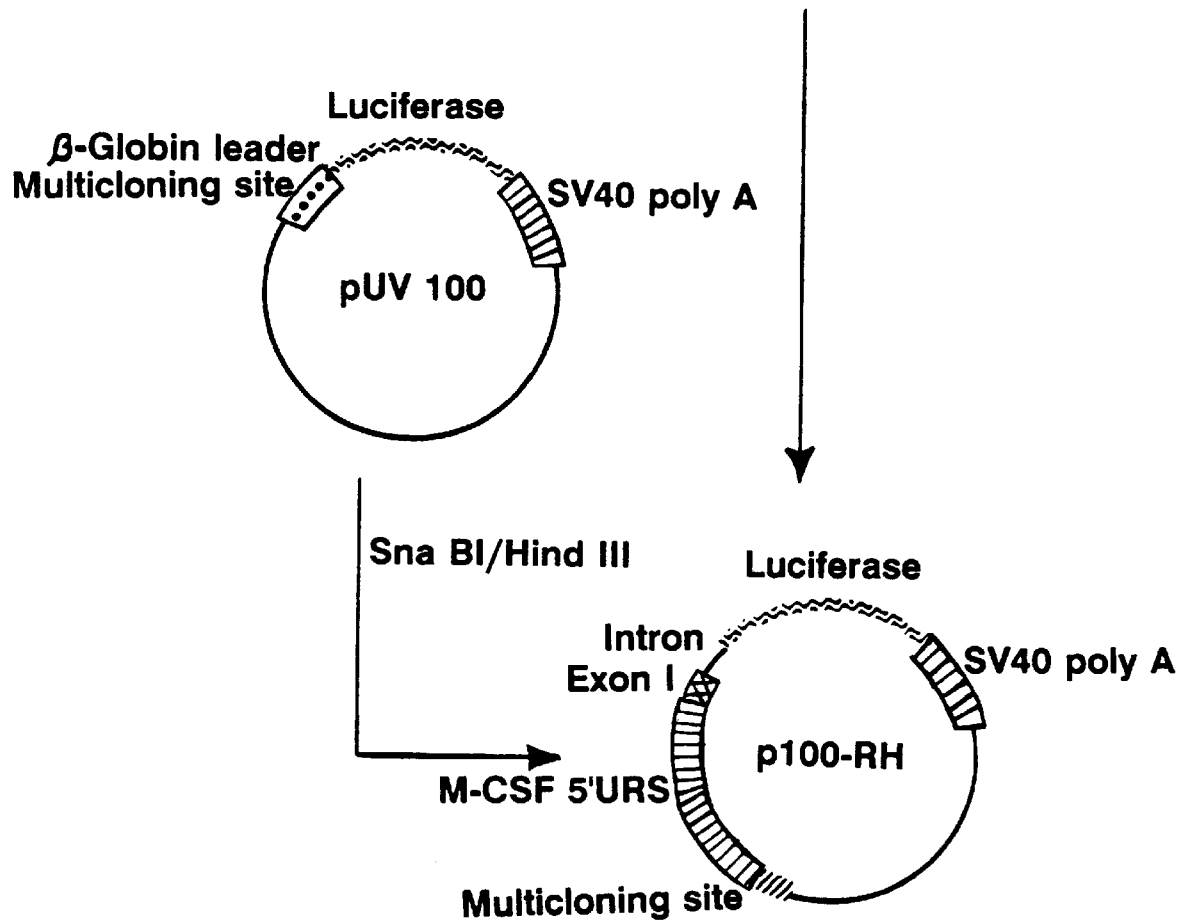
FIG. 25 is a diagrammatic representation of the construction of the plasmid p100-RH from the plasmid pUV100 and the gene fragment comprising the first exon and 5' flanking region of M-CSF from the plasmid

The sequence of this probe corresponds to sequences within the second exon of the M-CSF gene. One of the clones isolated from the leukocyte library contains a 5 kb EcoRI/HindIII fragment which includes the first exon and 5' flanking region of M-CSF. This fragment was inserted into the pTZ18R vector (Pharmacia, Piscataway N.J.) which had been previously digested with EcoRI/HindIII resulting in the vector CSF1-pTZ18 (FIG. 24). The same fragment was isolated from CSF1-pTZ18, blunt ended at the EcoRI end, and inserted into the pUV100 vector which had been previously digested with SnaBI/HindIII, resulting in the vector p100-RH (FIG. 25). The M-CSF untranslated leader sequence (23) was then fused to the first codon of the luciferase coding region as follows: (a) a 740 bp PstI/PvuII fragment was isolated from CSF1-pTZ18 containing 570 bp of the M-CSF promoter and 170 bp of the untranslated leader sequence; (b) oligonucleotides containing sequences from the 3' end of the M-CSF leader sequence and the 5' end of the luciferase coding region were synthesized:

5' CTGCCCGTATGGA 3' (CSF-luci5)

Figure 11B:
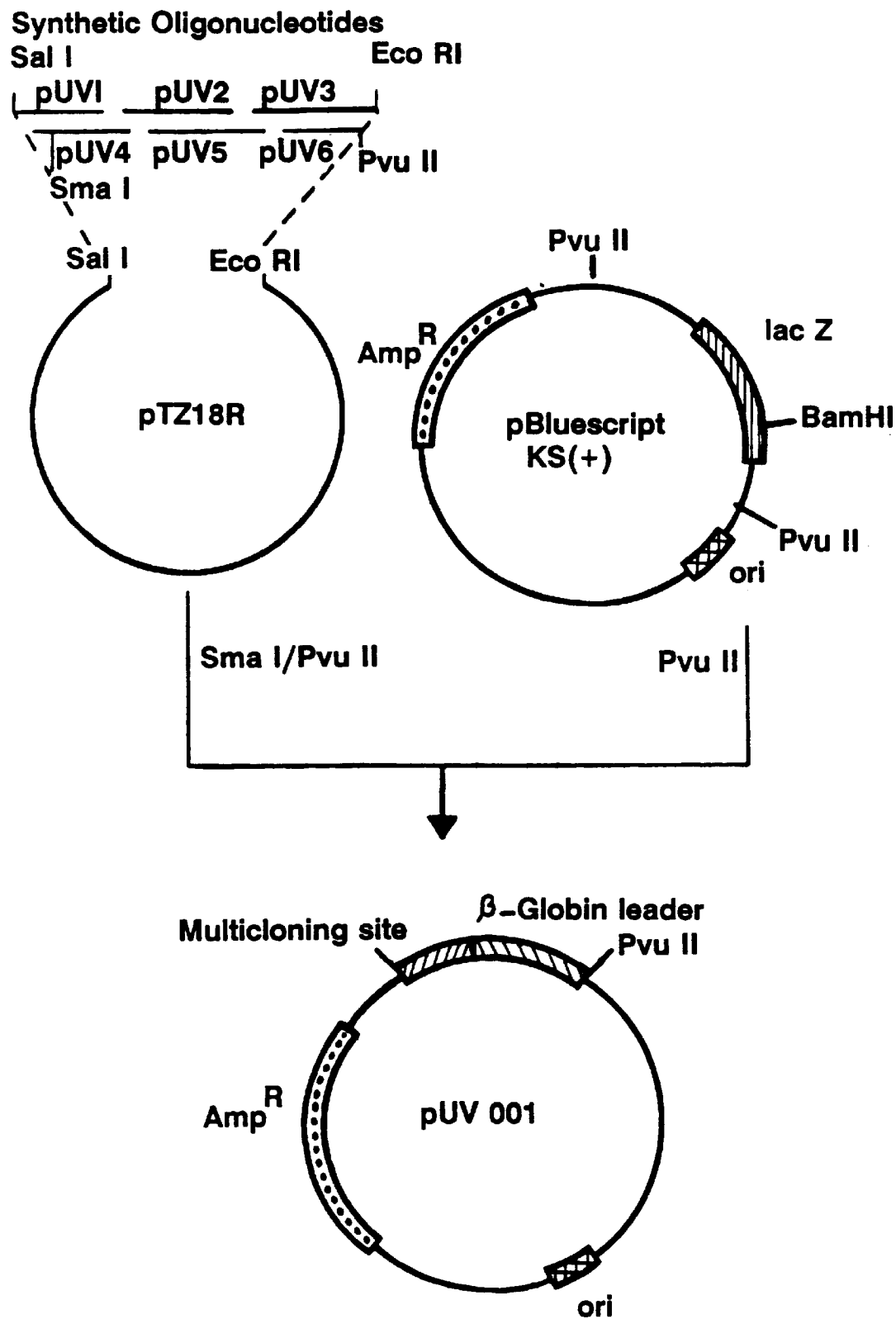
FIG. 11b is a diagrammatic representation of the construction of the plasmid pUV001 from the plasmids pTZ18R and pBluescript KS(+).
Figure 12:
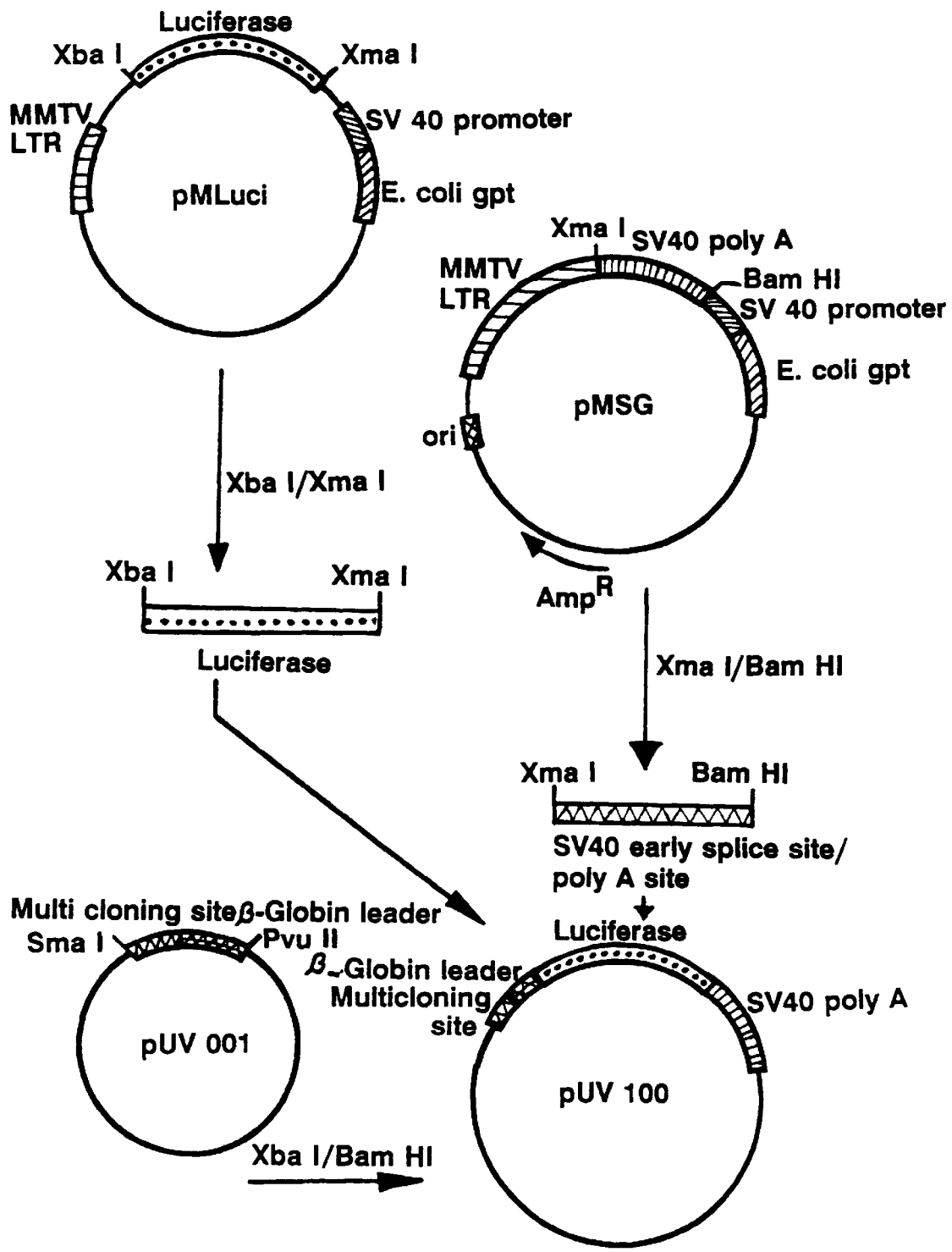
FIG. 12 is a diagrammatic representation of the construction of the plasmid pUV100 from the plasmid pUV001 and two DNA fragments, the XbaI/XmaI fragment from pMLuci and the XmaI/BamHI fragment from pMSG.
Figure 26:
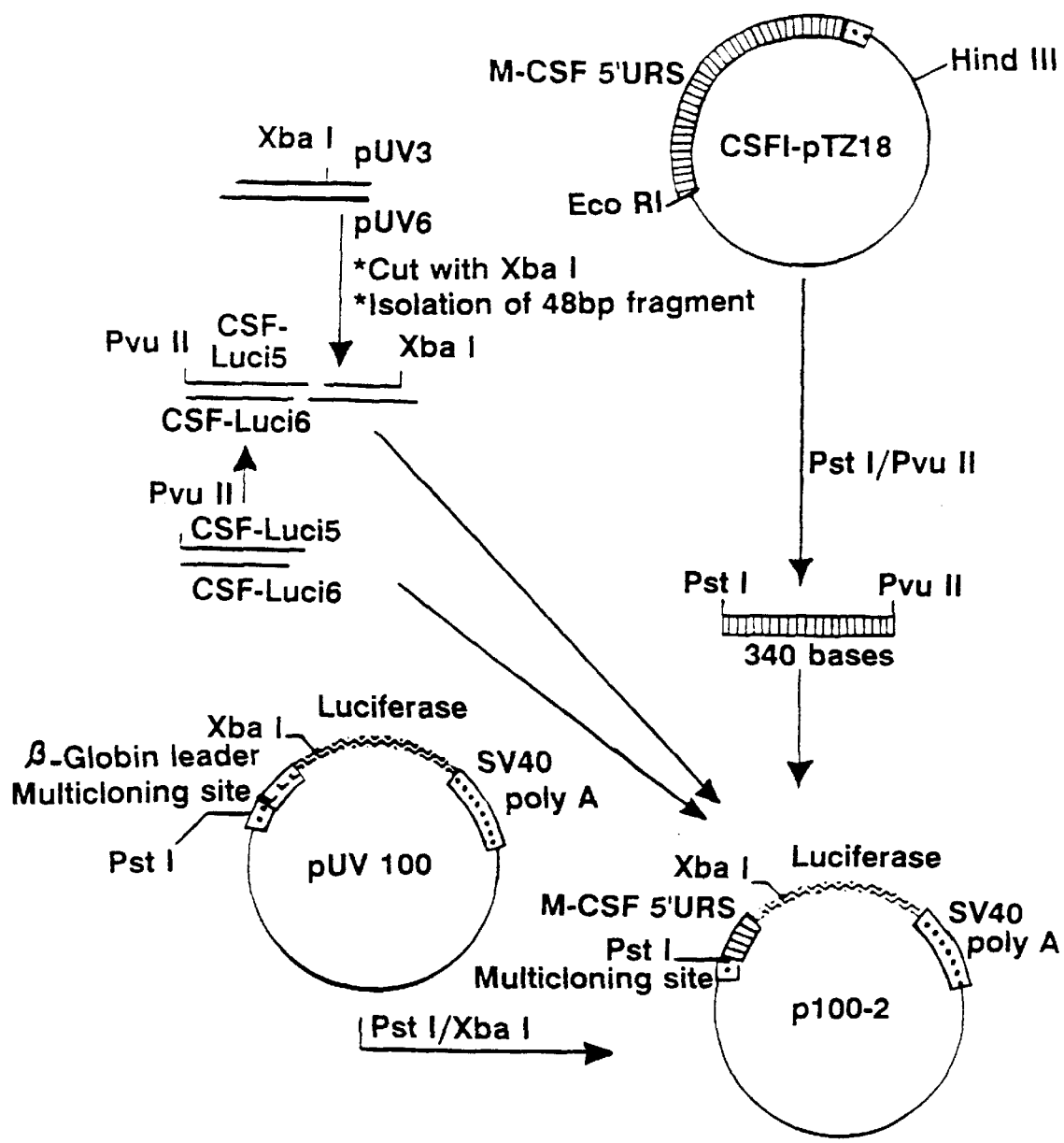
FIG. 26 is a diagrammatic representation of the construction of the plasmid p100-2 by insertion of a PSTI/PVUII fragment from CSFI-pTZ18 and synthetic oligonucleotides into the plasmid pUV100.
Figure 27:
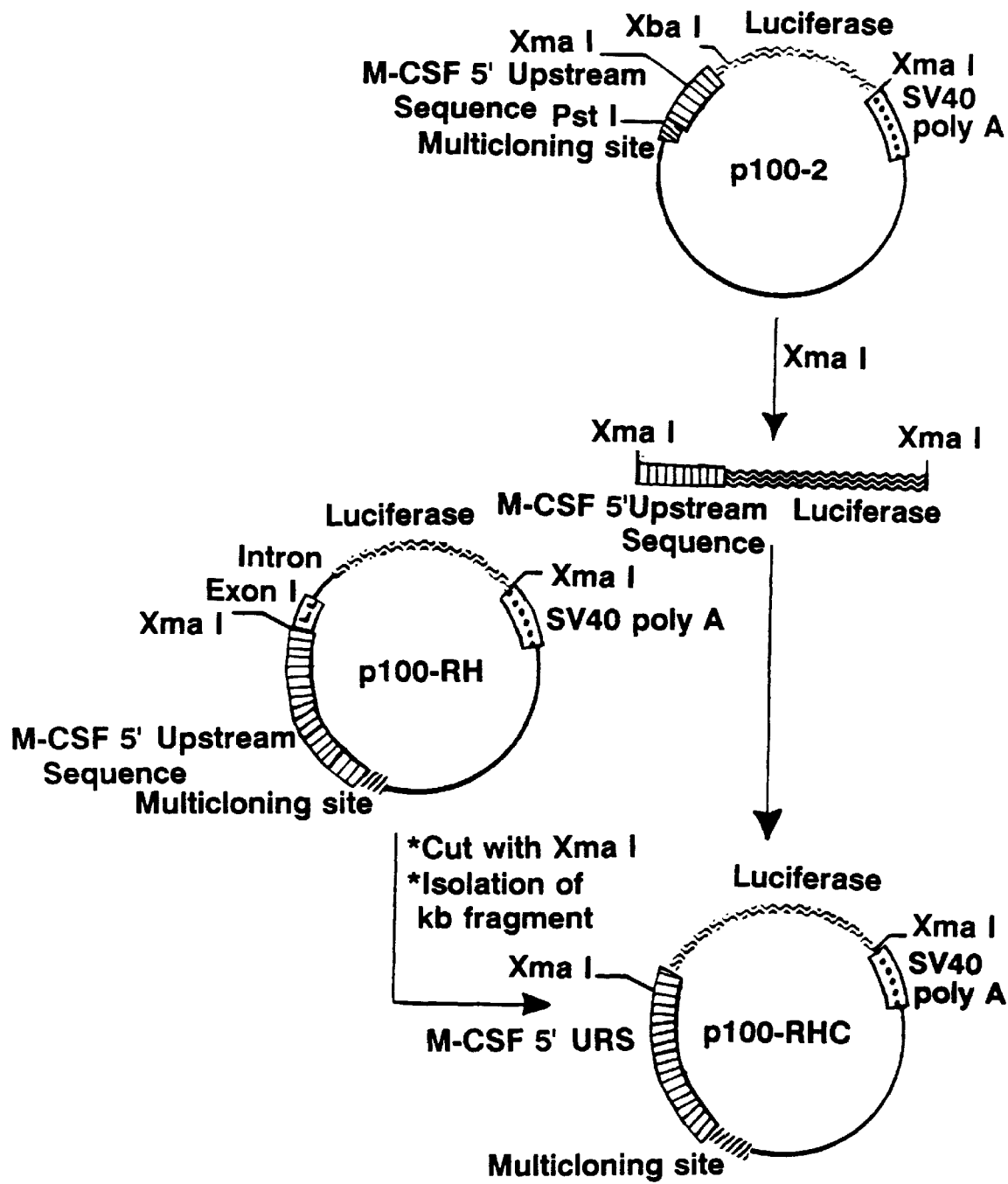
FIG. 27 is a diagrammatic representation of the construction of p100-RHC by insertion of short M-CSF 5' upstream sequences fused to the luciferase coding sequence into the plasmid p100-RH containing a longer M-CSF 5' upstream fragment.
Figure 28:
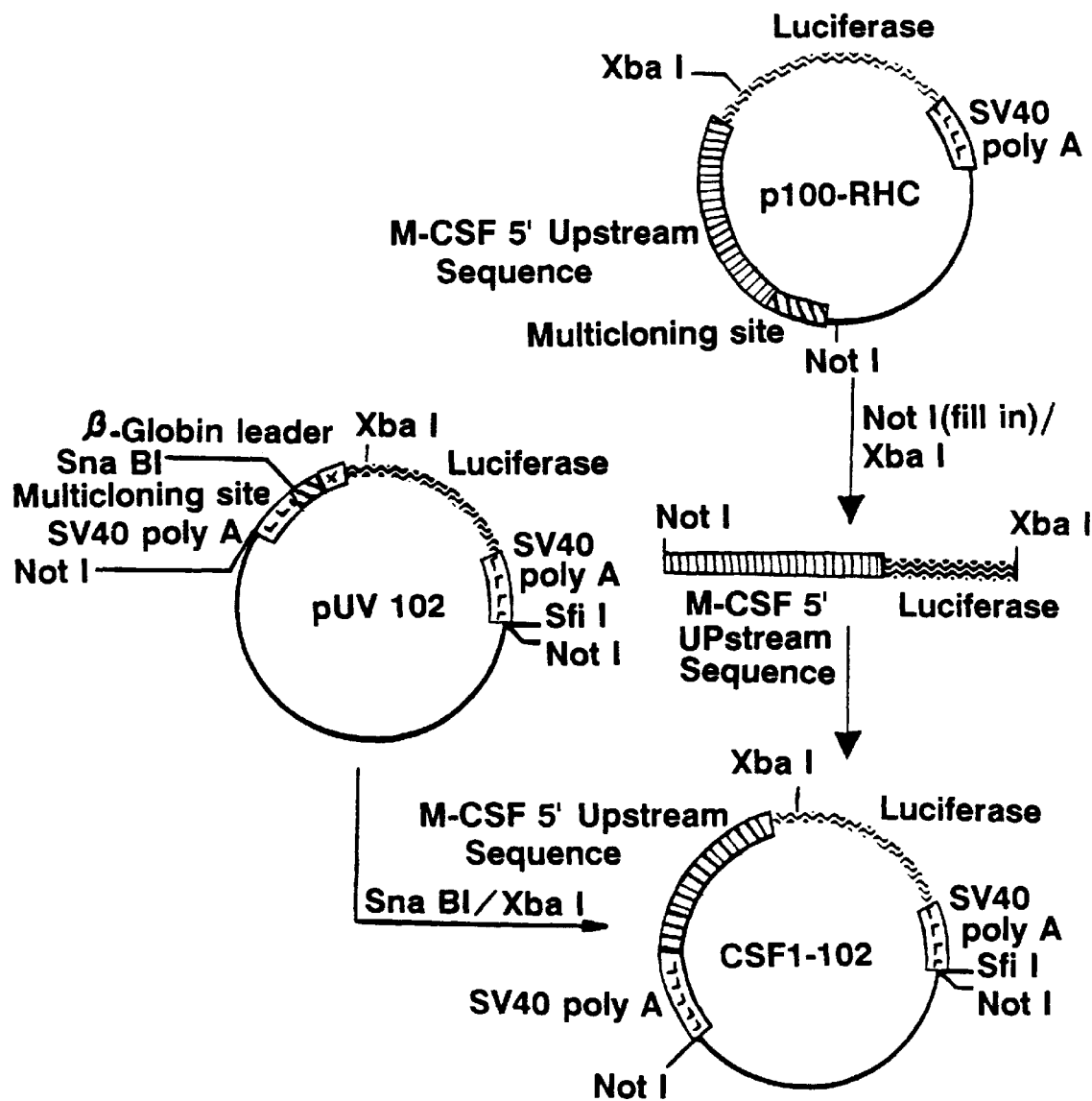
FIG. 28 is a diagrammatic representation of the construction of pCSF1-102 from a 5 kb NotI/Xba I fragment isolated from p100-RHC and inserted into pUV102.

5' ACGGGCAG 3' (CSF-luci6);

(c) oligonucleotides pUV3 and pUV6 (previously used to construct pUV001, FIG. 11(b)) were annealed, and digested with XbaI to release a 48 bp fragment which contains 48 bases of the luciferase coding region; (d) DNA fragments and oligonucleotides (from a, b and c) were ligated and inserted into pUV100 previously digested with PstI/XbaI to yield p100-2 (FIG. 26). A construct containing a larger M-CSF promoter fragment (5 kb) was also made. A 2 kb XmaI fragment was isolated from the plasmid p100-2. This fragment contains the 3' end of the M-CSF leader sequence fused to the luciferase start codon. The 2 kb XmaI fragment was inserted in p100-RH previously digested with XmaI, to yield p100-RHC (FIG. 27). The fused 5 kb M-CSF promoter-luciferase construct was then inserted into pUV102 as follows: a 5 kb NotI/XbaI fragment (blunt ended at the NotI end) was isolated from p100-RHC and inserted into pUV102, previously digested with SnaBI/XbaI, to generate CSF1-102 (FIG. 28). This construct was then used for transfections of 5637 human bladder carcinoma cells.

4. Human Granulocyte Colony Stimulating Factor (G-CSF)

Figure 29:
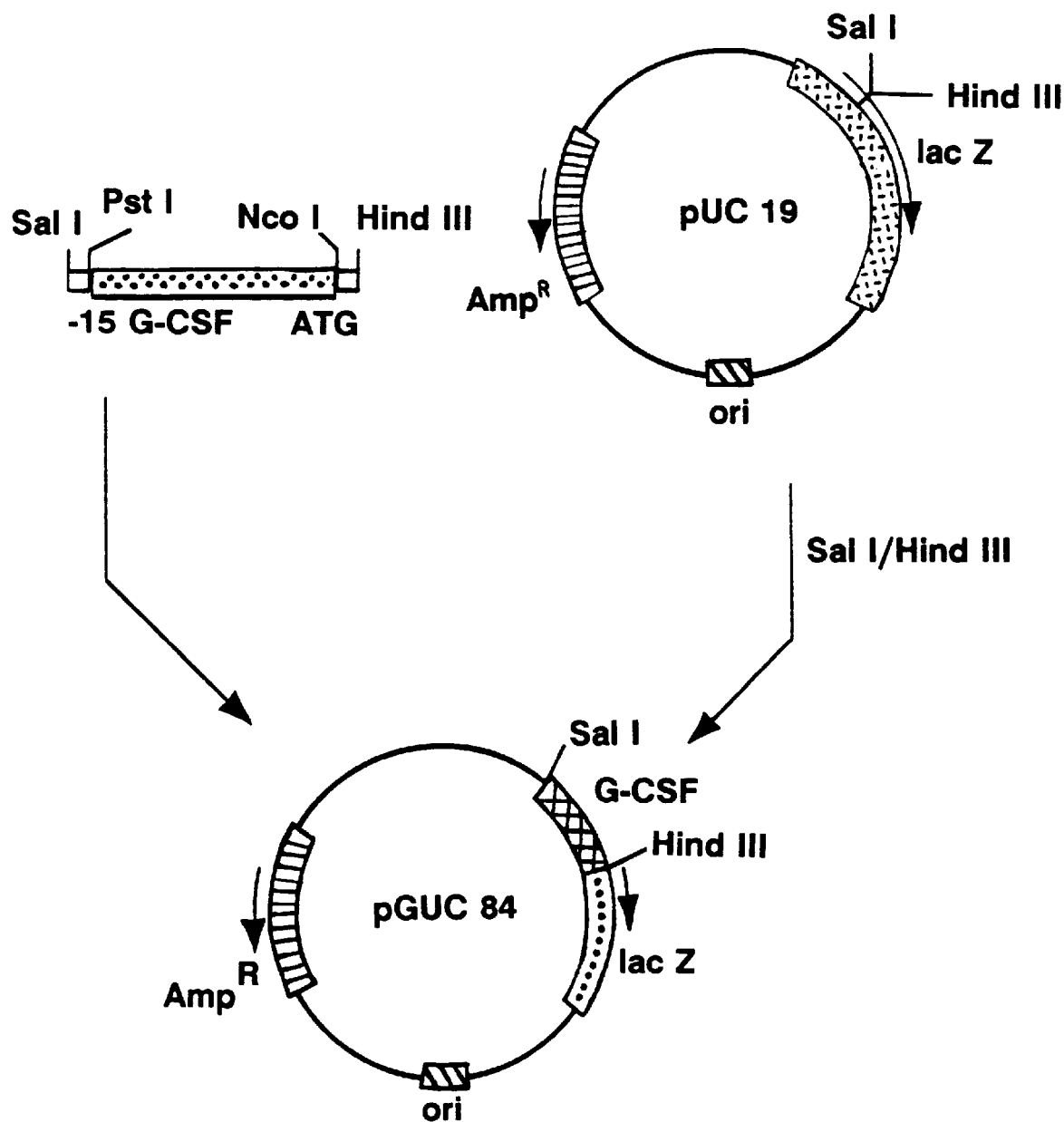
FIG. 29 is a diagrammatic representation of the construction of pGUC84 from oligonucleotides containing the G-CSF leader sequence from +15 to the ATG cloned into the plasmid pUC19.
Figure 30:
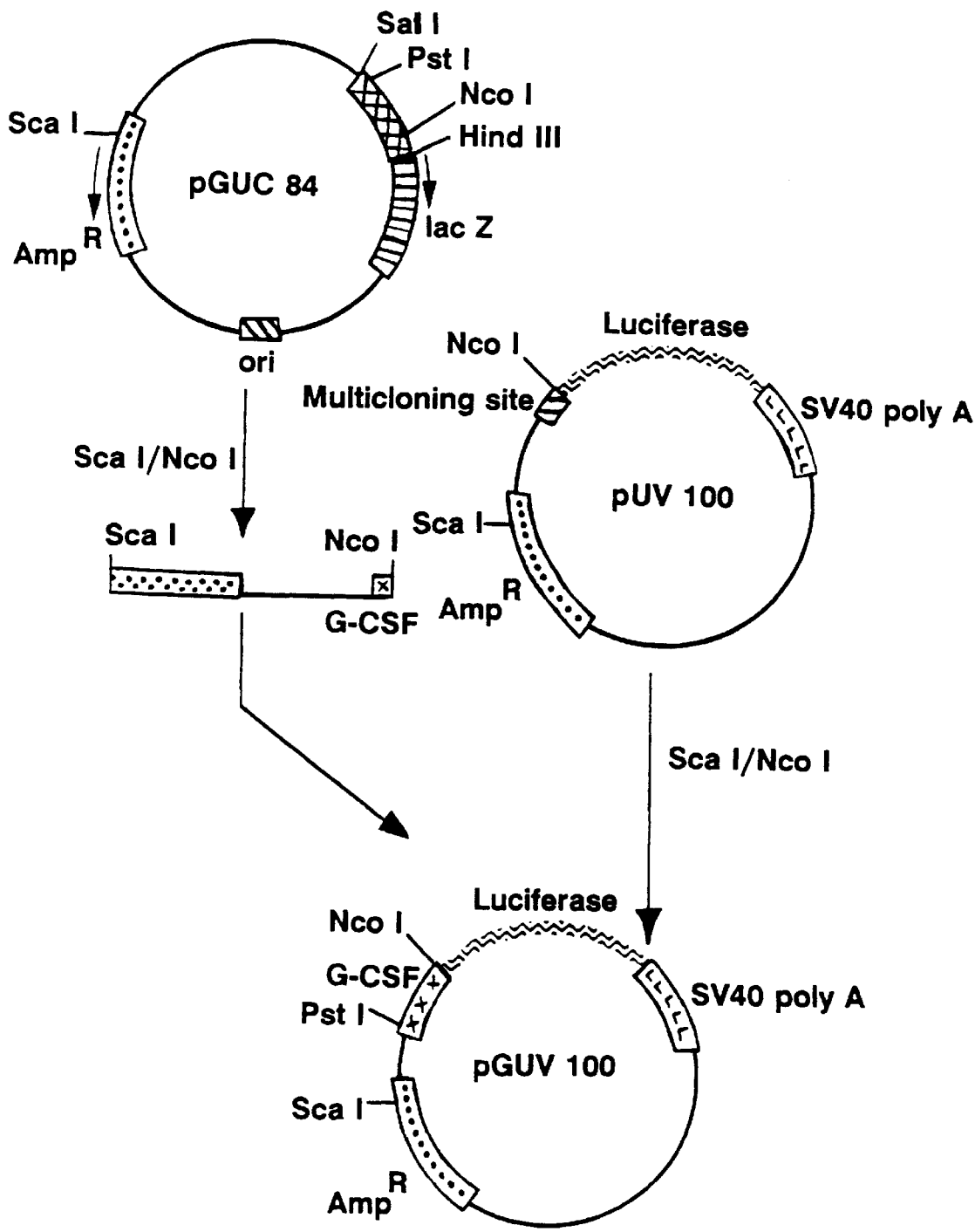
FIG. 30 is a diagrammatic representation of the construction of pGUV100 from the NcoI/ScaI fragment from pGUC84 containing G-CSF leader sequences cloned into the plasmid pUV100.
Figure 31:
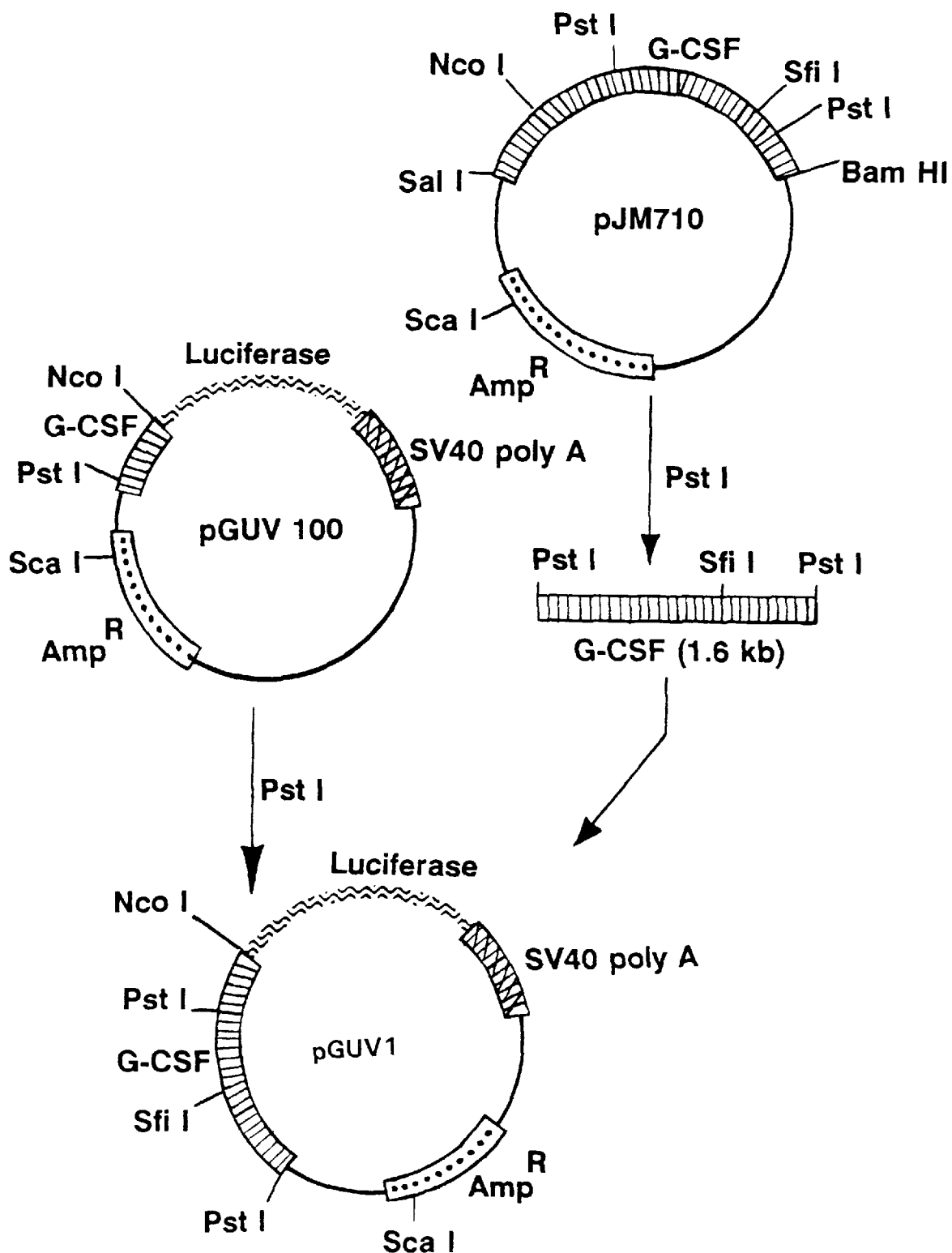
FIG. 31 is a diagrammatic representation of the construction of pGUV1 from the Pst I fragment of the G-CSF promoter from the plasmid pJM710 inserted into the Pst I site in pGUV 100.
Figure 32:
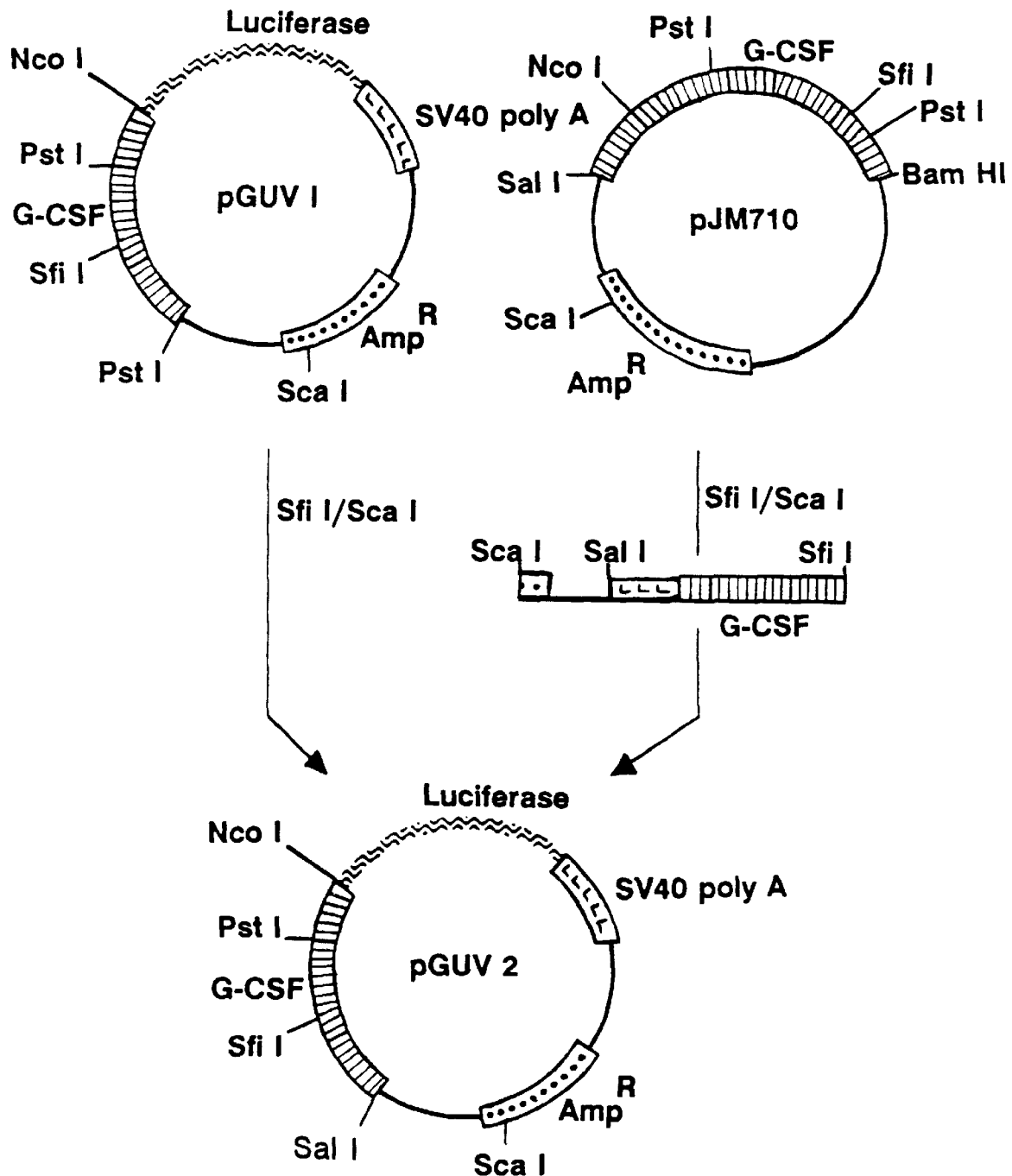
FIG. 32 is a diagrammatic representation of the construction of the plasmid pGUV-2 by insertion of more G-CSF upstream sequences from pJM710 into pGUV1.
Figure 33:
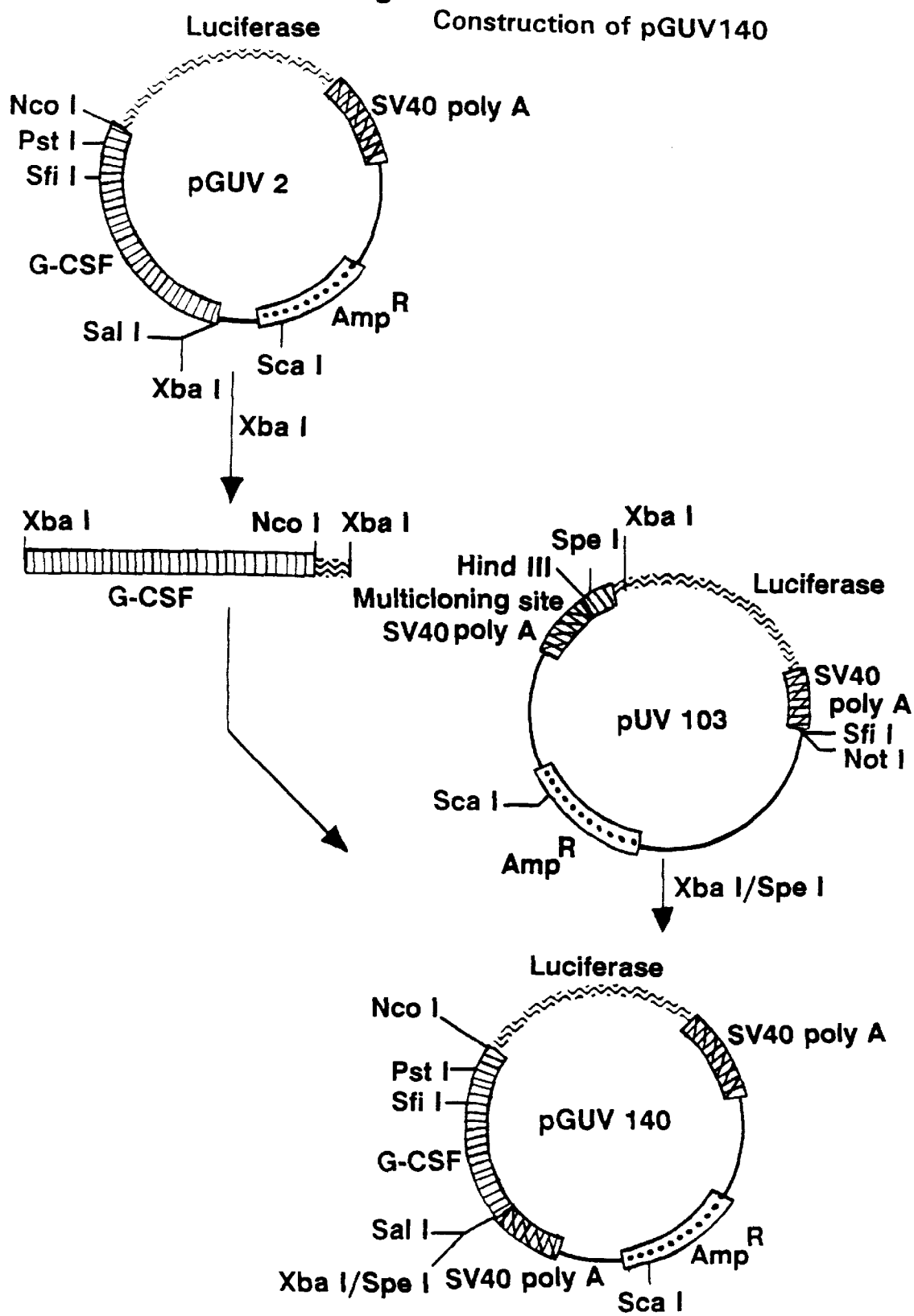
FIG. 33 is a diagrammatic representation of the construction of the plasmid pGUV140 from the XbaI fragment from pGUV2 containing the G-CSF-luciferase fusion and the plasmid pUV103.
Figure 34:
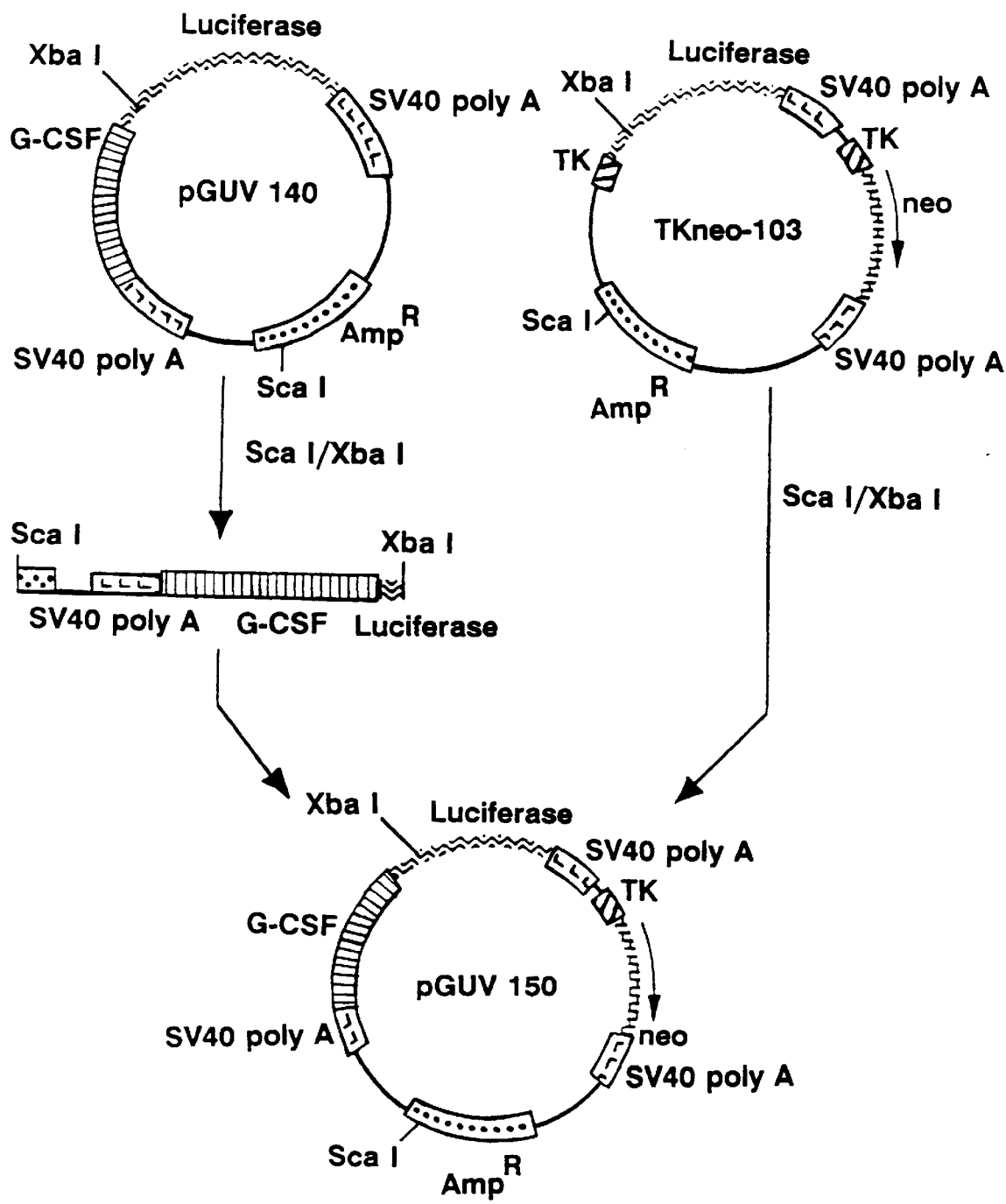
FIG. 34 is a diagrammatic representation of the construction of the plasmid pGUV150 from the ScaI/XbaI fragment from pGUV140 which contains the G-CSF-luciferase fusion and the plasmid pTKNEO-103.

Cloning of G-CSF sequences is described in Experimental Details, section B-3. In order to correctly fuse the G-CSF upstream sequences to the luciferase start codon, oligonucleotides were synthesized which contain the G-CSF leader sequence from +15 to the ATG (32), and were cloned into pUC19 to create pGUC84 (FIG. 29). The sequence of the inserted fragment was determined and was found to be as expected. The G-CSF-oligonucleotide-containing NcoI/ScaI fragment from pGUC84 was then isolated and ligated to the luciferase-containing NcoI/ScaI fragment from pUV100 to create pGUV100 (FIG. 30). Following this, the PstI fragment of the G-CSF promoter was isolated from pJM710 (FIG. 7) and inserted into the PstI site in pGUV100 generating pGUV1 (FIG. 31). The rest of the G-CSF promoter clone was added by ligating the G-CSF-luciferase containing SfiI/ScaI fragment from pGUV1 to the appropriate SfiI/ScaI fragment from pJM710, creating the plasmid pGUV2 (FIG. 32). The XbaI fragment from pGUV2 containing the G-CSF-luciferase fusion was then cloned into pUV103 previously digested with XbaI/SpeI, generating pGUV140 (FIG. 33). Finally, a TK-Neo cassette (Section C) was included by ligating the ScaI/XbaI fragment from pGUV140 which contains the G-CSF-luciferase fusion into pTKNEO103 previously digested with ScaI/XbaI, yielding the final vector pGUV150 (FIG. 34).

5. Erythropoietin (EPO)

Information on the EPO upstream and coding sequences has been published (27) and was used to synthesize two oligonucleotide probes (EP06 and EP08) to screen a human leukocyte genomic DNA library (Clontech, Palo Alto, Calif.) according to the supplier's instructions. The sequences of the oligonucleotide probes were:

5'AATGAGAATATCACTGTCCCAGACAC-
        CAAAGTTAATTTCTATGCCTGGAA 3' (EP08)

5'TTCCAGGCATAGAAATTAAC 3' (EPO6)

Figure 35:
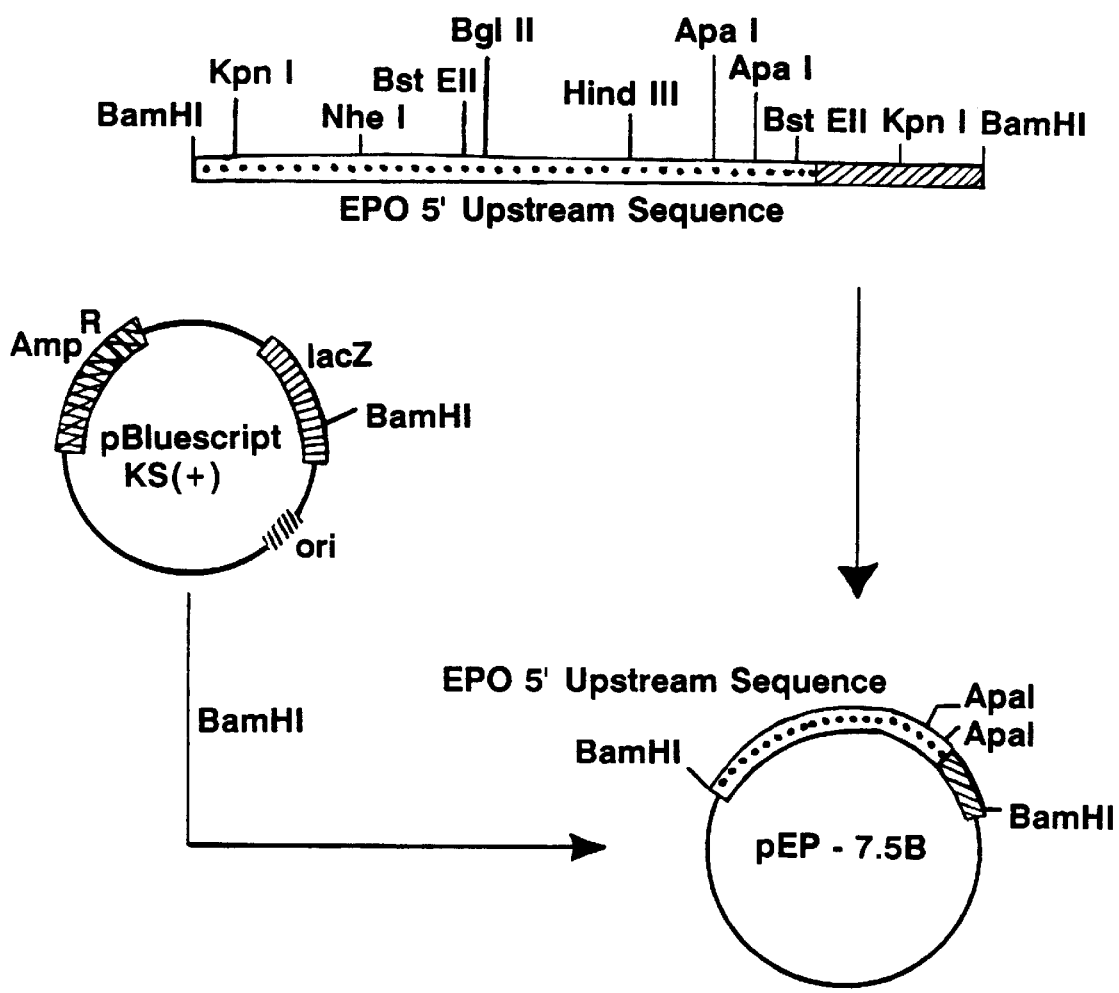
FIG. 35 is a diagrammatic representation of the construction of the plasmid pEP-7.5B from a 7.5 kb BamH1 fragment consisting of 6.2 kb of the EPO promoter region and the first three EPO exons and the plasmid pBluescript KS(+).

EP08 is complementary to sequences within the third exon of the EPO gene (27). EP06 is complementary to the 3' end of EP08 and was used as a primer for filling in the complementary strand of EP08 with labelled nucleotides, thereby generating a probe for cloning. One of the clones isolated from the leukocyte genomic DNA library contained a 7.5 kb BamHI fragment consisting of 6.2 kb of the EPO promoter region and the first three EPO exons. This fragment was inserted into the plasmid Bluescript KS(+) (Stratagene, La Jolla, Calif.), previously digested with BamHI, resulting in the vector pEP-7.5B (FIG. 35). The Epo leader sequence was fused to the start codon of the luciferase gene by using four synthetic oligonucleotides (EP09 to EP012). The sequences of the oligonucleotides were:

5'CCCGGTGTGGTCACCCGGCGCGCCCCAG-
        GTCGCTGAGGGACCCCGGCCAGGCGCGGA 3' (EP09)

5'CATCTCCGCGCCTGGCCGGGGTCCCT-
        CAGCGACCTGGGGCGCGCCGGGTGACCA-
        CACCGGGGGCC 3' (EP010)

5'GATGGAAGACGCCAAAAACATCAA-
        GAAAGGCCCGGCGCCATTCTATCCT 3' (EP011)

5'CTAGAGGATAGAATGGCGCCGGGC-
        CTTTCTTGATGTTTTTGGCGTCTTC 3' (EP012)

Figure 36:
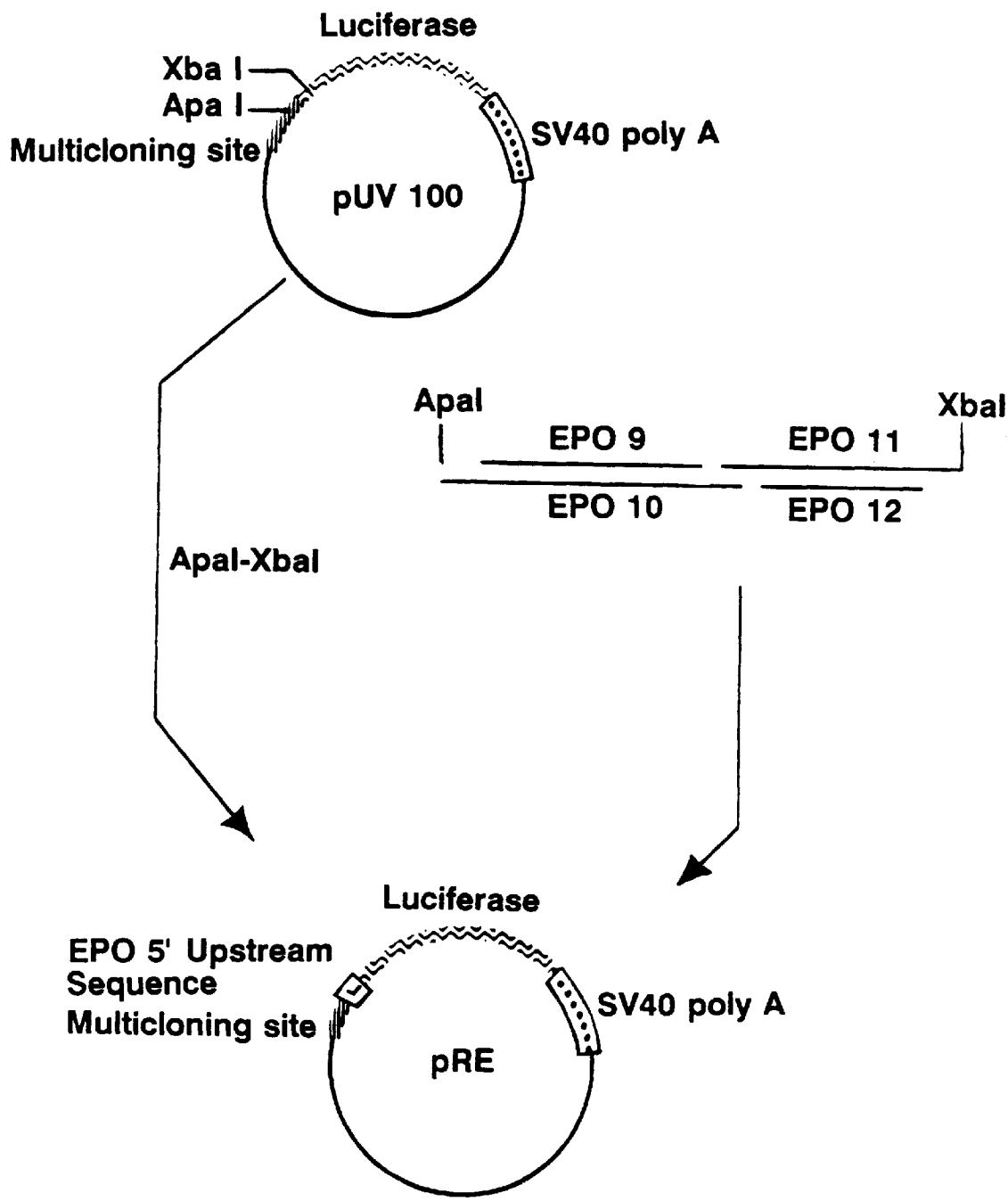
FIG. 36 is a diagrammatic representation of the construction of the plasmid pRE from oligonucleotides EPO 9–12 and the plasmid pUV100.
Figure 37:
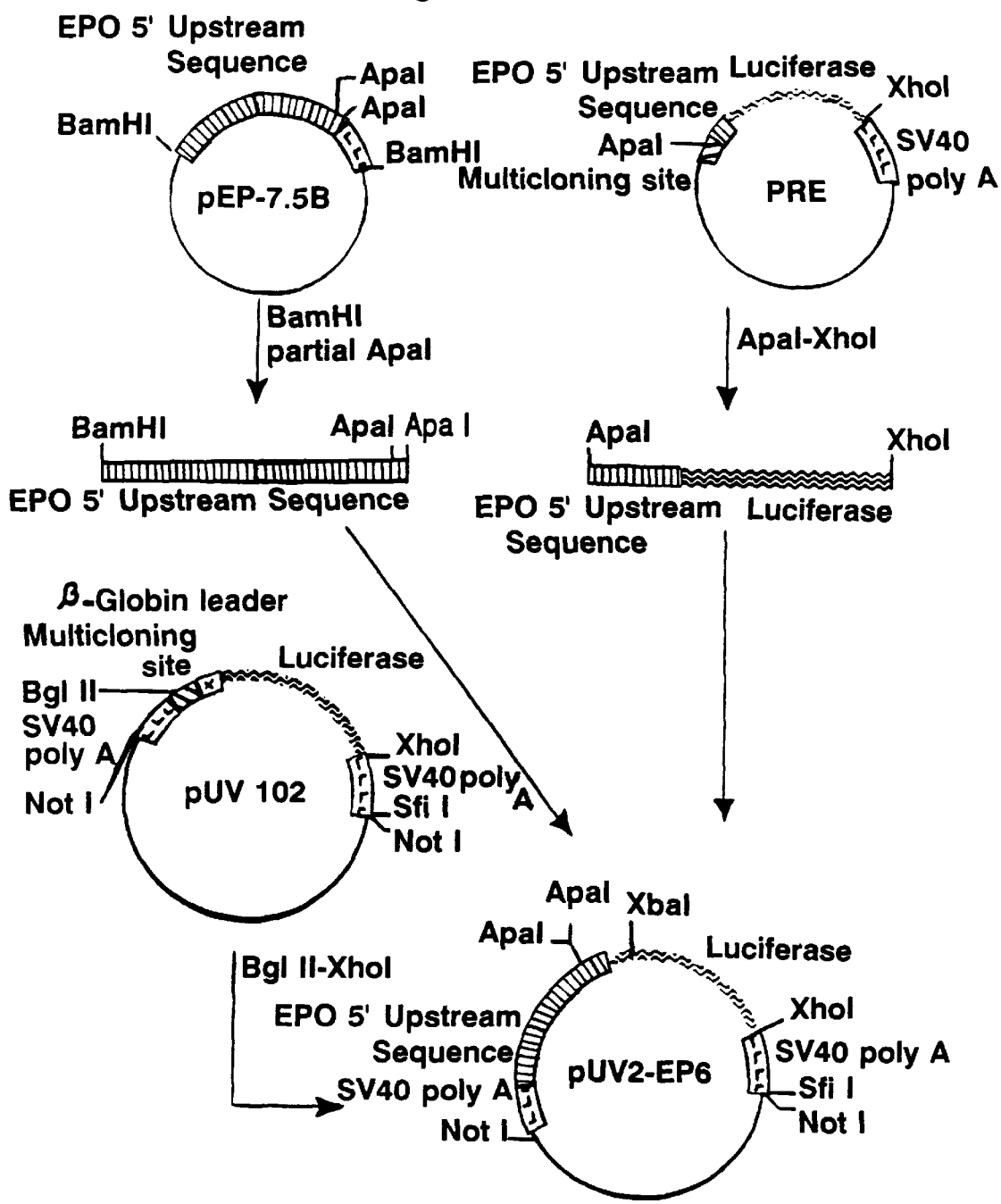
FIG. 37 is a diagrammatic representation of the construction of the plasmid pUV2-EP6 from a 6 kb fragment of EPO upstream sequences and the plasmid pUV 102.

The sequences of EP09 and EP011 consist of 63 bases upstream of the EPO translational start site fused to the first 53 bases of the luciferase coding region. EP010 and EP012 oligonucleotides are complementary to EP09 and EP011, respectively. These oligonucleotides were inserted into the plasmid pUV100 previously digested with ApaI/XbaI to generate the vector pRE (FIG. 36). 6 kb of EPO upstream sequence was cloned into pUV102 by inserting a 6.2 kb BamHI/partial ApaI fragment from pEP-7.5 B and a 1.7 kb ApaI/XhoI fragment from pRE into pUV102 previously digested with BglII/XhoI, yielding pUV2-EP6 (FIG. 37). The 1.8 kb SfiI fragment from pTKNEO3 (FIG. 19) was then inserted into pUV2-EP6 previously digested with SfiI, generating pEP6.0-102-TKNEO.

6. Interleukin-3 or Multi-CSF (IL-3)

Figure 38:
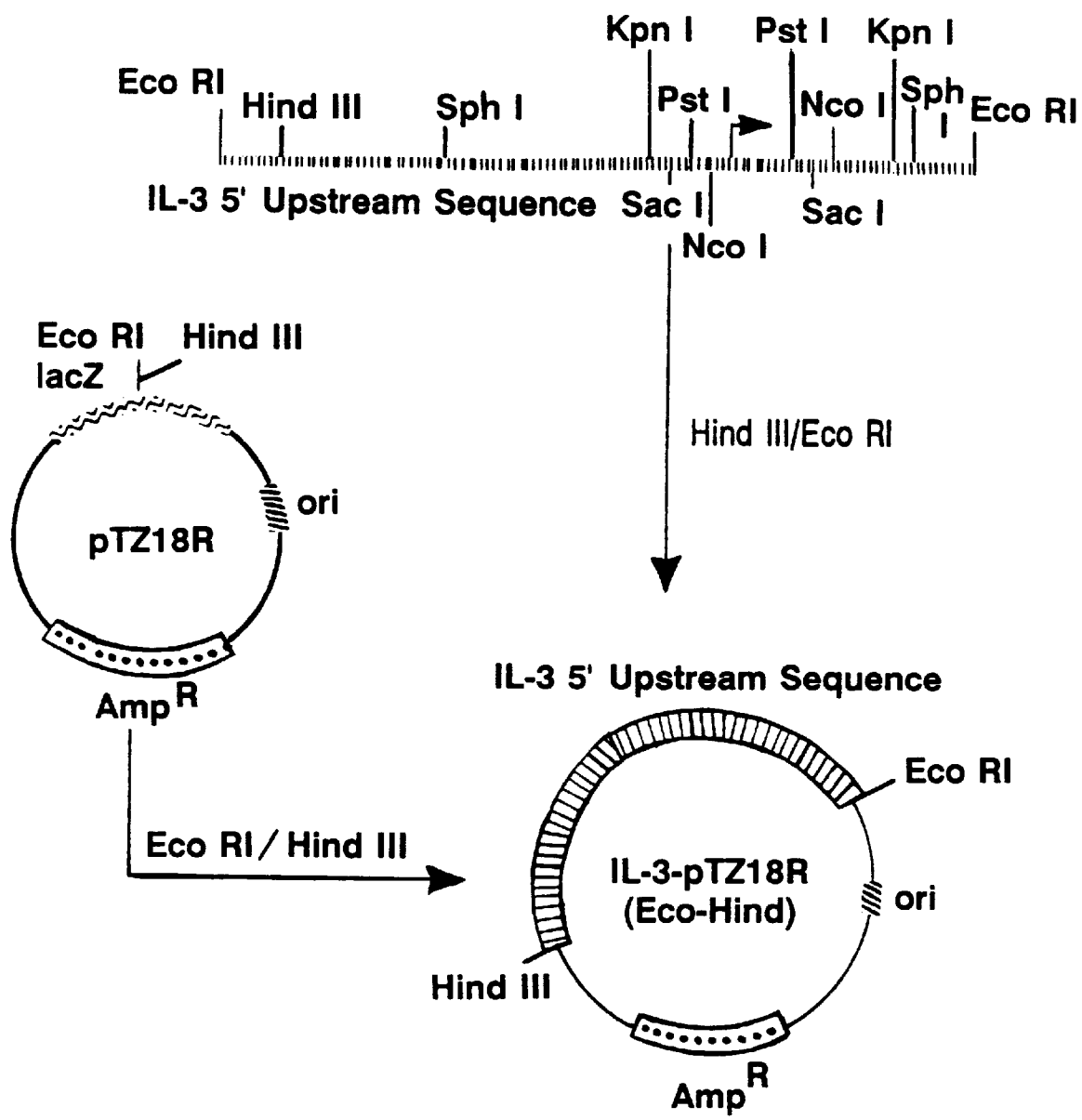
FIG. 38 is a diagrammatic representation of the construction of the plasmid IL-3-pTZ18R from IL-3 upstream sequences and the plasmid pTZ18R.
Figure 39:
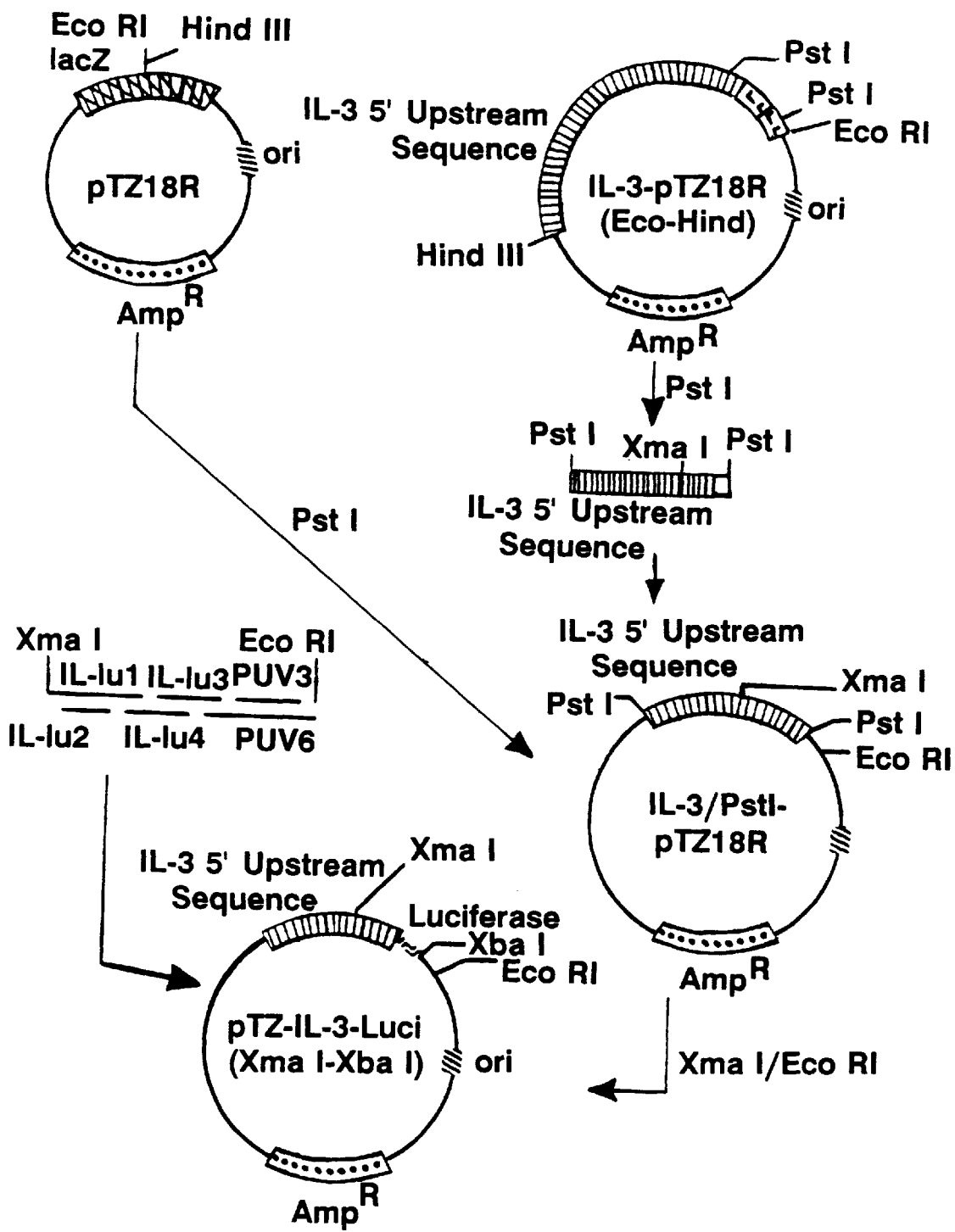
FIG. 39 is a diagrammatic representation of the construction of the plasmid pTZ-IL-3-Luci from oligonucleotides IL-lu-1 to IL-lu-4, pUV-3 and pUV-6 and the plasmid IL3/PstI-pTZ18R.

Information on the IL-3 promoter and coding sequences (40–41) was used to synthesize an oligonucleotide probe (IL-3 II) to screen a human leukocyte genomic DNA library (Clontech, Palo Alto, Calif.) according to the supplier's instructions. The sequence of the oligonucleotide probe was:

5' TAAGTGTGTTATAATTTCATCGATCATGTT 3' (IL-3 II)

which corresponds to sequences within the first exon of IL-3. One of the clones isolated from the leukocyte library using the IL-3 II probe contained an 8 kb HindII/EcoRI fragment of IL-3 sequence consisting of 6.4 kb of upstream sequences and 2 kb of the coding region. This fragment was inserted into the vector pTZ18R (Pharmacia, Piscataway N.J.) previously digested with HindIII/EcoRI, resulting in the vector IL-3-pTZ18R (Eco-Hind) (FIG. 38). The IL-3 leader sequence was fused to the first codon of the luciferase gene as follows. A 900 bp PstI fragment was isolated from IL-3-pTZ18R (Eco-Hind). This fragment contains 700 bp of the IL-3 promoter along with exon 1 of IL-3 (FIG. 39), and was inserted into PTZ18R (Pharmacia, Piscataway, N.J.) previously digested with PstI, resulting in the vector IL3/PstI-pTZ18R (FIG. 39). Four oligonucleotides (IL-lu-1 to IL-lu-4) were synthesized, with the following sequences:

5'CCGGGGTTGTGGGCACCTTGCTGCTGCA-
CATATAAGGCGGGAGGTTGTTGCCAACTCTTC3' (IL-lu-1)

5'AGTTGGCAACAACCTCCCGCCTTATAT-
GTGCAGCAGCAAGGTGCCCACAACC 3'(IL-lu-2)

5'AGAGCCCCACGAAGGACCAGAACAAGA-
CAGAGTGCCTCCTGCCGATCCAAACATGGA 3' (IL-lu-3)

5'GTTTGGATCGGCAGGAGGCACTCTGTCT-
TGTTCTGGTCCTTCGTGGGGCTCTGAAG 3' (IL-lu-4)

Figure 40:
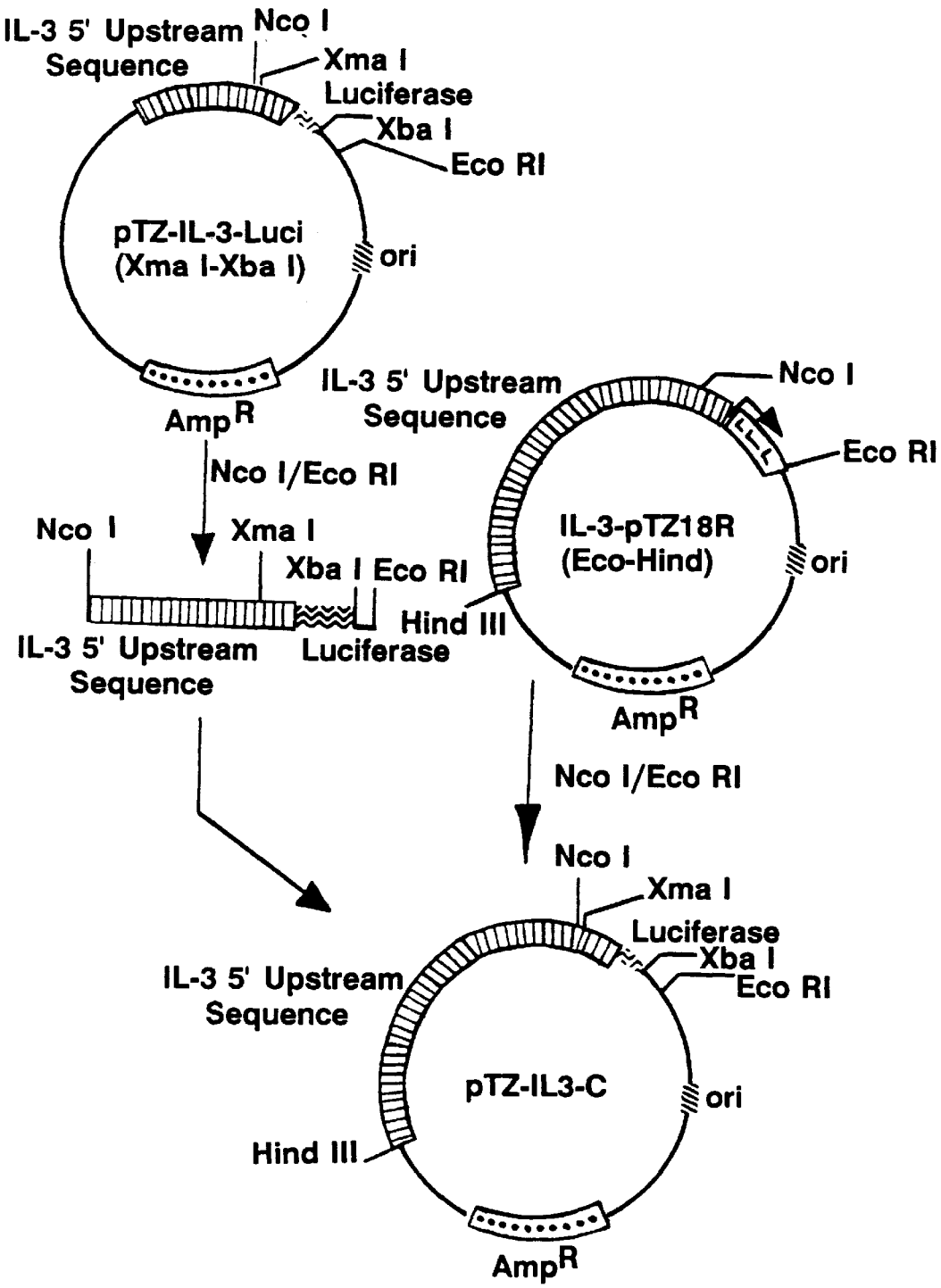
FIG. 40 is a diagrammatic representation of the construction of the plasmid pTZ-IL3-C from a 500 kb NcoI/EcoR1 fragment from pTZ-IL-3-Luci and the plasmid IL-3-pTZ18R.
Figure 41:
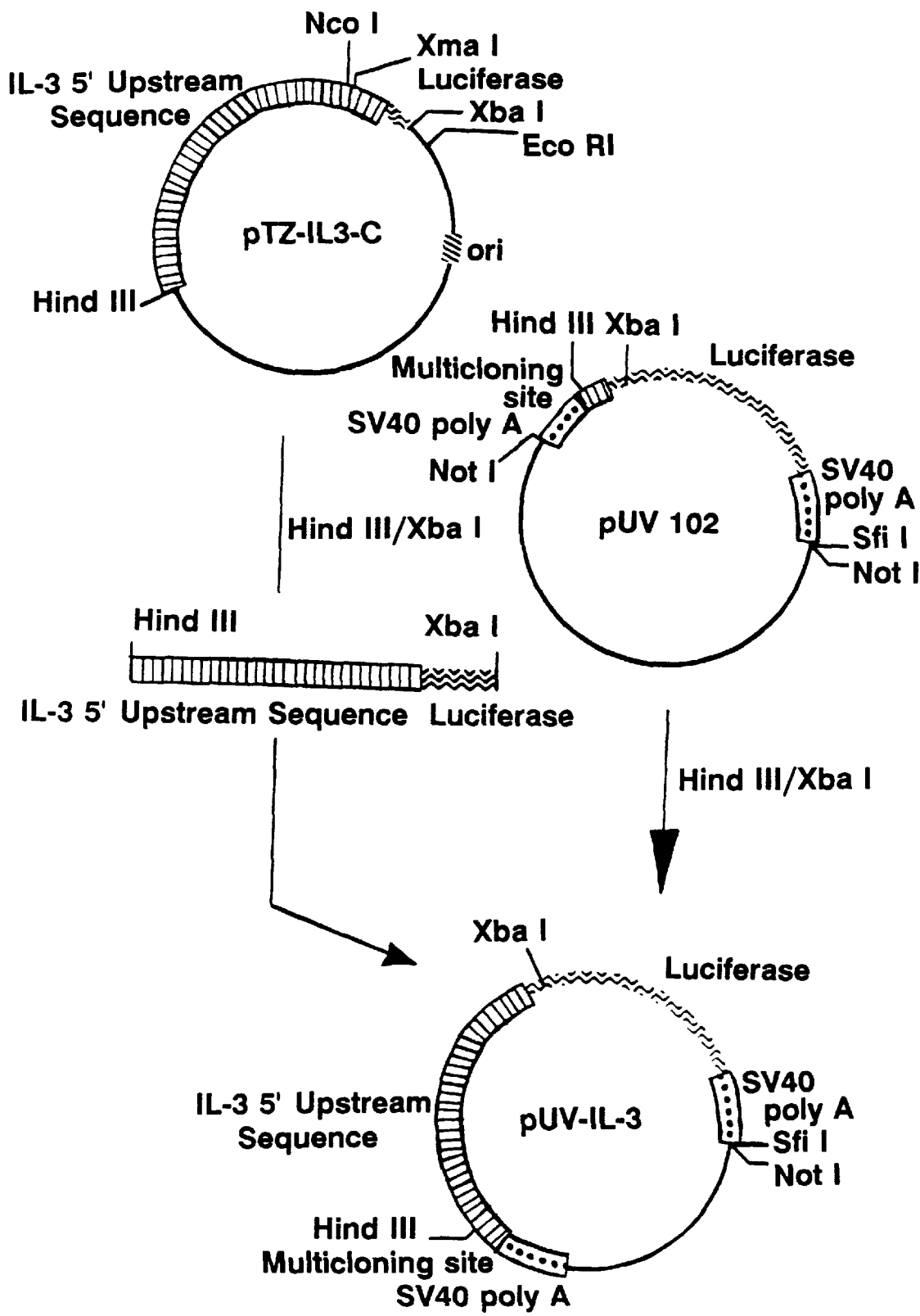
FIG. 41 is a diagrammatic representation of the construction of the plasmid pUV-IL-3 from a 6.4 kb Hind III/XbaI fragment from pTZ-IL3-C and the plasmid pUV102.

The sequences of IL-lu-1 and IL-lu-3 correspond to 112 bases of the 3' end of the IL-3 promoter fused to the first 5 bases of the luciferase coding region. IL-lu-2 and IL-lu-4 oligonucleotides are complementary to IL-lu-I and IL-lu-3, respectively. Oligonucleotides IL-lu-1 to IL-lu-4 along with oligonucleotides pUV-3 and pUV-6 (see Section C) were annealed, ligated and inserted into IL3/PstI-pTZ18R previously digested with XmaI/EcoRI, to generate pTZ-IL-3-Luci (XmaI-XbaI) (FIG. 39). A 6 kb IL-3 promoter fragment was cloned into pUV102 as follows: a 500 kb NcoI/EcoRI fragment was isolated from pTZ-IL-3-Luci (XmaI/XbaI) and inserted into IL-3-pTZ18R (EcoRI/HindIII) previously digested with NcoI/EcoRI to yield pTZ-IL3-C (FIG. 40). A 6.4 kb HindIII/XbaI fragment was then obtained from pTZIL3-C and inserted into pUV102 previously digested with HindIII/XbaI, resulting in the vector pUV-IL-3 (FIG. 41). Finally, the 1.8 kb SfiI fragment from pTKNE03 (FIG. 19) was inserted into pUV-IL-3 previously digested with SfiI, generating the vector pIL3-102-TKNEO.

E. Construction of Single Cell Clones Containing Various Promoter-Luciferase Fusion Constructs 1. pMluci pMluci (FIG. 3) and pSV2Neo, an antibiotic resistance plasmid (34), were co-transfected into NIH/3T3 mouse fibroblast cells using the calcium phosphate precipitation method (15) with a commercially available kit (Pharmacia, Piscataway N.J.). Two days later, cells were transferred to media containing 0.4 mg/ml G418 and were grown for an additional 10–14 days. G418-resistant clones were isolated by standard methods. Once sufficient cell numbers were obtained, clones were analyzed based on several criteria: constitutive luciferase production, induction of luciferase expression by dexamethasone (1 μm, Sigma, St. Louis, Mo.), satisfactory attachment to microtiter plates used in the high-throughput screen (see Section G) and acceptable standard deviation in multiple luciferase expression assays (see below for assay protocol). This analysis was carried out using the luciferase assay conditions described in sections F and G. Of the clones which satisfied the above criteria for the high throughput screen, one clone, M10, was selected for use.

2. phGH-LUCI phGH-LUCI (FIG. 6) and pRSVNeo, an antibiotic resistance plasmid (14), were co-transfected into GC rat pituitary cells as described above. Selection of G418-resistant cell clones was described above except for using a concentration of 0.2 mg/ml G418. Analysis of the cell clones was performed as above, except that known inducers of hGH expression (10–100 nM rat growth hormone releasing factor (rGRF, Bachem, Torrance, Calif.) and 10 μm forskolin (Sigma, St. Louis, Mo.) were used in place of dexamethasone. One clone, 532, was selected for further use in the high throuhgput screen.

3. pG-LUC1 pG-LUC1 (FIG. 9) and pRSVNeo were co-transfected into 5637 human bladder carcinoma cells as described above. Selection of G418 resistant clones was as described above except for using a concentration of 0.1 mg/ml G418. Analysis of cell clones was performed as above except that a known inducer of G-CSF expression (1–5 lg/ml lipopolysaccharide (LPS), E. coli serotype 055:b5, Difco, Detroit, Mich. or Sigma, St. Louis, Mo.) was used in place of dexamethasone. One clone, G21, was selected for use.

4. pGVU150 and pGVU140/pTKNEO3

All the following constructs were transfected into 5637 bladder carcinoma cells either by electroporation using a BRL (Gaithersburg, Md.) Cellporator electroporation device or by lipofection using BRL lipofectin and following the manufacturer's protocol. For electroporation, cells were trypsinized, treated with Soybean trypsin inhibitor (1 mg/ml), washed three times in Dulbecco's modified Eagle's medium (DMEM) without pH indicator, and 1 ml of cell suspension in DMEM was electroporated at room temperature and at a cell density of 5 million cells per ml at a voltage of 250 V and a capacitance of 1180 microFarad with the electroporation device set at low resistance. In previous experiments these parameters had been determined to result in optimal electroporation efficiency. About 15 min after electroporation cells were recovered from the disposable electroporation containers (BRL, Gaithersburg, Md.) and plated in RPMI containing 10% fetal calf serum. 2 days after electroporation 0.4 mg/ml G 418 were added and clonal cell colonies were picked 14–20 days after transfection. Clones were first analysed for luciferase expression using Lysis Buffer 1 without bovine serum albumin (see Section F) and those testing positive expanded further and frozen in liquid nitrogen. Further analysis of 6 clones (G 1002, G 2005, G 2071, G 2085, G 3014, G3031) included Southern blotting, reaction to known inducers, satisfactory attachment to microtiter plates and acceptable standard deviation in multiple luciferase expression assays. Clones G 2005 and G 2085 were derived from 5637 cells lipofected with 100 ug/ml of linearized pGVU150 (FIG. 34), G 3031 descends from cells electroporated with 100 ug/ml of linearized pGVU150, whereas 200 ug/ml of the same plasmid were used to generate G 3014. Cotransfection of circular pGVU140 (FIG. 33) with circular pTKNeo3 (FIG. 19) was used to generate clones G 1002 and G 2071. While G 1002 resulted from co-electroporation of 50 and 5 ug/ml of the two plasmids, G 2071 descends from cells lipofected with 100 and 10 ug.

5. pCSF1-102/pTKNeo3

3 clones generated by co-electroporation with linearized pCSF1-102 (FIG. 28) and linearized pTKNeo3 (FIG. 19) were subjected to further analysis as outlined above: M 2071 (6 ug pCSF1-102; 0.5 ug pTKNeo3), M 2085 and M 2086 (both: 10 ug pCSF1-102 and 1 ug pTKNeo3).

6. pGMLL103 NEO3

6 clones generated by electroporation with pGMLL103 NEO3 (FIG. 23; Materials and Methods, section D.2) were subjected to further analysis as described above: GM 1073 (10 ug; circular); GM 1081, 1088 and 1090 (5 ug; linear); and GM 1098 and 1105 (10 ug; linear).

F. Liquid Scintillation Counter Bioluminescence Assay

To assay for luciferase expression in transient expression assays in the various transfected clones, cells were incubated with various transcriptional inducers in serum free defined media, washed 5 times with Dulbecco's phosphate-buffered saline (D-PBS, Gibco) and lysed in Lysis Buffer 1 (50 mM Tris acetate pH7.9, 1 mM EGTA, 10 mM magnesium acetate, 1 mg/ml bovine serum albumin [BSA], 0.5% Brij 58, 2 mM ATP, 100 mM dithiothreitol [DTT]). All reagents were obtained from Sigma except for DTT which was from Boehringer Mannheim. After lysis, cell debris was sedimented by brief centrifugation, and 950 ll of supernatant extract were added to a glass scintillation vial. Samples were counted individually in an LKB (Gaithersburg, Md.) scintillation counter on a setting which allows measurement of individual photons by switching off the coincidence circuit. The reaction was started by addition of 50 ll of 2 mM luciferin (Sigma, St. Louis, Mo. or Boehringer Mannheim, Indianapolis Ind.) in Buffer B (Buffer B-Lysis Buffer 1 without Brij 58, ATP and DTT) to the 950 ll of lysate. Measurement was started 20 seconds after luciferin addition and continued for 1 minute. Results were normalized to protein concentration using the Bradford protein assay (BioRad, Richmond Calif.) or to cell numbers using Trypan Blue (Sigma) exclusion counting in a hemocytometer (see section G).

G. High-Throughput (HTP) Screening

Cell plating: Dynatech Microlite 96 well plates were custom pretreated for cell attachment by Dynatech Laboratories, Inc. (Chantilly, Va.). Alternatively, the 96 well plates were treated with 50 ll per well of human fibronectin (hFN, 15 lg/ml in PBS, Collaborative Research, Bedford, Mass.) overnight at 37° C. hFN-treated plates were washed with PBS using an Ultrawash 2 Microplate Washer (Dynatech Labs), to remove excess hFN prior to cell plating. M10, 532, and M21 cells maintained in their respective serum media (with 0.2 mg/ml G418) were washed with PBS, harvested by trypsinization, and counted using a hemocytometer and the Trypan Blue exclusion method according to protocols provided by Sigma, St. Louis, Mo. Chemical Company. Cells were then diluted into serum free defined media (with 0.2 mg/ml G418), and 0.2 ml of cell suspension per well was plated onto Dynatech treated plates (532 and G21) or hFN-treated plates (M10) using a Cetus Pro/Pette (Cetus, Emeryville, Calif.). Plates were incubated overnight at 37° C. in a humidified 5% $CO_2$ atmosphere.

Addition of Chemicals to Cells: Chemicals from the Oncogene Science file were dissolved in DMSO at concentrations of 3–30 mg/ml. A liquid handling laboratory work station (RSP 5052, Tecan U.S. Chapel Hill, N.C.) was used to dilute the chemicals (three dilutions; 5 fold, 110 fold, and 726 fold). 10 ll of each dilution were added to each of quadruplicate samples of cells contained in the wells of 96-well Dynatech Microlite Plates. Cell plates were then shaken on a microplate shaker (Dynatech, medium setting, 30 sec.) and incubated for 6 hours at 37° C, 5% $CO_2$.

Bioluminescence Assay: After incubation with OSI-file chemicals, cell plates were washed 3 times with PBS using an Ultrawash 2 Microplate Washer (Dynatech Labs) and 75 ll of Lysis Buffer 2 were added to each well (Lysis Buffer 2 is the same as Lysis buffer 1 except that the ATP and DTT concentrations were changed to 2.67 mM and 133 mM, respectively). Bioluminescence was initiated by the addition of 25 ll 0.4 $\mu$m Luciferin in Buffer B to each well, and was measured in a Dynatech ML 1000 luminometer following a 1 minute incubation at room temperature. Data were captured using Lotus-Measure (Lotus) software and processed by custom-designed macros written in Lotus.

More recently the cell lysis buffer was modified to also contain the luciferin. Therefore, lysis of cells and the bioluminescence reaction begin simultaneously and the production of bioluminescent light reaches a maximum at about 5 min. The level of light output declines by about 20% within further 30 min. For better lysis buffer stability bovine serum albumin has been omitted. This improved lysis buffer has been shown to remain fully functional for at least 12 hours, when kept on ice and protected from direct light.

Also, more recently, a fully automated device as described in U.S. patent application Ser. No. 382,483 was used to incubate luciferase reporter cells in 96-well microtiter plates, transfer chemicals and known transcriptional modulators to the cells, incubate cells with the chemicals, remove the chemicals by washing with PBS, add lysis buffer to the cells and measure the bioluminescence produced.

H. Isolation of Total Cellular RNA

Total cellular RNA was isolated from the G21 cell clone or from untransfected 5637 cells following incubation for 6 hours with various transcriptionally modulating chemicals identified in the high-throughput screen. Cells were grown in serum free medium as described above. Total cellular RNA was isolated using the RNAZol method (CINNA/ BIOTECX, Friendswood, Tex. Laboratories International, Inc.). Cells were resuspended and lysed with RNAZol solution (1.5 ml/9 cm petri dish) and the RNA was solubilized by passing the lysate a few times through a pipette. Chloroform was added to the homogenate (0.1 ml/1 ml), and samples were shaken for 15 seconds followed by a 5 minute incubation on ice. After centrifuging for 10 minutes, the upper phase was collected and an equal volume of isopropanol was added. Samples were incubated for 45 minutes at −20° C., and the RNA was pelleted for 15 minutes at 12,000×g at 4° C. The RNA pellet was then washed with 70% ethanol and dried briefly under vacuum.

I. Northern Blotting

Total cellular RNA was isolated from 5637 cells following incubation with chemicals as described above and electrophoresed in a 1% Agarose-$\mu$m Formaldehyde gel. The RNA was transferred to Duralon-UV nylon filters (Stratagene, La Jolla, Calif.) using the manufacturer's recommended protocol. The filters were prehybridized for 4 hours (prehybridizing solution=5X SSC, 50 mM sodium pyrophosphate, 10X Denhardt's solution, 10% dextran sulfate, 7% SDS and 250 lg/ml denatured ssDNA) and then hybridized in the same solution for 16 hours at 65 C. in the presence of G-CSF or Beta-Actin (Oncor, Gaithersburg, Md.) specific probes. The G-CSF probe was a 0.6 kb AflII to XhoI fragment which contained most of exon 5 of the human G-CSF gene. The B-actin probe was used as a control probe to normalize for the total amount of RNA. The probes were labeled with alpha-$^{32}$P dCTP using a random primed DNA labeling kit (Amersham, Arlington, Ill.). Following hybridization, filters were first probed with, G-CSF-and Fusion reprobed with B-Actin Probe were washed three times at room temperature with 1X SSC, 0.13% SDS and three times at 65° C. with 0.2X SSC, 0.1% SDS. Filters were first probed with G-CSF-and then reprobed with B-actin-probe. Exposure to x-ray fiμms was performed overnight. Bands were excised and counted in a liquid scintillation counter (LKB, Gaithersburg, Md.), and counts obtained with the G-CSF specific probe were normalized relative to the counts obtained with the B-Actin specific probe.

J. S1 Nuclease Protection

S1 Nuclease protection assays were carried out as described in reference 94.

K. Southern Blotting

To monitor correct and complete stable integration of transfected promoter/reporter constructs, stably transfected cell clones were subjected to Southern blot analysis (92). Genomic DNA was prepared of each clone to be tested and restriction-cut with Dra I. After electrophoresis, transfer to nylon filters and immobilization by UV irradiation using a Stratalinker UV device (Stratagene, La Jolla, Calif.), integrated promoter/luciferase fusion constructs were visualized by probing with radioactively labelled XbaI-EcoRI fragments of the luciferase coding region. Probes were labelled using the random primer method (93). Since Dra I cuts in the SV 40 polyadenylation sites located in the OSI mammalian expression shuttle vector just upstream the inserted promoter sequences as well as downstream of the luciferase coding region, but not in any of the 3 promoter sequences used for generating stably transfected cell clones, a single fragment should be visualized by the probe used. The size of that fragment should be characteristic for each of the three promoter sequences analyzed.

L. MTT Cell Toxicity Assay

To determine cytotoxic concentrations of chemicals registering as positives in the High-Throughput luciferase assay the MTT cytotoxicity assay was employed (95). In this assay, a tetrazolium salt [3-(4,5-dimethylthiazol-2-yl)-2,5-diphenyl-tetrazolium bromide, MTT] is reduced to a colored formazan product by reducing enzymes present only in living metabolically active cells.

M. Two-antibody Sandwich Immunoassay

Supernatants from 5637 bladder carcinoma cells incubated with chemicals registering as positives in the G-CSF promoter/luciferase High-Throughput assay were assayed for secreted G-CSF protein using the two-antibody sandwich immunoassay (96). The G-CSF Assay kit manufactured by Oncogene Science, Inc. was used and the manufacturer's instructions were followed.

N. Construction of a Yeast Expression Vector

Plasmid pHZ18 (97,98) contains $2\mu$ DNA for propagation in S. cerevisiae, the yeast promoter cyc 1, which is compatible with expression in yeast cells, and the URA 3 gene for selection. The plasmid was linearized with BamHl, the ends were filled-in using deoxynucleotides and E. coli DNA polymerase Klenow fragment, and then the plasmid was digested with Aat II. A 4.1 kb fragment containing the cycl promoter, URA3 and $2\mu$ genes was separated by agarose gel electrophoresis and subsequently purified by electroelution onto ion-exchange paper (Whatman, DE81). Plasmid pBR322 was treated with endonuclease Aat II and Pvu II and a 2.2 kb fragment containing the plasmid's origin of replication and the $amp^R$ gene was isolated by agarose gel elecrtrophoresis and eluted onto DE81 paper.

The 2.2 kb pBR322 and 4.1 kb pHZ18 fragments were ligated using T4 DNA ligase according to standard procedures (94). The resulting 6.3 kb vector pHZBR was digested with BamHl for subsequent insertion of the luciferase coding sequence downstream of the cycl promoter.

An Nco I-Sal I fragment of pUV102 containing the luciferase gene starting at the second ATG, was made blunt-ended by filling in and ligated into the filled-in BamHl site of pHZBR. Clones of the correct orientation were identified via restriction mapping to yield plasmid pHZluci24. This plasmid was used to transform S. cerevisiae strain DB745.

O. Transformation of Yeast Cells

S. cerevisiae DB745 were made competent according to published methods (99). One and 4 μg of either pHZluci24 or pHZ18 (transfection control) were added to the competent cells and incubated at 30° C. for 30 minutes. Lithium acetate-PEG was mixed gently with the cells and allowed to incubate for another 45 minutes at which time the cells were shifted to 42° C. for 5 minutes. The cells were spread onto uracil(-) plates and incubated at 30° C. for several days. Cell colonies were picked, grown to saturation in YPD media and analyzed for luciferase activity. Stock cultures were made from positive clones, and each was subsequently analyzed for suitability for the 96-well plate high-throughput assay.

P. Luciferase Bioluminescence Assay in Microtiter Plates

Expression of the firefly luciferase gene was determined by measuring luminescence in the presence of substrates essentially as described above.

Formatting the assay to a 96-well plate required optimization of cell lysis conditions, substrate concentrations and the reaction measurement time. Initial experiments were conducted using purified luciferase and substrates. Bioluminescence was measured either by scintillation counting or in a Dynatech ML1000 luminometer and the reaction conditions were optimized to provide the highest signal-to-noise ratio. Cell lysis conditions were optimized to result in complete lysis of the cells yet not interfere with the luciferase reaction. The detergent Brij 58 fulfilled these requirements. In the current format the 96-well assay was carried out as follows:

$1-2 \times 10^4$ yeast cells were seeded into 96-well plates which have been custome designed to allow filtration of the media while retaining the cells, and which are opaque to permit analysis using a luminometer (Millipore).

After the media was removed from the cells by suction, 100 μl of lysis buffer (50 mM Tris/acetate pH 7.9, 1 mM EGTA, 10 mM Mg-acetate, 0.5% Brij 58, 100 mM DTT and 4 mM ATP, 0.2 mM Luciferin, 800 U/ml lyticase) was added and the plates were incubated at room temperature for 10 minutes. Bioluminescence was monitored in a Dynatech ML1000 luminometer.

RESULTS

A. Validation of Luciferase Reporter Technology

Linearity of the Luciferase Reporter System

Various amounts of luciferase (0, 20, 40, 80, 160, 320, 640, 1280 femtograms; 20 femtograms correspond to 200,000 molecules) in Lysis buffer 1 were added to 24 96-well microtiter plates (0 and 1280 femtograms 576 replicate wells, all other concentrations 192 replicate wells). Bioluminescence reactions were started and light output measured as described in Materials and Methods, Section G. The 24 replicate plates were processed in a random order determined by a random number generator. Mean bioluminecent signals and standard deviations obtained from 576 or 192 replicate measurements (see above) were plotted against luciferase concentration (FIG. 48; Reporter concentration 50 corresponds to 1280 femtograms luciferase). The signal was shown to be proportional to luciferase concentration over an at least 50 fold range with a linear correlation coefficient of r=0.99. The assay was highly accurate and reproducible as shown by the small standard deviations obtained from a total of 2,304 individual measurements obtained in a randomized fashion. As few as 200,000 molecules of luciferase can be detected in one well of a 96-well microtiter plate. When 10,000 cells expressing luciferase are plated into one well, as few as 20 molecules of luciferase per cell can thus be detected in a simple, high-throughput, fully automatable format. Thus the novel lysis buffer described in Materials and Methods, Sections F and G, allows unique sensitivity and stability, accuracy and reproducibility of the luciferase-catalysed bioluminescent reaction and facilitates easy automation of the luciferase transcriptional reporter system. In all these qualities, the luciferase assay system using the lysis and reaction buffer described above not only surpasses other available luciferase assays but all other available transcriptional reporter technologies.

In vivo Signal Half-life of the Luciferase Reporter System

When screening for inhibitors rather than inducers of transcription, the half-life of the reporter molecule becomes a crucial parameter in determining the minimal incubation time that would be necessary to allow enough decay of reporter molecules so that the inhibition of their synthesis became visible. The cell lines G1002, GM1074 and CM1 containing luciferase reporter constructs for the G-CSF, GM-CSF or the immediate early promoter of cytomegalovirus were therefore tested for the time dependency of luciferase activity after treatment of the cells with Actinomycin D, an inhibitor of transcription. This experiment measures the combined half-life of luciferase mRNA and of the luciferase protein. Cells derived from clones G 1002, GM 1074 and CM 1 were seeded into 96-well microtiter plates (20,000 cells G 1002 or GM 1074/well and 5000 cells CM 1/well) and incubated overnight in cell culture conditions. At time 0 Actinomycin D (25 microg/ml) was added. At the times indicated in FIG. 49 cells were washed with PBS and luciferase activity of Actinomycin-treated cells determined as described in Materials and Methods, Section G. was compared to the luciferase activity of untreated controls. The logarithm of the treated/untreated ratio is plotted versus time.

As demonstrated in FIG. 49, apparent half-lifes found in the three cell lines tested ranged from about 2.5 to 6 hours.

A 24 hour incubation with a 100% efficient inhibitor of transcription would therefore be sufficient to reduce luciferase levels to maximal 6% of the control in the tested cell lines.

B. Validation of Cell Lines

Figure 42:
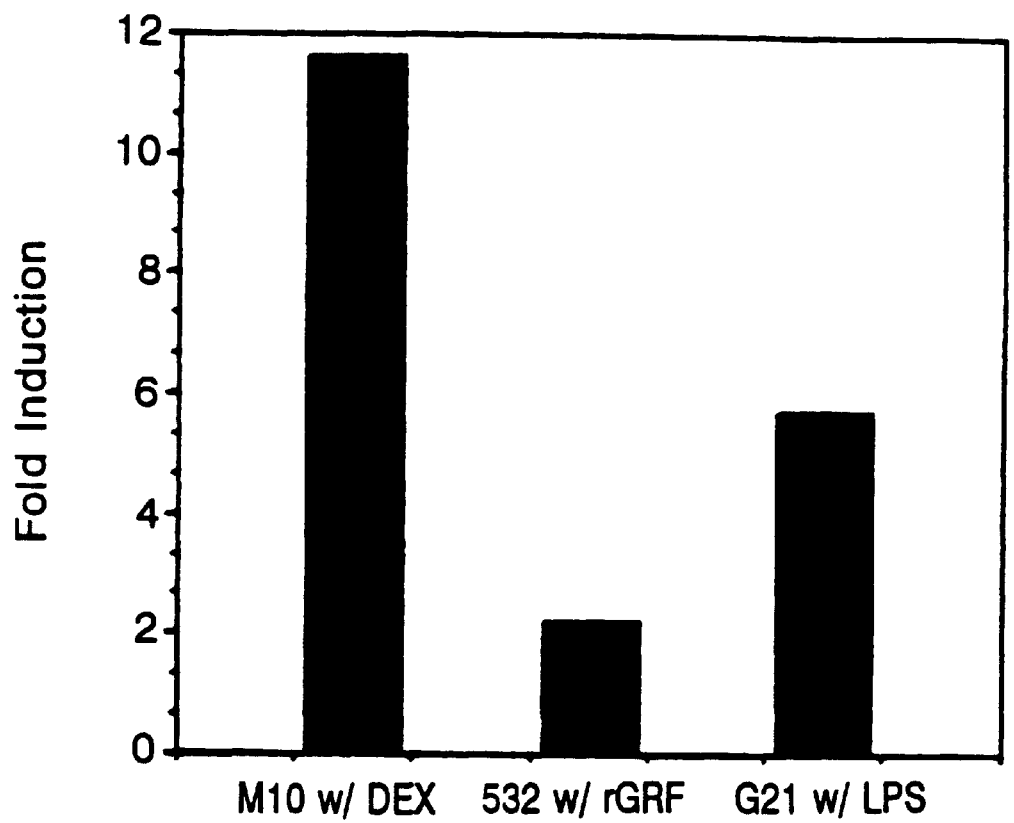
FIG. 42 is a bar graph illustrating induction of luciferase expression in reporter cell lines containing MMTV (M10), human growth hormone (532), and human G-CSF (G21) promoter sequences, in response to known transcriptional inducers.

Prior to initiation of drug screening, it was demonstrated that the transfected promoter-luciferase fusion plasmids were reacting to transcriptional inducers in a manner as predicted based on the published literature. As shown in FIG. 42, all three transfected cell clones chosen responded to inducers which have been reported to stimulate the endogenous genes; the MMTV-luciferase containing clone M10 was stimulated 11.6 fold by 1 $\mu$m dexamethasone, the hGH-luciferase containing clone 532, was stimulated 2.2 fold by 100 mM rat growth hormone releasing factor (GRF), and the hG-CSF containing clone G21 was stimulated 5.7 fold by 5 lg/ml lipopolysaccharide (LPS).

Figure 43:
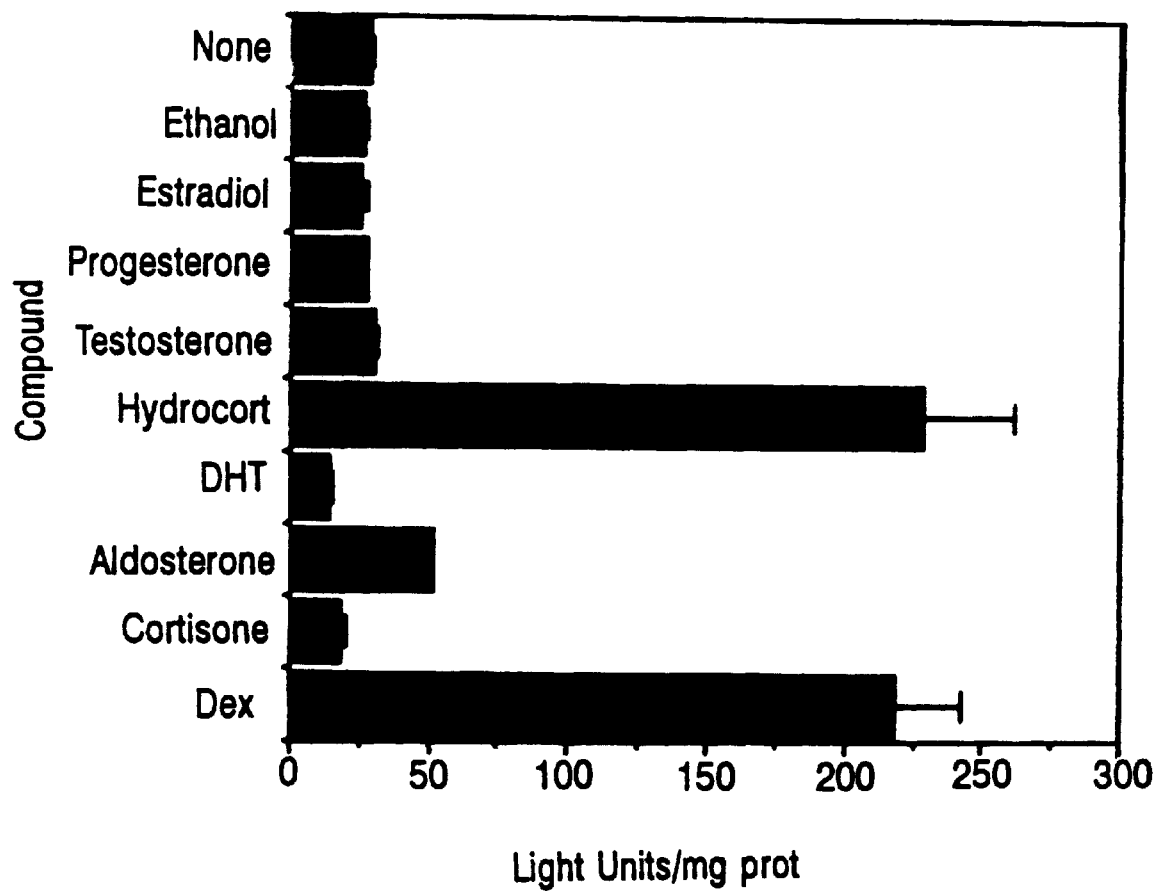
FIG. 43 is a bar graph illustrating the effect of steroids on luciferase expression in the MMTV reporter cell line M10.

It was also demonstrated that certain steroidal chemicals other than dexamethasone modulated luciferase expression in the cell clone M10, which harbours the MMTV promoter-luciferase fusion construct. As shown in FIG. 43, dexamethasone stimulated the MMTV promoter in cell clone M10 (mouse fibroblase origin), while progesterone did not. It has been shown that a rat fibroblast cell line which contains high levels of glucocorticoid receptor but low levels of progesterone receptor, shows stimulation of the MMTV promoter by the glucocorticoid dexamethasone but not by progesterone (7). In addition, FIG. 43 shows that the mineralocorticoid aldosterone stimulates clone M10, as is expected based on previously published work which indicates that aldosterone can act through the glucocorticoid receptor to stimulate the MMTV promoter (6).

Cell clones transfected with the OSI mammalian expression shuttle vector fused to the G-CSF, GM-CSF and M-CSF promoters (Materials and Methods, Sections E.4, E.5 and E.6) were analysed for correct and complete integration of the promoter/luciferase constructs by Southern blotting. Genomic DNA was prepared of each clone to be tested and restriction-cut with Dra I. Blots were probed with XbaI-EcoRI fragments of the luciferase coding region. Since Dra I cuts in the SV 40 polyadenylation sites located in the OSI mammalian expression shuttle vector just upstream the inserted promoter sequences as well as downstream of the luciferase coding region, but not in any of the 3 promoter sequences used for generating stably transfected cell clones, a single fragment should be visualized by the probe used. The size of that fragment should be characteristic for each of the three promoter sequences analyzed.

As shown in FIG. 50, G-CSF clones G 1002, G 3014 and G 3031, GM-CSF clones GM 1073, GM 1088 and GM 1105 and all 3 M-CSF clones tested contained only a single fragment with the correct molecular size (uppermost fragments in plasmid controls G/5637, M/HL 60 and GM/5637 generated by loading mixtures of the purified plasmids and extracts of the parental cell lines 5637 or HL 60 on the gel). The 2 smaller fragments are non-specific, cross-hybridizing probe impurities. The other clones all contained additional rearranged fragments of various molecular sizes. Conspicuously, all 3 G-CSF clones with correctly integrated promoter/reporter constructs were derived from electroporation, whereas the other G-CSF cell clones analysed were obtained either by lipofection (G 2005, G 2071 and G2085) or calcium phosphate precipitation (G 21; see Materials and Methods). Interestingly, G 21 cells contain multiple copies of the promoter/luciferase construct, the majority of which migrate at approximately correct molecular weight. The data suggest that electroporation under the optimized conditions described is the transfection method of choice to obtain cell clones with correctly integrated, complete promoter/luciferase reporter constructs.

Cell clones with correctly integrated promoter/reporter constructs were analysed for correct reaction to known transcriptional inducers. Of the G-CSF clones tested, G1002 showed the most consistent levels of induction after 10.5 hours of incubation in serum-containing media with 8.3 ng/ml tumor necrosis factor—alpha (TNF-alpha; 2 fold), 20 ng/ml phorbol-myristate-acetate (PMA; 4.4 fold), 0.5 ng/ml Interleukin—1 beta (2.6 fold), a mixture of 4.2 ng/ml TNF-alpha and 0.3 ng/ml Interleukin—1beta (3.8 fold) and a mixture of 4.2 ng/ml TNF-alpha and 10 ng/ml PMA (7.6 fold). Both TNF-alpha- and PMA-induction levels of clone G 1002 were influenced by the presence or absence of epidermal growth factor (EGF). 7-Hour incubations in serum-free defined media with 20 ng/ml EGF resulted in a 3 fold G-CSF promoter induction by TNF-alpha versus 4 fold in the absence of EGF. The 9.3 fold induction by PMA in the absence of EGF was reduced to 5.6 fold by including EGF in the serum-free incubation mixture. Similar differences were observed, when EGF was substituted by 10% fetal calf serum.

A 7-hour incubation of G 21 cells with PMA in serum-free media increased luciferase expression directed by the G-CSF promoter by 34.6 fold in the absence and by 24.6 fold in the presence of EGF. TNF-Alpha induction did not significantly change on EGF addition (2.8 fold with and 2.1 fold without EGF).

Promoter induction experiments were also conducted with the GM-CSF reporter cell lines GM 1073, GM 1088 and GM 1105, which were all shown to contain correctly inserted constructs (see above). 10.5 hours incubation of GM 1073 cells with 20 ng/ml PMA in serum-containing media resulted in a 3.4 fold induction of the GM-CSF promoter, which was increased to 7.5 fold in serum-free media. Luciferase expression of clones 1088 and 1105 was induced by PMA 2.8 fold and 2 fold, respectively, while TNF-alpha induced both clones 2 fold.

All three M-CSF clones responded to a 16-hour incubation with 2,000 units/ml Interferon-gamma by a 20-fold increase of luciferase expression from the M-CSF promoter.

All 3 GM-CSF clones described above attached to the well surfaces of microtiter plates after overnight incubation. Levels of luciferase expression from clone 1105 were not appreciably affected by the omission of the fibronectin-coating step before cell plating. Luciferase expression levels were strongly increased by fibronectin coating, however, when clones G 1002 or G21 were used (about 8 fold or 3 fold, respectively).

Clones GM 1088, GM 1073 and G 1002 consistently produced bioluminescence signals varying by less than 10% between wells, when multiple 96-well microtiter plates containing these cells were assayed.

To be able to screen large random collections of compounds it may be necessary to use a variety of solvents to account for different solubilities of the compounds of interest. The effect of three organic solvents, DMSO, methanol and ethanol, which are frequently used to dissolve screening samples, was therefore determined on three reporter cell lines. Cells of the lines G 2005, GM 1105 and M10 containing luciferase reporter constructs for the G-CSF, GM-CSF or the promoter of the mouse mammary tumor virus were seeded into 96 well microtiterplates (10,000 cells/well) and cultured overnight. Various amounts of DMSO, methanol or ethanol were added to cultures. Luciferase activity in the cells was determined 8 hours after addition of the solvents. The relative amount of luciferase activity compared to untreated controls is plotted versus solvent concentration (FIG. 51).

G2005 and GM1105, which were constructed using the same parental cell line show very similar behaviour. It seems that a final concentration of 1% can be used in each case.

C. High-Throughput Drug Screen

Table 1 shows a summary of the results of a one-week, high-throughput screen of 2,000 chemicals to identify those chemicals specifically stimulating or inhibiting transcription from the G-CSF, hGH or MMTV promoters.

This screen concurrently tested chemicals at three concentrations on quadruplicate samples of the M10, 532 and G21 cell lines. A minimum stimulation of one promoter, to the degree indicated, and less than 50% activation of the other two promoters was required for

TABLE 1

SUMMARY OF HIGH-THROUGHPUT SCREEN

Promoter

Number (%) of Chemicals Which Activate Expression:

| | 2–3 Fold | 3–5 Fold | 5–7 Fold | 7–10 Fold | >10 Fold | Total |
|---|---|---|---|---|---|---|
| G-CSF | NA | 23 (1.1%) | 10 (0.5%) | 3 (0.15%) | 2 (0.10%) | 38 (1.9%) |
| hGH | NA | NA | 12 (0.6%) | 5 (0.03%) | 6 (0.03%) | 23 (1.14%) |
| MMTV | 15 (0.7%) | 1 (0.05%) | 0 (0%) | 1 (0.05%) | 1 (0.05%) | 18 (0.9%) |

Number (%) of Chemicals Which Inhibit Expression >3 Fold

| G-CSF | 7 | (0.3%) |
|---|---|---|
| hGH | 42 | (2.1%) |
| MMTV | 1 | (0.05%) |

TABLE 2

| Chemical# | Chemical Name | GCSF | hGH | MMTV |
|---|---|---|---|---|

A) TRANSCRIPTIONAL ACTIVATORS

FOLD INDUCTION RELATIVE TO SOLVENT CONTROL

G-CSF:

| | | | | |
|---|---|---|---|---|
| 40 | 3-Acetyl-2-6-Bis(tertiary butyl amino)-4-methyl-pyridine | 5.62 | 0.82 | 0.27 |
| 58 | 1-Acetylimidazole | 6.03 | 0.17 | 0.42 |
| 237 | N-Carbethyoxy-phthalimide | 4.77 | 0.06 | 0.82 |
| 254 | 1-(2-Chloroethyl)piperidine | 4.09 | 0.90 | 0.98 |
| 364 | Melamine | 3.67 | 1.18 | 1.07 |
| 473 | 1,3,5,-Triazine | >3 | 0.50 | 0.87 |
| 542 | 5-Bromo-2'-deoxycytidine | 5.28 | 1.08 | 1.26 |
| 543 | 5-Bromo-2'-deoxyuridine | 7.17 | 0.72 | 0.98 |
| 878 | Blueberry leaf extract | 3.84 | 1.17 | 0.78 |
| 1025 | Culvers Root extract | 4.09 | 0.98 | 1.24 |
| 1234 | 4-Aminocinnemic Acid hydrochloride | 4.97 | 0.51 | 1.03 |
| 1255 | 1-Bromo-3,5-dichlorobenzene | 6.74 | 0.43 | 1.09 |
| 1374 | 4'-Amino-N-methylacetanilide | 11.03 | 0.05 | 1.05 |
| 1375 | 4'-(aminomethyl)benzene sulfonemide hydrochloride | 8.94 | 0.04 | 1.32 |
| 1376 | 2-Amino-5-Methyl benzene sulfonic acid | 6.37 | 0.04 | 1.32 |
| 1397 | 5-Amino-3-methylisothiazole hydrochloride | 3.63 | 0.57 | 1.13 |
| 1482 | 2-Aminophenyl disulfide | 3.99 | 0.54 | 1.07 |
| 1483 | 4-Aminophenyl disulfide | 4.64 | 0.38 | 1.09 |

FOLD INDUCTION

| 1521 | 2-Amino-6-purinethiol | 3.59 | 0.73 | 0.92 |
|---|---|---|---|---|
| 1583 | 8-Bromoedenosine | 5.82 | 0.12 | 0.86 |
| 1592 | Bis(2,2,3,3,4,4,5,5,6,6,7,7) dodecafluoroheptyl-(+)-camphorate | 3.20 | 0.74 | 1.34 |
| 1783 | Cupferron | 6.55 | 0.32 | 0.89 |
| 1793 | Cyanomethyl-N,N-dimethyl dithiocarbomate | 9.50 | 0.52 | 1.21 |
| 1994 | 3-Bromobiphenyl | 3.29 | 0.34 | 0.63 |
| 2001 | 1-Bromo-4-tertiary butyl benzene | 3.11 | 0.74 | 1.12 |
| 2030 | 4-Bromo-2-fluoro-6-nitroenizol | 5.53 | 0.87 | 0.87 |
| 2096 | (+)-1-Bromo-3-Chloro-2methyl propane | 3.27 | 0.75 | 0.95 |
| 2097 | 1-Bromo-5-Chloro pentane | 5.09 | 0.88 | 1.22 |
| 2129 | 4-Chlorobenzyl Chloride | 3.23 | 0.75 | 0.95 |

TABLE 2-continued

| Chemical# | Chemical Name | GCSF | hGH | MMTV |
|---|---|---|---|---|
| GROUP A: | | | | |
| 378 | 7-Oxo-7H-benzo[e]perimidine 4-carboxylic acid | 4.12 | 0.26 | 0.58 |
| 423 | Quinecrine dihydrochloride hydrate | 2.39 | 0.56 | 0.64 |
| 427 | Resazurin | 3.14 | 0.43 | 0.71 |
| 836 | Thionin | 3.20 | 0.23 | 0.58 |
| 1776 | Cresyl Violet Acetate | 3.50 | 0.15 | 1.36 |
| 1904 | 9-Aminoacridine hydrochloride | 4.12 | 0.54 | 0.82 |
| GROUP B: | | | | |
| 670 | Methyl Green | >3 | 0.52 | 0.79 |
| 1790 | Crystal Violet | 20.38 | 0.38 | 1.15 |
| GROUP A AND B: | | | | |
| 80 | Acridine Orange | 5.87 | 0.68 | 0.83 |
| hGH: | | | | |
| 70 | 2-Acetylpyrrole | 0.43 | 9.26 | 0.85 |
| 299 | 10,11-Dihydrocarbemezepine | 0.53 | 5.46 | 0.47 |
| 322 | 1-ethyl-2-benzimidazolinone | 0.60 | 11.18 | 1.12 |
| 325 | Fisetin | 0.14 | 5.42 | 1.0 |
| 552 | 3-(4-chlorophenyl)-1-methyoxy-1-methyl urea | 0.81 | 5.31 | 0.86 |
| 790 | Rivanol | 0.01 | 5.94 | 0.58 |
| 792 | Rose Bengel | 0.94 | 5.31 | 1.21 |
| 856 | Tripaumitin | 0.28 | 6.49 | 0.42 |
| 1004 | Arnica 4z | 0.85 | 6.48 | 0.42 |
| 1160 | Rochester # 6180 | 0.38 | 5.79 | 0.80 |
| 1251 | Bromocresol Green | 0.14 | 15.19 | 0.33 |
| 1337 | 4-Amino-5-hydroxy-1-nephthalene sulfonic acid | 0.07 | 15.87 | 0.23 |
| 1499 | 2-Amino-4-phenylthiazole hydrobromide monohydrate | 0.24 | 5.55 | 0.61 |
| 1550 | 2-Aminothiazole | 0.04 | 5.44 | 0.87 |
| 1552 | 2-amino-2-thiazole | 1.23 | 7.26 | 0.52 |
| 1561 | 4-Amino-3,5,6-trichloropicolinic acid | 0.23 | 8.05 | 0.48 |
| 1598 | N,N'-Bis-[3-(4,5-dihydro-1N-imidizol-2-yl)phenyl] urea dipropanoate | 0.72 | 5.32 | 1.27 |
| 1678 | 4,8-Bis(hydroxymethyl)-tricyclo [5,2,1,0$^{2,6}$]decane | 0.36 | 7.08 | 0.89 |
| 1740 | 5-carbethoxy-2-thiouracil | 0.74 | 17.77 | 0.87 |
| 1747 | $N_6$-carbobenzyloxy-L-lysine | 0.78 | 6.16 | 0.86 |
| 1804 | Cyclobutane carboxylic acie | 1.05 | 9.41 | 0.49 |
| 1876 | Alec Blue | 0.87 | 11.91 | 0.40 |
| 1881 | Alizarin Blue Black B | 0.21 | 18.87 | 0.69 |
| MMTV: | | | | |
| 189 | Bethocuproinedisulfonic Acid discodium salt hydrate | 1.06 | 1.47 | 2.80 |
| 453 | 2,2':6',2"-Terpyridine | 0.79 | 0.58 | 13.30 |
| 519 | b-Apo-8'-carptenal | 1.15 | 0.68 | 2.76 |
| 562 | Copaiva Balsam | 1.10 | 0.15 | 2.34 |
| 629 | Nomoveratric acid | 0.85 | 1.05 | 2.48 |
| 633 | 5-Iodorotic acid | 1.02 | 0.86 | 2.46 |
| 765 | Prednisolone-21-Acetate | 0.96 | 1.30 | 2.68 |
| 828 | 2,4,5,4'-Tetrachlorodiphenylsulfide | 1.47 | 1.34 | 2.20 |
| 848 | Triamcinolone acetonide | 0.75 | 1.28 | 2.43 |
| 944 | Peanut | 1.15 | 0.91 | 2.18 |
| 1269 | 5-Amino-4,6-dichloropyrimidine | 0.72 | 0.91 | 2.18 |
| 1316 | 2-Aminofluorene | 0.74 | 1.39 | 2.33 |
| 1318 | 2-Amino-9-fluorenone | 1.13 | 0.85 | 2.41 |
| 1384 | 2-Amino-4'-methylbenzophenone | 1.33 | 0.50 | 2.43 |
| 1573 | 5-Bromoacenaphthene | 1.49 | 0.34 | 4.30 |
| 2084 | 4-(Bromomethyl)-6,7-dimethoxy-coumarin | 0.82 | 1.10 | 2.53 |
| 2148 | 2-chlorocyclohexanone | 0.45 | 0.92 | 2.82 |
| 2191 | Chloramphenicaol | 0.37 | 0.35 | 7.32 |

TABLE 2-continued

Figure 44:
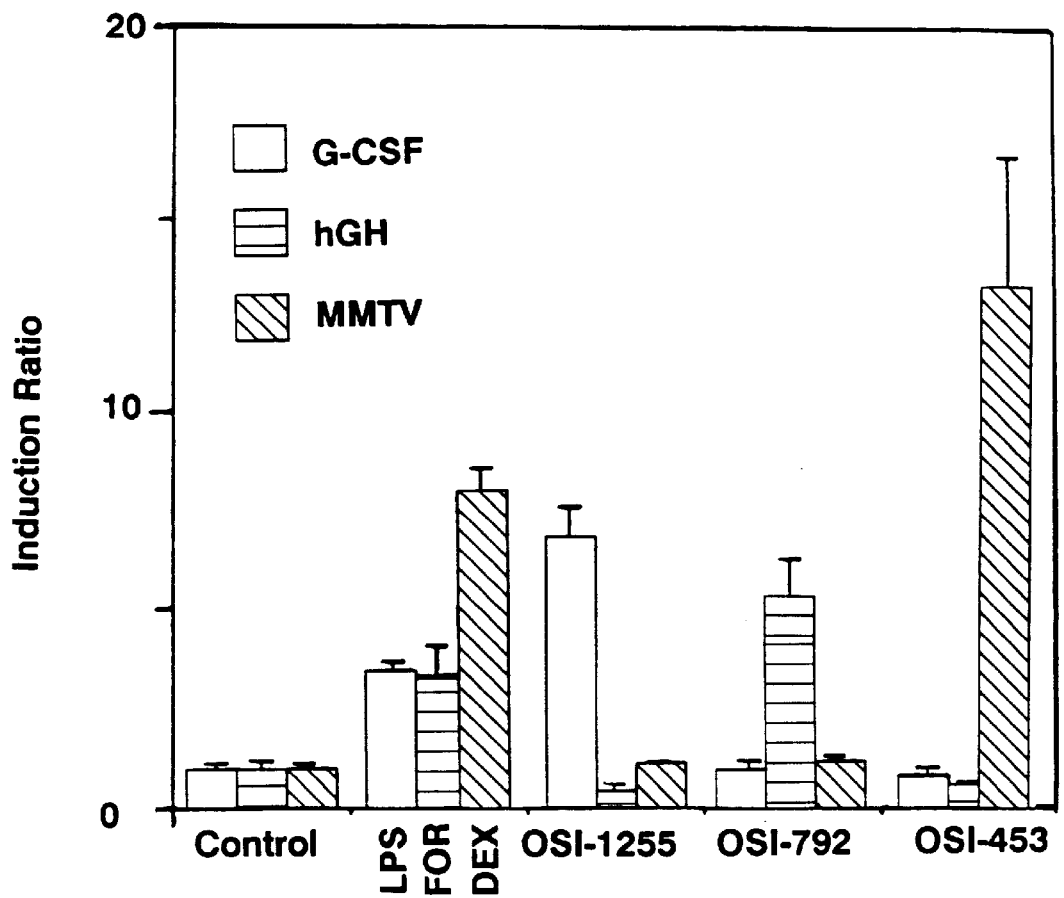
FIG. 44 is a bar graph illustrating specific induction of luciferase expression in reporter cell lines for MMTV (M10), human growth hormone (532) and human G-CSF (G21) promoters in response to chemicals identified in a high throughput screen and known transcriptional inducers.
Figure 45:
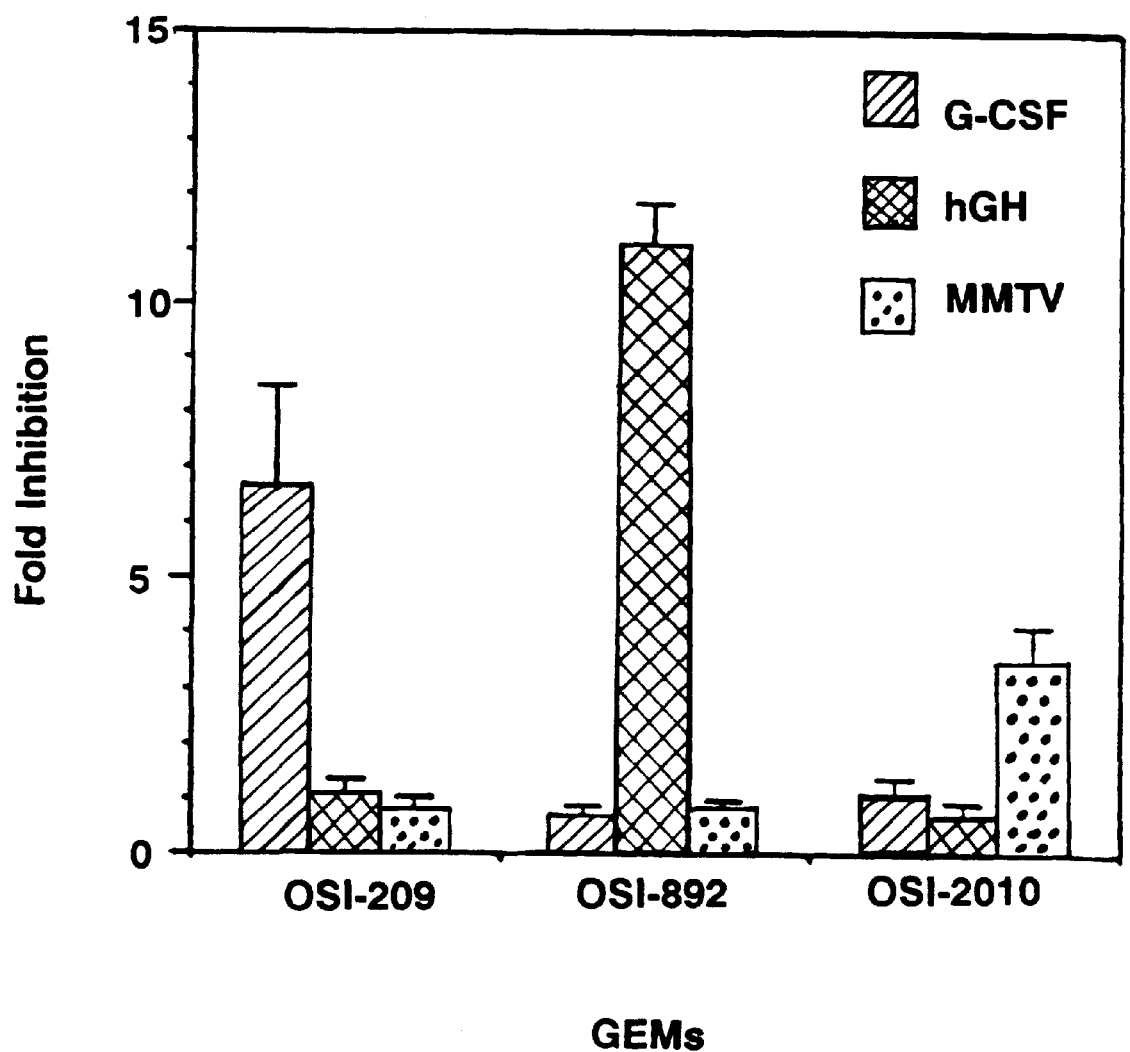
FIG. 45 is a bar graph illustrating specific inhibition of luciferase expression in reportor cell lines for MMTV (M10), human growth hormone (532), and human G-CSF (G21) in response to chemicals identified in a high throughput screen.

| Chemical# | Chemical Name | GCSF | hGH | MMTV |
|---|---|---|---|---|
| B) TRANSCRIPTIONAL INHIBITORS | | | | |
| | | FOLD INHIBITION RELATIVE TO SOLVENT CONTROL | | |
| G-CSF: | | | | |
| 209 | 4-Benzoylpyridine | 6.56 | 1.08 | 0.81 |
| 371 | Morin hydrate | 11.11 | 0.41 | 0.89 |
| 560 | Meclurin | 10.0 | 0.34 | 1.04 |
| 798 | Salicylamide | 4.76 | 0.90 | 0.68 |
| 2009 | 4-Bromo-3,5-dimethylpyrazole | 3.70 | 0.57 | 0.64 |
| 2082 | 4-Bromo-3-Methylpyrazole | 5.28 | 0.65 | 1.23 |
| 2121 | 3-Chlorobenzyl alcohol | 4.78 | 0.40 | 1.14 |
| hGH: | | | | |
| 183 | Auramine O | 0.72 | 4.00 | 0.70 |
| 240 | Carminic acid | 0.63 | 5.26 | 0.80 |
| 443 | Sulfamethazine | 0.60 | 4.76 | 0.79 |
| 512 | Amaranth | 0.81 | 5.26 | 0.66 |
| | | FOLD INHIBITION | | |
| 541 | 5-Bromo-4-Chloro-3-indoxyl-phospate K-salt | 0.90 | 5.25 | 0.86 |
| 556 | Chromazurol 5 | 0.73 | 33.33 | 0.87 |
| 561 | Clove Oil | 0.62 | 5.00 | 0.05 |
| 577 | Na-Ne-Diacetyl-L-lysine | 0.84 | 4.00 | 0.68 |
| 578 | Dibenzoyl-D-tartatic acid | 0.65 | 4.00 | 0.91 |
| 630 | Hydantoin-5-acetic acid | 0.70 | 3.57 | 0.74 |
| 640 | Kernechtrot | 0.64 | 5.00 | 0.59 |
| 759 | Piperidine | 0.64 | 5.88 | 0.95 |
| 764 | Prednisolone | 0.82 | 4.54 | 0.59 |
| 875 | Black Walnut extract | 0.59 | 5.25 | 0.80 |
| 892 | Colts Foot Leaves extract | 0.68 | 11.11 | 0.87 |
| 893 | Comfrey Leaf extract | 0.74 | 11.11 | 0.90 |
| 920 | Norehound Herb extract | 0.56 | 3.84 | 0.84 |
| 921 | Horsetail Grass extract | 0.72 | 3.44 | 0.86 |
| 942 | Pau D'Arco extract | 0.80 | 6.25 | 0.63 |
| 970 | Thyme extract | 0.57 | 4.34 | 1.07 |
| 1591 | 1,2-Bis(di-p-tolylphosphino)-ethane | 0.58 | 5.55 | 0.96 |
| 1604 | 2,4-Bis[5,6-bis(4-sulfophenyl)-1,2,4-Triazine-3-yl)-pyridine, tetrasodium salt hydrate | 0.77 | 5.00 | 0.97 |
| 1635 | [(1S)-endo-(−)-Sorneol] | 0.71 | 9.09 | 0.99 |
| 1640 | 1,2-Bis(2-pyridyl)-ethylene | 0.79 | 5.00 | 0.59 |
| 1641 | 2,3-Bis(2-pyridyl)-pyrazine | 0.83 | 5.55 | 0.80 |
| | | FOLD INHIBITION | | |
| 1548 | 2-[5,6-Bis(4-sulfophenyl)-1,2,4-triazine-3-yl]-4-(4-sulfophenyl)-pyridine, trisodium salt | 0.86 | 7.69 | 1.00 |
| 1651 | Bis(2,2,2-trifluoroethyl) (methocarbonyl-methyl)-phophonate | 0.59 | 3.57 | 0.70 |
| 1655 | 2,5-Bis(trifluoro-methyl)benzoic acid | 0.54 | 4.76 | 0.81 |
| 1703 | 3-Bromobenzonitrile | 0.76 | 10.00 | 0.90 |
| 1704 | 4-Bromobenzonitrile | 0.77 | 4.16 | 0.94 |
| 1705 | 4-Bromobenzophenone | 0.54 | 14.28 | 0.62 |
| 1712 | Calcein Blue | 0.74 | 8.33 | 0.94 |
| 1720 | (1S)-(−)-Camphor | 0.65 | 4.76 | 0.66 |
| 1764 | 7-(Carboxymethoxy)-4-Methylcoumarin | 0.55 | 7.14 | 0.82 |
| 1770 | Cerminic acid | 0.54 | 10.00 | 0.57 |
| 1771 | L-Carnosine | 0.71 | 10.00 | 0.72 |
| 1773 | D-Cresolphthelein Complexone | 0.62 | 10.00 | 0.67 |
| 1890 | Alloxazine | 0.80 | 5.26 | 0.58 |
| 2035 | 5-Bromofuroic acid | 0.57 | 7.14 | 0.89 |
| 2036 | 6-Bromoguanosine | 0.58 | 4.34 | 0.81 |
| 2037 | 1-Bromohexadecane | 0.51 | 4.00 | 0.50 |
| MMTV: | | | | |
| 2010 | 2-Bromo-4,5-dinitroaniline | 0.80 | 0.63 | 3.57 | a chemical to be considered a selective activator. A minimum inhibition of 3 fold of one promoter and less than 20% inhibition of the other two promoters was required for a chemical to be considered a selective inhibitor. Table 2 gives the names and induction or inhibition ratios of the lead chemicals identified for each promoter. FIG. 44 illustrates the transcriptional stimulation and FIG. 45 the transcriptional inhibition observed with some of the lead chemicals. Some of the chemicals activating G-CSF transcription fell into conspicuous groups of analogs (Table 2; Group A and B). Although not specifically indicated in Table 2, groups of homologs and analogs can also be found for G-CSF-inhibiting as well as hGH-activating chemicals.

To determine the number of lead chemicals, which reproducibly score as positives in repeated luciferase assays, two types of experiments were conducted:

1) G-CSF lead chemicals #1780, #58, #1783, #1374 were subjected to 48 independent luciferase assays performed on the same day. Compounds #58, #1780 and #1374 scored as positives in every single one of these assays inducing luciferase expression between 2 and 28fold (#58), 20 and 80fold (#1780) and 5 and 40fold (#1374). Probably due to its relatively low induction of luciferase expression (1.5 to 8fold), Compound #1783 scored as positive only in half of the 48 repeat assays.

2) All of the 18 lead chemicals inducing luciferase expression from the MMTV promoter were again subjected to luciferase assays: 10 chemicals (#453, #519, #562, #765, #828, #848, #1269, #1316, #1384 and #2148) again induced luciferase expression between 2.1 and 2.8fold. Probably due to the relatively low induction level close to the background of the assay, the other eight lead chemicals did not repeat on that particular day. The most prominent lead chemical, #453 (13.3fold induction in the original high-throughput assay), was repeated in a total of 3 independent assays and consistently induced luciferase expression from the MMTV promoter between 10 and 35fold. Replacing DMSO by methanol to dissolve the chemical did not affect its ability to activate the MMTV promoter.

Aqueous clarified supernatants derived from individual Actinomyces colonies prepared by standard methods known to those skilled in the art as well as corresponding methanol extracts were subjected at 1:10 initial dilution to a fully automated, robotic High-Throughput luciferase assay using the system described in U.S. patent application Ser. No. 382,483. Out of 356 samples tested for modulation of the G-CSF, GM-CSF and MMTV promoters, 25 samples scored as positives, 7 of which were promoter-specific. A summary of the obtained results is contained in FIGS. 52 and 53. Thus, high-throughput screening of fermentation broth samples using a luciferase expression assay consistently leads to the discovery of lead samples with the potential to be developed into novel pharmaceuticals.

D. Effects of Lead Chemicals on Endogenous G-CSF mRNA Levels

Figure 46:
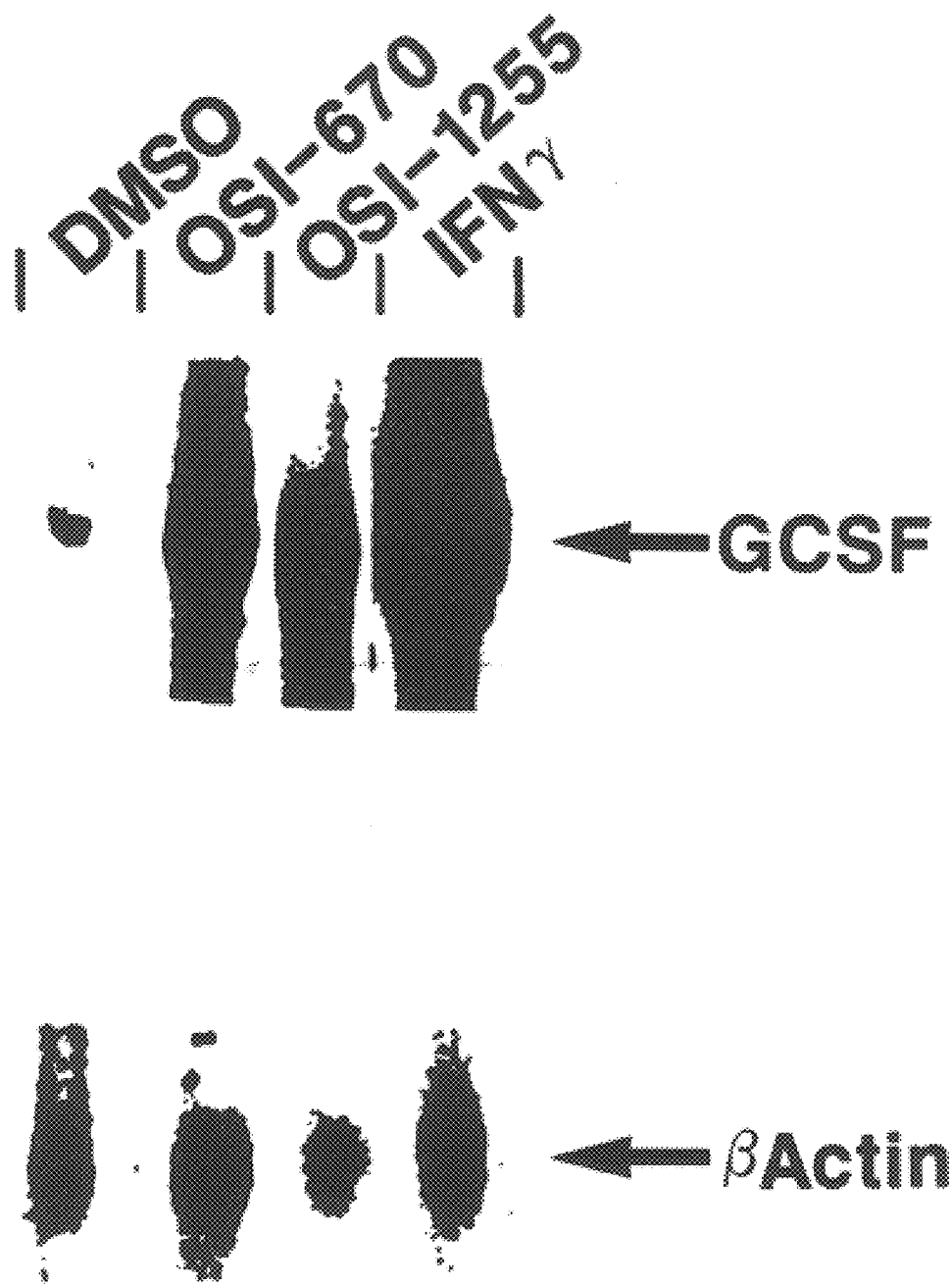
FIG. 46 is an autoradiograph of a Northern blot illustrating increased G-CSF mRNA production by the human epithelial cell line U5637 in response to chemicals #670 and #1255 and IFN-gamma as compared to the solvent DMSO.

Northern blot analysis was used to demonstrate the stimulatory effects of lead chemicals #670 and #1255 on endogenous G-CSF mRNA levels. As shown in FIG. 46, both OSI #670 and #1255 stimulated production of G-CSF mRNA, as shown by a G-CSF-specific probe, but not of actin mRNA, as shown by a b-actin-specific probe. Also shown are the effects of the solvent, DMSO, used to dissolve the chemicals and a proteinaceous positive regulator, interferon-gamma. From these data it is concluded that chemicals, which induce luciferase expression from specific promoters, in plasmids stably integrated into cells, are also capable of stimulating mRNA production from the corresponding endogenous promoters without using a reporter system. To further confirm, that compounds that had been identified in a luciferse expression assay using a G-CSF specific reporter cell line would be active in inducing transcription of the endogenous G-CSF gene, cells from the parental cell line 5637 used to construct the reporter cell line were incubated with cycloheximide (25 microg/ml), DMSO (0.5%, solvent control) and low, medium and high concentrations of the compounds 542 (10, 50, 250 microM), 1255 (20, 100, 500 microM), 1793(0,25, 1.2, 6.25 microM), 1904 (20, 100 microM) for 18 hours. RNA was extracted and the concentration of G-CSF, GM-CSF and gamma-actin mRNA was determined by the S1 protection method as described in Materials and Methods. The positions of G-CSF GM-CSF and gamma-actin specific protected fragments are indicated (G, GM, A) at the left side of the gel (FIG. 54).

Interestingly, all four compounds tested increased the amount of G-CSF mRNA and at least two of them, namely #542 and #1793, also increased the amount of GM-CSF mRNA. Compound #543, a structural analog of #542 showed similar activity.

E. Dose response Analysis of Structurally Related Lead Chemicals

Among the chemicals which specifically activated the G-CSF promoter were groups of structural homologs. Three such homologs, #80, #670, and #1780, belong to groups listed in Table 2. These three structurally related chemicals all specifically activated the G-CSF promoter. Dose response graphs obtained with chemicals #80, #670, and #1780 are shown in FIG. 47. Although these chemicals all demonstrate large maximal stimulations, it is clear that their potencies, as measured by their $ED_{50}$'s (concentration of chemical resulting in 50% maximal stimulation), show wide variabilty (5–70 $\mu$m).

F. Effects of Lead Chemicals on Target Protein Secretion

Two of the most promising lead chemicals (#542 and #1780), which were shown to stimulate levels of endogenous G-CSF mRNA as well as luciferase expression from the G-CSF promoter/luciferase fusion constructs, were further investigated for their ability to increase G-CSF secretion into the media of 5637 bladder carcinoma cells incubated with the chemicals for 48 hours. The levels of G-CSF in the cell supernatants were determined by a sandwich-antibody assay as described in Materials and Methods (FIG. 55).

G. Cytotoxicity of Lead Chemical #542

To address the question whether the induction of G-CSF, and GM-CSF transcription by the compound #542 was a specific effect or rather a phenomenon linked to a potential sensitivity of these promoters to stress exerted by toxic compounds, the concentration dependency of induction of luciferase activity in the reporter cell line G21 was compared to the concentration dependency of inhibition of respiration in FRE cells. Cells were seeded into 96 well microtiterplates (20 000 cells/well) and cultured overnight. Compound #542 was added at various concentrations and the cells were incubated for 6 hours. Luciferase activity was determined as described in Materials and Methods. The MTT-colorimetric assay was carried out on identically treated samples of FRE cells. Induction of luciferase reporter signal (plain line) and on inhibition of respiration (dashed line) are plotted versus the concentrations of compound (FIG. 56). The ED50 for induction of luciferase activity differed from the ED50 for inhibition of respiration by a factor of almost 10, which might indicate that compound #542 exerts a specific effect on G- and GM-CSF transcription.

H. Luciferase expression assay in yeast

To determine, wheter the luciferase expression assay would also be useful to study other than mammalian cells, a yeast expression plasmid carrying the luciferase gene under control of a yeast promoter was constructed and transfected into appropriate yeast cells. Using these cells as a model system, a format for a 96-well luciferase expression assay in yeast cells was developed as described in more detail in Materials and Methods.

REFERENCES

1. Angel, P., Baumann, I., Stein, B., Delius, H., Rahmsdorf, H. J. and Herrlich, P. (1987) 12-0-tetradecanoyl-phorbol-13-acetate (TPA) induction of the human collagenase gene is mediated by an inducible enhancer element located in the 5'-flanking region. Mol. Cell. Biol. 7:2256
2. Angel, P., Imagawa, M., Chiu, R. Stein, B., Imbra, R. J., Rahmsdorf, H. J., Jonat, C., Herrlich, P. and Karin, M. (1987) Phorbol ester-inducible genes contain a common cis element recognized by a TPA-modulated trans-acting factor, Cell, 49:729.
3. Arnheim, N. (1979) Characterization of mouse ribsomal gene fragments purified by molecular cloning, Gene 7:83.
4. Bancroft, F. C., Wu, G. J., and Zubay, G. (1973) Proc. Natl. Acad. Sci. USA, 73:29.
5. Bottenstein, J., Hayashi, I., Hutchings, S., Masui, H., Mather, J., McClure, D. B., Ohasa, S., Rizzino, A., Sato G., Serrero, G., Wolfe, R., and Wu, R. (1979) The growth of cells in serum-free hormone-supplemented media, Methods in Enzymology, 58:94.
6. Cato, A. C. B. and Weinmann, J. (1988) Mineralcorticoid regulation of transcription of transfected mouse mammary tumor virus DNA in cultured kidney cells, J. Cell Biol., 106(6):2119.
7. Cato, A. C. B., Miksicek, R., Schutz, G., Arnemann, J., and Beato, M. (1986) The hormone regulatory element of mouse mamary tumor virus mediates progesterone induction, EMBO J., 5(9):2237.
8. De Wet, J. G., Wood, K. V., Helinski, D. R., and DeLuca, M. (1985) Cloning of firefly luciferase cDNA and the expression of active luciferase in *Escherichia coli*, Proc. Natl. Acad. Sci. USA. 82:7870.
9. Dension, M. S., Fisher, Springfield, N.J. J. M., and Whitlock, Jr., J. P. (1988) Inducible, receptor-dependent protein-DNA interactions at a dioxin-responsive transcriptional enhancer, Proc. Natl. Acad. Sci. USA, 85:2528.
10. Edeµman, A. M., Blumenthal, D. R. and Krebs, E. G. (1987) Protein Serine/Threonine Kinases Ann. Rev. 56:567–613.
11. Engebrecht, J. M., Simon, M., and Silverman, M. (1985) Measuring gene expression with light. Science, 227:1345.
12. Evans, R. M. and Hollenberg, S. M. (1988) Zinc fingers: Gilt by association, Cell, 52:1.
13. Evans, R. M. (1988) The steroid and thyroid hormone receptor superfamily, Science, 240:889.
14. Gorman, C. (1985) Vectors used in mammalian cell expression. In DNA Cloning, Vol. II (D. M. Glover, ed). IRL Press, Washington, D.C.
15. Graham, F. L. and Van der Ed, A. J. (1973) A new technique for the assay of human adenovirus 5 DNA, Virology, 52:456.
16. Hatzopoulos, A. K., Schlokat, U., and Gruss, P. (1988) Enhancers and other cis-acting regulatory sequences. In Transcriptional and Splicing. (Hames, B. D. and Glover, D. M., eds.) IRL Press, Washington, D.C., Vol. 1, p. 43.
17. Hayashi, I., Larner, J., and Sato, G. (1978) Hormonal growth control of cells in culture., In Vitro, 14:23.
18. Hoeffler, J. P., Meyer, T. E., Yun, Y., Jameson, J. L., and Habener, J. F. (1988) Cyclic AMP-responsive DNA-binding protein: Structure based on a cloned placental cDNA, Science, 242:1430.
19. Hoopes, B. C. and McClure, W. R. Strategies in Regulation of Transcription Initiation. In *Escherichia coli* and Saumonella Typhimurium: Cellular and Molecular Biology (F. C. Neidhardt, J. L. Ingraham, K. Brooks Low, B. Magasanik, M. Schaechter, eds.) Vol. 2, p. 1231.
20. Kaushansky, K., O'Hara, P. H., Berkner, K., Segal, G. M., Hagen, F. S., and Adamson, J. W. (1986) Genomic cloning, characterization, and multilineage growth-promoting activity of human granulocyte-macrophage colony-stimulating factor, Proc. Natl. Acad. Sci. USA, 83:3101.
21. Krainer, A. R. and Maniatis, T. (1988) RNA splicing. In Transcription and Splicing (Hames, B. D. and Glover, D. M., eds.) IRL Press, Washington, D.C., Vol. 1.
22. La Thanque, N. B. and Rigby, P. W. H. (1988) Transacting protein factors and the regulation of eukaryotic transcription. In Transcription and Splicing (Hames, B. D. and Glover, D. M., eds) IRL Press, Washington, D.C., Vol. 1.
23. Ladner, M. B., Martin, G. A., Noble, J. A., Nikoloff, D. N., Tal, R., Kawaski, E. S., and White, T. J. (1987) Human CSF-1; gene structure and alternative splicing of mRNA precursors, EMBO J., 6:2693.
24. Landschulz, W. H., Johnson, P. F., and McKnight, S. L. (1988). The leucine zipper: A hypothetical structure common to a new class of DNA binding proteins, Science, 240:1759.
25. Lefevre, C., Imagawa, M., Dana, S., Grindlay, J., Bodner, M., and Karin, M. (1987) Tissue-specific expression of the human growth hormone gene is conferred in part by the binding of a specific trans-acting factor, EMBO J., 6:971.
26. Levine, M. and Hoey, T. (1988) Homeobox proteins as sequence-specific transcription factors, Cell, 55:537.
27. Lin, F. K., Suggs, S., Lin, C. H, Browne, J. K., Smalling, R. Egrie, J. C., Chen, K. K., Fox, G. M., Martin, F., Stabinsky, Z., Badrawi, S. M., Lai, P. H., and Goldwasser, E. (1985) Cloning and expression of the human erythropoietin gene, Pro. Natl. Acad. Sci. USA, 82:7580.
28. Maniatis, T., Goodbourn, S. and Fischer, J. A. (1987) Regulation of inducible and tissue-specific gene expression, Science, 236:1237.
29. Matthews, B. W. (1987) Cro repressor structure and its interaction with DNA. In DNA: Protein Interactions and Gene Regulation (E. B. Thompson and J. Papaconstantinou, eds.) University of Texas Press, Austin.
30. McClure (1985) Ann. Rev. Biochem., 54:171.

31. McKnight S. L. (1982) Functional relationships between transcriptional control signals of the thymidine kinase gene of herpes simplex virus, Cell, 31:355.
32. Nagata, S., Tsuchiya, M., Asano, S., Yamamotor, O., Hirata, Y., Kubota, N., Oheda, M., Nomura, H. and Yamazaki, T. (1986) The chromosomal gene structure and two mRNAs for human granulocyte colony-stimulating factor, EMBO J., 5:575.
33. Ow, D. W., Wood, K. U, Deluca, M, Dewet, J. R., Melinski, D., ad Howell, S. H. Science 234:856–859
34. Pouwels, Ph. H., Enger-Valk, B. E., and Brammar, W. J. (1985) Cloning Vectors. Elsevier Science Publishers, B. V., Amsterdam.
35. Proudfoot, N. J. and Whitelaw, E. (1988) Termination and 3' end processing of eukaryotic RNA. In Transcription and Splicing (Hames, B. D. and Glover, D. M., eds.) ERL Press, Washington, D.C., Vol. 1, p. 97.
36. Schlief, R. The L-Arabinose Operon. In *Escherichia coli* and *Salmonella typhimurium*: Cellular and Molecular Biology (F. C. Neidhardt, J. L. Ingraham, K. Brooks Low, B. Maga Sanik, M. Schaecter, eds.) Vol. 2, p. 1473.
37. Schlief, R. (1988) DNA binding by proteins, Science, 241:1182.
38. Yamamoto, K. R. (1985) Steroid receptor regulated transcription of specific genes and gene networks, Ann. Rev., Genet., 19:209.
39. Yamamoto, K. K., Gonzalez, G. A., Biggs III, W. H., and Montminy, M. R. (1988) Phosphorylation-induced binding and transcriptional efficacy of nuclear factor CREB, Nature, 334:494.
40. Yang, Y. C., Ciarletta, A. B., Temple, P. A., Chung, M. P., Kovacic, S., Witek-Gianotti, J. S., Learyn, A. C., Kriz, R., Donahue, R. E., Wong, G. G., and Clark, S. C. (1986) Human IL-3 (multi-CSF): Identification by expression cloning of a novel hematopoietic growth factor related to murine IL-3, Cell, 47:3.
41. Yang, T. C. and Clark, S. C. (1988) Molecular cloning of a primate cDNA and the human gene for interleukin 3, Lymphokines, 15:375.
42. Yanofsky, C. and Crawford, I. P. The Tryptophan Operon. In *Escherichia coli* and *Salmonella typhimurium*: Cellular and Molecular Biology (F. C. Neidhardt, J. L. Ingraham, K. Brooks Low, B. Magasanik, M. Schaechter, eds.) Vol. 2, p. 1453.
43. Zhan, A., Culpepper, A., Reddy, M., Loveless, J., and Goldfarb, M. (1987) Human oncogenes detected by a defined medium culture assay, Oncogene, 1:369.
44. Thomas, K. R. and Capecchi, M. R., Cell, 1987, 51:503–512.
45. Mansour, S. L., Thomas, K. R. and Capecchi, M. R., Nature, 1988, 366:348–352
46. M. R. Capecchi, 1989, Science, 244:1288–1292.
47. J. Thompson and D. Gillespie (1987) Molecular hybridization with RNA probes in concentrated solutions of guanidine thiocyanate, Anal. Biochem. 163:281–291.
48. J. Thompson, R. Solomon, K. Pellegrino, K. Sakai, M. Lewin, M. Feild, M. Castrovinci, L. Sacramone and D. Gillespie (1989) A noise-free molecular hybridization procedure for measuring RNA in cell lysates, Anal. Biochem. 181:371–378.
49. M. S. Urdea, J. A. Running, T. Horn, J. Clyne, L. Ku and B. D. Warner (1987) A novel method for the rapid detection of specific nucleotide sequences in crude biological samples without blotting or radioactivity; application to the analysis of hepatitis B virus in human serum, GENE 61:253–264.
50. B. Chu and L. Orgel (1989) Target nucleic acid amplification/detection systems, WO 90/03445, published Apr. 5, 1990. Applicant: The Salk Institute for Biological Studies.
51. E. Oura (1983) "Biomass from Carbohydrates" In Biotechnology, Vol 3, Chpt. 1a (ed H. Dellweg) VCH Press, Germany.
52. A. Einsele (1983) "Biomass from Higher n-Alkanes" In Biotechnology, Vol 3, Chpt. 1b (ed H. Dellweg) VCH Press, Germany.
53. U. Faust and P. Prave (1983) "Biomass from Methane and Methanol" In Biotechnology, Vol 3, Chpt. 1c (ed H. Dellweg) VCH Press, Germany.
54. R. J. Quinlan and S. G. Lisansky (1983) "Microbial Insectidides" In Biotechnology, Vol 3, Chpt. 2e (ed H. Dellweg) VCH Press, Germany.
55. N. Kosaric, A. Wieczorek, G. P. Cosentino, R. J. Magee and J. E. Prenosil (1983) "Ethanol Fermentation" In Biotechnology, Vol 3, Chpt. 3a (ed H. Dellweg) VCH Press, Germany.
56. M. Rohr, C. P. Kubicek and J. Kominek (1983) "Citric Acid" In Biotechnology, Vol 3, Chpt. 3d (ed H. Dellweg) VCH Press, Germany.
57. M. Rohr, C. P. Kubicek and J. Kominek (1983) "Gluconic Acid" In Biotechnology, Vol 3, Chpt. 3e (ed H. Dellweg) VCH Press, Germany.
58. K. Soda, H. Tanaka and N. Esaki (1983) "Amino Acids" In Biotechnology, Vol 3, Chpt. 3g (ed H. Dellweg) VCH Press, Germany.
59. G. W. Barnard and D. O. Hall (1983) "Energy from Renewable Resources" In Biotechnology, Vol 3, Chpt. 4 (ed H. Dellweg) VCH Press, Germany.
60. A. Kuninaka (1986) "Nucleic Acids, Nucleotides, and Related Compounds" In Biotechnology, Vol 4, Chpt. 4 (eds H. Pape and H. -J. Rehm) VCH Press, Germany.
61. H. Kleinkauf and H. van Dohren (1986) "Peptide Antibiotics" In Biotechnology, Vol 4, Chpt. 10 (eds H. Pape and H. -J. Rehm) VCH Press, Germany.
62. S. Umezawa, S. Kondo and Y. Ito (1986) "Aminoglycoside Antibiotics" In Biotechnology, Vol 4, Chpt. 11 (eds H. Pape and H. -J. Rehm) VCH Press, Germany.
63. S. Omura and Y. Tanaka (1986) "Macrolide Antibiotics" In Biotechnology, Vol 4, Chpt. 12 (eds H. Pape and H. -J. Rehm) VCH Press, Germany.
64. Z. Hostalek and Z. Vanek (1986) "Tetracyclines" In Biotechnology, Vol 4, Chpt. 13 (eds H. Pape and H. -J. Rehm) VCH Press, Germany.
65. G. Lancini (1986) "Ansamycins" In Biotechnology, Vol 4, Chpt. 14 (eds H. Pape and H. -J. Rehm) VCH Press, Germany.
66. J. Berdy (1986) "Further Antibiotics with Practical Application" In Biotechnology, Vol 4, Chpt. 15 (eds H. Pape and H. -J. Rehm) VCH Press, Germany.
67. H. Kobel and J. -J. Sanglier (1986) "Ergot Alkaloids" in Biotechnology, Vol 4, Chpt. 18 (eds H. Pape and H. -J. Rehm) VCH Press, Germany.
68. T. Anke (1986) "Further Secondary Products of Biotechnological Interest" In Biotechnology, Vol 4, Chpt. 19 (eds H. Pape and H. -J. Rehm) VCH Press, Germany.

69. J. Berlin (1986) "Secondary Products from Plant Cell Cultures" In Biotechnology, Vol 4, Chpt. 20 (eds H. Pape and H. -J. Rehm) VCH Press, Germany.
70. L. L. Smith (1984) "Steroids" In Biotechnology, Vol 6a, Chpt. 2 (ed K. Kieslich) VCH Press, Germany.
71. C. K. A. Martin (1984) "Sterols" In Biotechnology, Vol 6a, Chpt. 3 (ed K. Kieslich) VCH Press, Germany.
72. V. A. Krasnobajew (1984) "Terpenoids" In Biotechnology, Vol. 61, Chpt. 4 (ed K. Kieslich) VCH Press, Germany.
73. A. Kergomard (1984) "Alicyclic and Heteroalicyclic Compounds" In Biotechnology, Vol 6a, Chpt. 5 (ed K. Kieslich) VCH Press, Germany.
74. O. K. Sebek (1984) "ANtibiotics" In Biotechnology, Vol 6a, Chpt. 7 (ed K. Kieslich) VCH Press, Germany.
75. P. R. Wallnofer and G. Engelhardt (1984) "Aromatic and Heterocyclic Structures" In Biotechnology, Vol 6a, Chpt. 8 (ed K. Kieslich) VCH Press, Germany.
76. M. Buhler and J. Schindler (1984) "Aliphatic Hydrocarbons" In Biotechnology, Vol 6a, Chpt. 9 (ed K. Kieslich) VCH Press, Germany.
77. G. Schmidt-Kastner and P. Egerer (1984) "Amino Acids and Peptides" In Biotechnology, Vol 6a, Chpt. 10 (ed K. Kieslich) VCH Press, Germany.
78. A. Crueger and W. Crueger (1984) "Carbohydrates" In Biotechnology, Vol 6a, Chpt. 11 (ed K. Kieslich) VCH Press, Germany).
79. P. F. Heinstein and A. Emery (1988) "Processes with Plant Cell Cultures" In Biotechnology, Vol 6b, Chpt. 9 (ed H. -J. Rehm) VCH Press, Germany.
80. M. Butler (1988) "Processes with Animal Cell and Tissue Cultures" In Biotechnology, Vol 6b, Chpt 10 (ed H. -J. Rehm) VCH Press, Germany.
81. A. E. Torma (1988) "Biosensors and 'Bioelectronics'" In Biotechnology, Vol. 6b, Chpt 12 (ed H. -J. Rehm) VCH Press, Germany.
82. S. Kunst and K. Mudrack (1988) "Microbial Elimination of Nitrogen and Phosphorus" In Biotechnology, Vol 6b, Chpt 14 (ed H. -J. Rehm) VCH press, Germany.
83. E. -J. Nyns (1986) "Biomethanation Processes" In Biotechnology, Vol 8, Chpt. 5 (ed W. Schonborn) VCH press, Germany.
84. T. Leisinger and W. Brunner (9186) "Poorly Degradable Substances" In Biotechnology, Vol 8, Chpt 14 (ed W. Schonborn) VCH press, Germany.
85. S. Lafon-Lafourcade (1983) "Wine and Brandy" In Biotechnology, Vol 5, Chpt 2 (ed G. Reed) VCH press, Germany.
86. W. A. Hardwick (1983) "Beer" In Biotechnology, Vol 5, Chpt 3 (ed G. Reed) VCH press, Germany.
87. E. R. Vedamuthu and C. Washam (1983) "Cheese" In Biotechnology, Vol 5, Chpt 4 (ed G. Reed) VCH press, Germany.
88. V. Bottazzi (1983) "Other Fermented Dairy Products" In Biotechnology, Vol 5, Chpt 5 (ed G. Reed) VCH press, Germany.
89. D. W. Ow, K. V. Wood, M. DeLuca, J. R. DeWet, D. R. Helinski, S. H. Howell (1986) Transient and stable expression of the firefly luciferase gene in plant cells and transgenic plants. Science 234:836–839.
90. D. R. Edwards and J. K. Heath (1990) "Regulation of transcription by transforming growth factor-β" In Molecular Aspects of Cellular Regulation, Vol 6, Elsevier Biomedical Press, in press.
91. Transcription and Splicing (1988) In the series Frontiers in Molecular Biology, ed. B. D. Hames and D. M. Glover, IRL Press, UK.
92. Southern, E. (1980) Methods in Enzymology, 69:152.
93. Feinberg, A. and Vogelstein (1984) Anal. Biochem. 137:266.
94. Sambrook, J., Fritsch, E. F. and Maniatis, T. (1989) Molecular Cloning. Cold Spring Harbor Laboratory Press, 1:7.58.
95. Cole, S. P. C. (1986) Rapid chemosensitivity testing of human lung tumor cells using the MTT assay. Cancer Chemother. Pharmacol., 17:259.
96. Harlow, E. and Lane, D. (1988). Antibodies—A Laboratory Manual. Cold Spring Harbor Laboratory Press, page 578.
97. Teem, J. L. and Rosbash, M. (1983) Proc. Natl. Acad. Sci. USA 80:4403–4407.
98. Pikielny, C. W., Teem, J. L., and Rosbash, M. (1983) Cell 34:395–403.
99. Sherman, F., Fink, G. R., Hicks, J. B. (1986) Laboratory Course Manual for Methods in Yeast Genetics, Cold Spring Harbor Laboratory, Cold Spring Harbor, N.Y.

What is claimed is:

1. A method of specifically transcriptionally modulating the expression of a gene of interest which encodes a protein, the expression of which is associated with a defined physiological or pathological effect within a multicellular organism, which comprises containing a eukaryotic cell, which expresses the gene, with a chemical at a concentration effective to specifically transcriptionally modulate expression of the gene and thereby affect the level of the protein encoded by the gene of interest which is expressed by the cell, which chemical (a) does not naturally occur in the cell,
(b) specifically transcriptionally modulates expression of the gene of interest, and
(c) binds to a protein which either:
  (i) is not a receptor protein associated with a defined physiological effect, or
  (ii) if it is a receptor protein associated with a defined physiological effect, the chemical binds to said receptor protein through a domain which is not a ligand binding domain normally associated with the defined physiological effect.

2. The method of claim 1, wherein the cell is a cell of the multicellular organism.
3. The method of claim 1, wherein the cell is a human cell.
4. The method of claim 1, wherein the cell is a animal cell.
5. The method of claim 1, wherein the cell is a plant cell.
6. The method of claim 1, wherein the gene of interest is a human gene.
7. The method of claim 1, wherein the gene of interest encodes a hematopoietic protein.
8. The method of claim 7, wherein the hematopoietic protein is a colony stimulating factor.
9. The method of claim 8, wherein the colony stimulating factor is GM-CSF (granulocyte-macrophage colony stimulating factor), G-CSF (granulocyte colony stimulating factor), or M-CSF (macrophage colony stimulating factor).
10. The method of claim 1, wherein the gene of interest encodes an interleukin (IL).
11. The method of claim 1, wherein the gene of interest encodes a growth hormone.
12. The method of claim 11, wherein the growth hormone is selected from the group consisting of human, bovine, porcine, avian, ovine, piscine, and equine growth hormone, and polypeptide analogs thereof having the biological activity of the corresponding naturally occurring growth hormone.

13. The method of claim 1, wherein the gene of interest is a viral gene.

14. The method of claim 13, wherein the viral gene is a retroviral gene.

15. The method of claim 14, wherein the retroviral gene is a gene from the HIV (human immunodeficiency virus), HTLV-1 (human T-cell lymphocyte virus-1) or HTLV-2 (human T-cell lymphocyte virus-2) virus.

16. The method of claim 1, wherein the viral gene is a gene from a hepatitis virus, a herpes virus, a papilloma virus, or a cytomegalvirus.

17. The method of claim 13, wherein the viral gene is a gene from an animal virus.

18. The method of claim 17, wherein the animal virus is a pseudorabies, Marek's, Newcastle's Disease, or IBR virus.

19. The method of claim 1, wherein the gene of interest is a protozoan gene.

20. The method of claim 19, wherein the protozoan is selected from the group consisting of Trypanosoma, Plasmodium, Leishmania, Giardia, Entamoeba, Toxoplasma, Babesia, and Cryptosporidiosis.

21. The method of claim 1, wherein the gene of interest is a helminth gene.

22. The method of claim 1, wherein the gene of interest is an oncogene.

23. The method of claim 22, wherein the oncogene is the phl-abl, H-ras, N-ras, K-ras, neu, or src.

24. The method of claim 1, wherein the gene of interest encodes a naturally occurring receptor.

25. The method of claim 24, wherein the receptor is the human low density lipoprotein (LDL) receptor.

26. The method of claim 24, wherein the receptor is the receptor for a hematopoietic protein selected from the group consisting of M-CSF (macrophage colony stimulating factor), G-CSF (granulocyte colony stimulating factor), GM-CSF (granulocyte-macrophage colony stimulating factor), and EPO (erythropoietin).

27. The method of claim 24, wherein the receptor is the receptor for an interleukin (IL) selected from the group consisting of IL-1, IL-2, IL-3, IL-4, IL-5, IL-6, IL-7 and IL-8.

28. The method of claim 24, wherein the receptor is cell surface protein which mediates infection of the cell by a virus.

29. The method of claim 28, wherein the virus is selected from the group consisting of HIV, HTLV-1, HTLV-2, a hepatitis virus, a herpes virus, an animal virus, a papilloma virus, a cytomegalo virus, and a rhinovirus.

30. The method of claim 1, wherein in (c) the protein is not the protein encoded by the gene of interest.

31. The method of claim 1, wherein the chemical directly binds to a DNA-binding protein or a DNA-binding protein complex.

32. The method of claim 1, wherein the chemical directly binds to a RNA-binding protein or a RNA-binding protein complex.

33. The method of claim 1, wherein the protein of (c) (i) or (c) (ii) is a protein which chemically modifies a DNA-binding protein or a DNA-binding protein complex and the chemical binds directly to said protein.

34. The method of claim 1, wherein the protein of (c) (i) or (c) (ii) is a protein which chemically modifies a RNA-binding protein or a RNA-binding protein complex and the chemical binds directly to said protein.

35. The method of claim 7, wherein the hematopoetic protein is EPO.

36. The method of claim 1, wherein the cell is a yeast cell or a fungal cell.

37. The method of claim 1, wherein the gene of interest is a yeast gene or a fungal gene.

38. The method of claim 1, wherein the gene of interest encodes a growth factor.

39. The method of claim 38, wherein the growth factor comprises TGF-$\beta$.

40. The method of claim 39, wherein the TGF-$\beta$ is TGF-$\beta$1, TGF-$\beta$2 or TGF-$\beta$3.

* * * * *